(12) United States Patent
Fujii et al.

(10) Patent No.: US 9,404,912 B2
(45) Date of Patent: Aug. 2, 2016

(54) ANALYSIS DEVICE DRIVING APPARATUS

(71) Applicant: Panasonic Corporation, Kadoma-shi, Osaka (JP)

(72) Inventors: Yoshiyuki Fujii, Ehime (JP); Kenji Okada, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 183 days.

(21) Appl. No.: 14/161,433

(22) Filed: Jan. 22, 2014

(65) Prior Publication Data
US 2014/0134082 A1    May 15, 2014

Related U.S. Application Data

(62) Division of application No. 12/740,462, filed as application No. PCT/JP2008/003040 on Oct. 27, 2008, now Pat. No. 8,667,833.

(30) Foreign Application Priority Data

Oct. 29, 2007  (JP) .................................. 2007-279738
Mar. 7, 2008   (JP) .................................. 2008-057113
Jun. 5, 2008   (JP) .................................. 2008-147520
Jul. 9, 2008   (JP) .................................. 2008-178536

(51) Int. Cl.
*B04B 7/02*    (2006.01)
*G01N 21/07*   (2006.01)
(Continued)

(52) U.S. Cl.
CPC . *G01N 33/50* (2013.01); *B01L 3/50* (2013.01); *B01L 3/502715* (2013.01); *B01L 3/502738* (2013.01); *B04B 7/00* (2013.01); *B04B 7/02* (2013.01); *G01N 1/28* (2013.01); *G01N 21/07* (2013.01); *G01N 33/4875* (2013.01);
(Continued)

(58) Field of Classification Search
None
See application file for complete search history.

(56) References Cited

U.S. PATENT DOCUMENTS 3,856,470 A * 12/1974 Cullis .................... G01N 21/07
                                                   356/427
4,883,763 A    11/1989 Holen et al.
(Continued)

FOREIGN PATENT DOCUMENTS

CN    1755371    4/2006
EP    0407827    1/1991
(Continued)

OTHER PUBLICATIONS

Partial Supplementary European Search Report, May 8, 2015; European Patent Application No. 08845860.9 (6 pages).
(Continued)

*Primary Examiner* — Neil N Turk
(74) *Attorney, Agent, or Firm* — Hamre, Schumann, Mueller & Larson, P.C.

(57) ABSTRACT

A protective cap 2 is engaged with a latch 10 of a diluent container 5 so as to fix the diluent container 5 at a liquid holding position of a diluent container containing section 11. The engagement is released when the protective cap 2 is set to an open position against the engagement so as to expose an inlet 13. When the protective cap 2 is shifted from the open position to a closed position, the protective cap 2 pushes the diluent container 5 into a liquid discharge position. Thus, it is possible to preserve a diluent for a long period of time and to easily open the diluent container 5 without having to complicate the structure of an analysis apparatus.

2 Claims, 45 Drawing Sheets

(51) Int. Cl.
  B04B 7/00 (2006.01)
  B01L 3/00 (2006.01)
  G01N 33/50 (2006.01)
  G01N 33/487 (2006.01)
  G01N 35/02 (2006.01)
  G01N 1/28 (2006.01)
  G01N 33/49 (2006.01)
  G01N 35/00 (2006.01)
  G01N 35/04 (2006.01)
  G01N 35/10 (2006.01)

(52) U.S. Cl.
  CPC ........... G01N35/025 (2013.01); *B01L 2200/16* (2013.01); *B01L 2300/042* (2013.01); *B01L 2300/043* (2013.01); *B01L 2300/044* (2013.01); *B01L 2300/0803* (2013.01); *B01L 2300/0867* (2013.01); *B01L 2400/0409* (2013.01); *B01L 2400/0683* (2013.01); *G01N 33/49* (2013.01); *G01N 2035/00504* (2013.01); *G01N 2035/0403* (2013.01); *G01N 2035/1032* (2013.01); *Y10T 436/11* (2015.01); *Y10T 436/111666* (2015.01)

(56) References Cited

U.S. PATENT DOCUMENTS

| | | | | |
|---|---|---|---|---|
| 5,344,380 | A | * | 9/1994 | Chern ................... B04B 5/0414 16/110.1 |
| 5,851,169 | A | * | 12/1998 | Meresz .................. B04B 7/00 279/140 |

| | | | |
|---|---|---|---|
| 2002/0090737 | A1 | 7/2002 | Levin et al. |
| 2003/0031595 | A1 | 2/2003 | Kirchhevel et al. |
| 2006/0073584 | A1 | 4/2006 | Sasaki et al. |
| 2006/0275852 | A1 | 12/2006 | Montagu et al. |

FOREIGN PATENT DOCUMENTS

| | | |
|---|---|---|
| JP | 46-31342 Y | 10/1971 |
| JP | 55-117955 U | 8/1980 |
| JP | 3-46566 | 2/1991 |
| JP | 3-98743 U | 10/1991 |
| JP | 5-246450 | 9/1993 |
| JP | 07-500910 | 1/1995 |
| JP | 7-503794 | 4/1995 |
| JP | 9-278048 | 10/1997 |
| JP | 3202662 B | 6/2001 |
| JP | 2002-63759 | 2/2002 |
| JP | 2006-343206 | 12/2006 |
| JP | 2007-58893 | 3/2007 |
| JP | 2003-185671 | 7/2008 |
| WO | WO 93/08893 | 5/1993 |
| WO | WO 93/16391 | 8/1993 |
| WO | 2006/074665 | 7/2006 |
| WO | WO 2008/001796 | 1/2008 |

OTHER PUBLICATIONS

Form PTO-892 issued in Office Action in co-pending U.S. Appl. No. 14/161,437 on Sep. 21, 2015.

* cited by examiner

FIG. 12
(a)
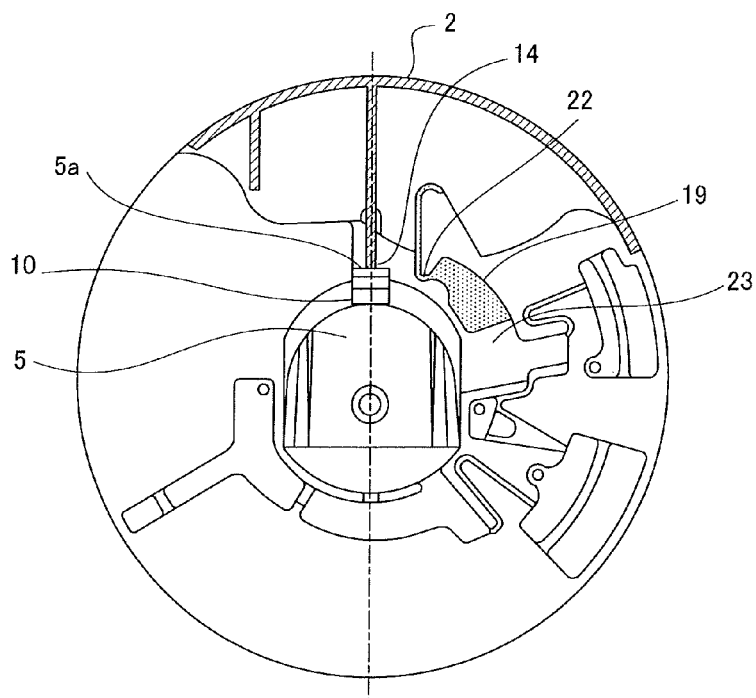
(b)
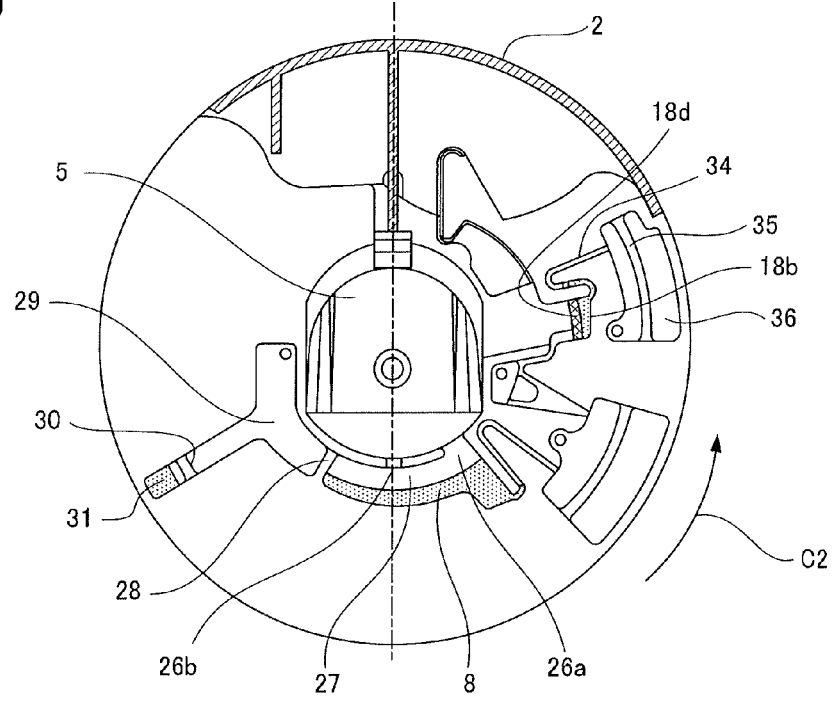

FIG. 14
(a)
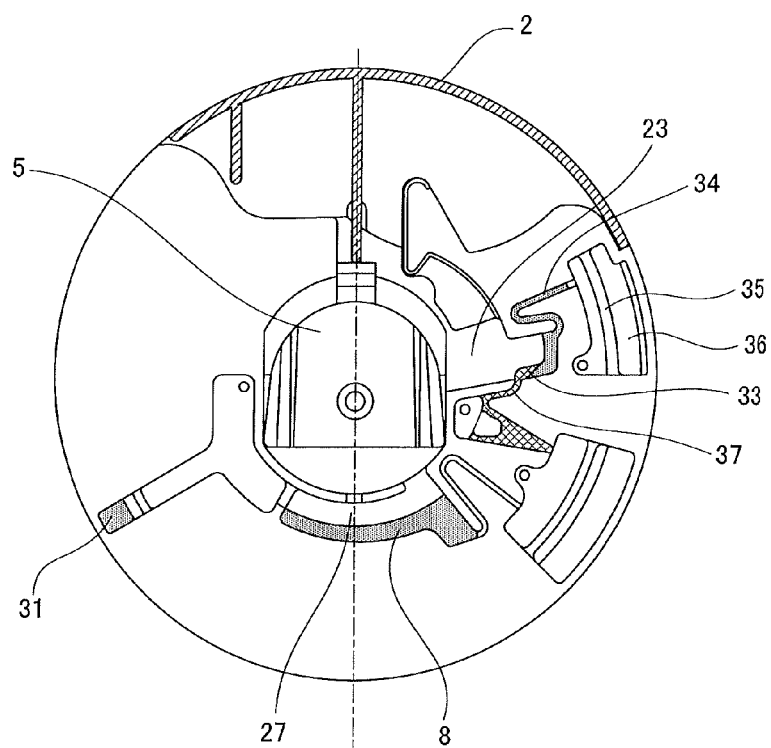
(b)
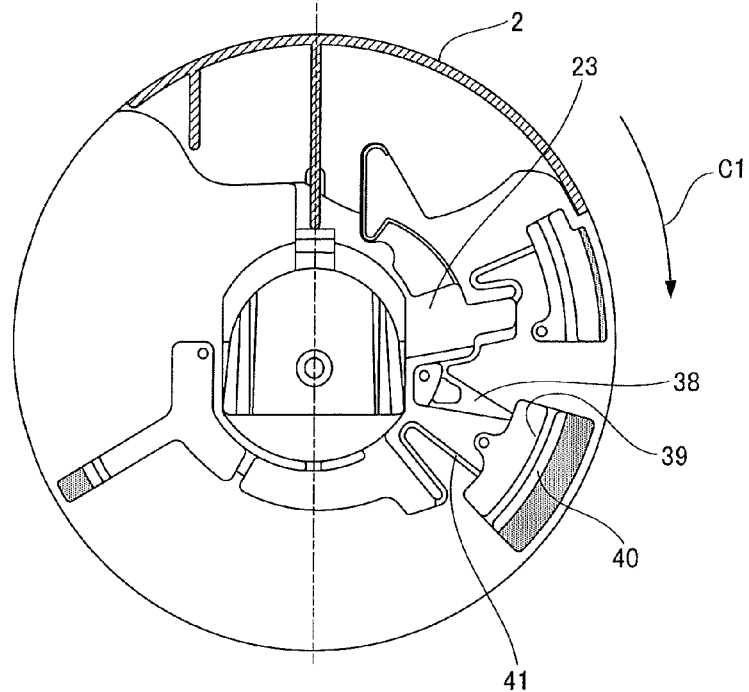

FIG. 15A
FIG. 15B
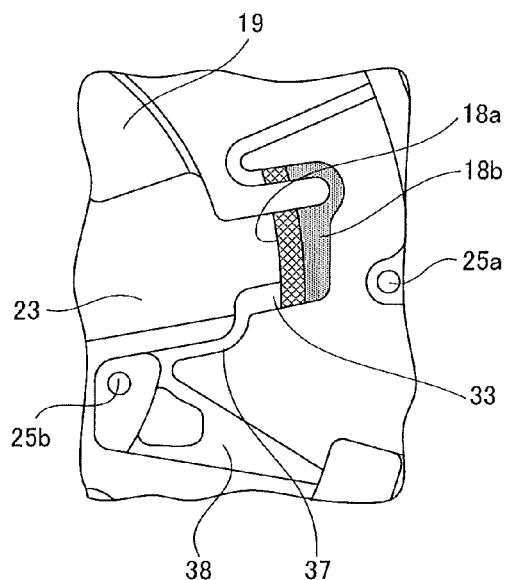
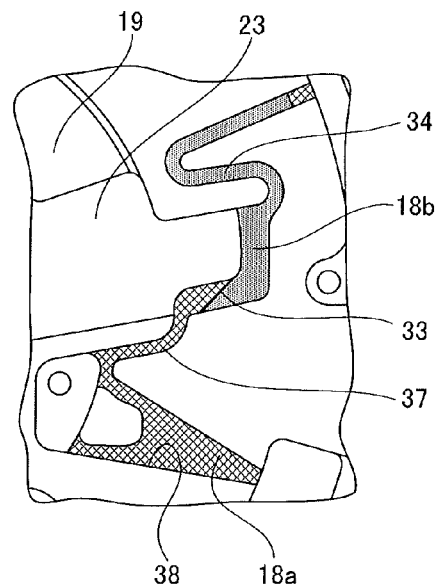
FIG. 15C
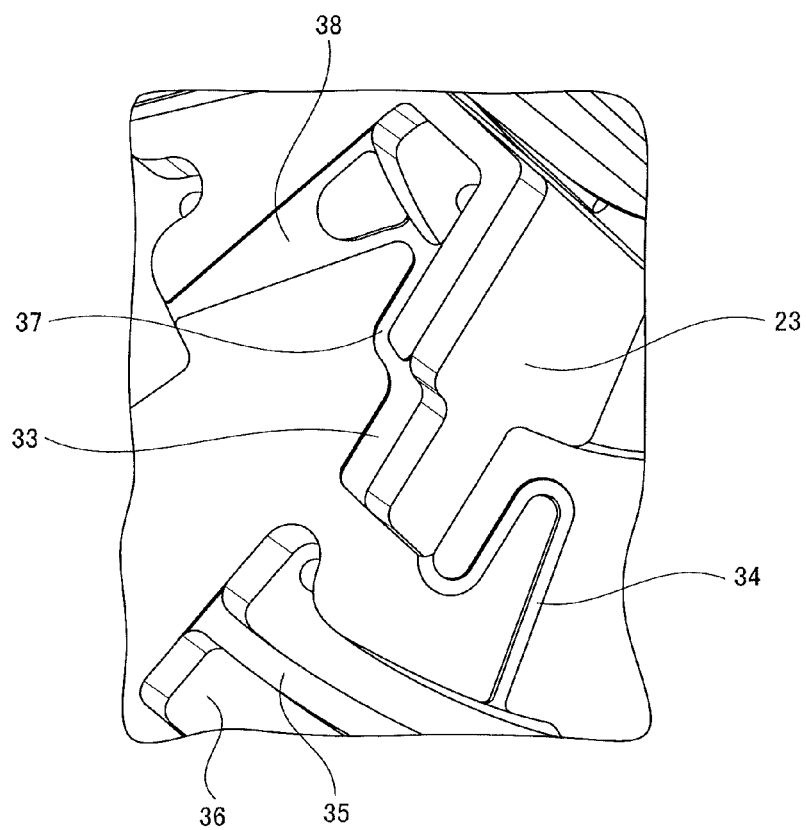

ANALYSIS DEVICE DRIVING APPARATUS

TECHNICAL FIELD

The present invention relates to an analysis device to be used to analyze a liquid collected from a living organism or the like, and to an analysis apparatus and an analysis method using the same. More specifically, the present invention relates to a technique of opening a diluent container holding a diluent for diluting a sample liquid within an analysis device.

BACKGROUND ART

Conventionally, as a method of analyzing a liquid collected from a living organism or the like, an analysis method is known that uses an analysis device in which a liquid channel is formed. The analysis device is capable of controlling a fluid using a rotating apparatus. Since the analysis device is capable of performing dilution of a sample liquid, solution measurement, separation of solid components, transfer and distribution of a separated fluid, mixing of a solution and a reagent, and the like by utilizing centrifugal force, various biochemical analyses can be carried out.

In particular, while the dilution of a sample liquid is a necessary process when analyzing a minute sample, having to inject a required amount of diluent into an analysis device from the outside every time a measurement is to be performed is not user-friendly. Therefore, configurations are considered in which a diluent container holding a diluent is contained, in advance, in an analysis device and the diluent container can be readily opened.

In the case of an analysis device described in Patent Document 1 (National Publication of International Patent Application No. 07-503794) which dilutes a sample liquid to perform analysis, as illustrated in FIG. 51A, a diluent container 51 is contained in a chamber 50 in the analysis device. The diluent container 51 includes a thin-film seal 52 and a rigid side section 54 having a scribed mark 53. The diluent container 51 is held at a predetermined position by a holding post 55. FIG. 51B illustrates a state where a spindle or a post 56 has entered the chamber 50 through a receiving hole 57. At this position, the post 56 moves the diluent container 51 towards a receiving chamber 58 while the rigid side section 54 splits along the scribed mark 53 so as to form an opening 59. A diluent held in the diluent container 51 flows out due to the rotation of a rotor and is transferred into the receiving chamber 58 via an exit channel 60. The receiving chamber 58 is a mixing chamber in which a sample liquid and the diluent are mixed.

In addition, an analysis device described in Patent Document 2 (Japanese Patent Laid-Open No. 03-046566) is configured such that a liquid supply reservoir 62 is contained in an analysis device main body 61 as illustrated in FIG. 52. A liquid reagent 63 held in the liquid supply reservoir 62 is introduced into a reaction path 66 by pulling a terminal 65 of a film 64. Subsequently, due to gravity, the liquid reagent 63 freely flows into a corner 68 of the reaction path 66 along a path depicted by a dashed arrow 67. A sample is retrieved by an operation of introducing a capillary holder 69 into the analysis device main body 61. Reference numerals 70, 71, and 72 denote reagents.

An analysis device 50B described in Patent Document 3 (National Publication of International Patent Application No. 07-500910) which transfers a solution utilizing centrifugal force is arranged so as to inject a sample liquid into a measuring chamber 52B from an inlet 51B with an insertion tool such as a pipette as illustrated in FIG. 53, and after holding the sample liquid by a capillary force of the measuring chamber 52B, transfer the sample liquid to a separation chamber 53B by the rotation of the analysis device 50B. Providing such an analysis device which uses centrifugal force as a power source for liquid transfer with a disk-like shape enables microchannels for liquid transfer control to be arranged radially. Since no wasted area is created, the disk-like shape is used as a favorable shape.

A configuration illustrated in FIGS. 26 and 27 is conceivable as an analysis device driving apparatus that rotationally drives a detachably set analysis device 50B.

As illustrated in FIG. 26, an analysis device 1 in which is set a sample liquid is set on a rotor 101. With a door 103 closed, the analysis device 1 is sandwiched using a clamper 116. By rotationally moving the rotor 101, the sample liquid is transferred inside the analysis device 1 and is then analyzed or centrifugally separated.

FIG. 27 illustrates a state where the analysis device 1 is set on the rotor 101 and the door 103 is closed. In FIG. 27, the door 103 rotationally moves around a support shaft 114 and is openable and closable.

A groove 102 is formed on an upper face of the rotor 101. When the analysis device 1 is set on the rotor 101, an engaging section 15 of the analysis device 1 is engaged with the groove 102. When the analysis device 1 is set on the rotor 101 and the door 103 is closed before rotating the rotor 101, the clamper 116 provided on a side of the door 103 pushes a position of the set analysis device 1 on the rotation axial center of the rotor 101 towards the rotor 101 using a biasing force of a spring 105, thereby causing the analysis device 1 to integrally rotate with the rotor 101 that is rotationally driven by a rotational driving unit 106. Reference numeral 107 denotes an axial center during rotation of the rotor 101.

Blood contained in a sample liquid remains on a used analysis device. Therefore, a risk of infection exists when the protective cap 2 is deliberately opened.

With respect to liquid storage containers for food, hygiene products, fuel, medicinal substances such as pesticides, and the like, and containers with lids such as in-store display cases for rental videos and the like, as seen in Patent Document 4 (Japanese Patent No. 3202662), various containers with lock functions which prevent the lids of the containers from being inadvertently or intentionally opened are being provided.

Patent Document 1: National Publication of International Patent Application No. 07-503794
Patent Document 2: Japanese Patent Laid-Open No. 03-046566
Patent Document 3: National Publication of International Patent Application No. 07-500910
Patent Document 4: Japanese Patent No. 3202662

DISCLOSURE OF THE INVENTION

Problems to be Solved by the Invention

However, in Patent Document 1, the thickness of the container at the portion of the scribed mark 53 is reduced and the moisture permeability of the diluent container 51 is increased in order to make the diluent container 51 more readily breakable. In addition, since a resin member having rigidity must also be used for the thin-film seal 52, the moisture permeability of the seal portion increases. Therefore, a diluent inside the diluent container 51 cannot be preserved for a long period of time, resulting in variations in liquid volume and reagent concentration which affect measurement accuracy. Moreover, the necessity of providing the analysis apparatus with a mechanism for operating the post 55 disadvantageously complicates the structure and increases the cost of the apparatus.

In addition, in Patent Document 2, operations to be performed by a user before setting the analysis device to an analysis apparatus includes: an operation of collecting a sample liquid with a sample collecting capillary 73 of the capillary holder 69; an operation of introducing the capillary holder 69 into the analysis device main body 61; and an operation of pulling the film 64 of the liquid supply reservoir 62. This results in low operability for a user and creates a risk of erroneous operations. Furthermore, since the film 64 must be peeled off and discarded, the amount of waste as well as the burden on a user disadvantageously increase.

The present invention has been made to solve such conventional problems, and an object thereof is to provide an analysis device capable of preserving a diluent over a long period of time and enabling a diluent container to be easily opened without having to complicate the structure of an analysis apparatus, and an analysis apparatus and an analysis method using the analysis device.

In addition, with the configuration illustrated in FIG. 27, when an external force such as a vibration or an impact shock acts on the analysis device 1 during high-speed rotation, a failure occurs in which the analysis device 1 is uplifted and becomes detached from the rotor 101.

An object of the present invention is to provide a safe analysis device driving apparatus capable of avoiding the occurrence of a failure in which an analysis device detaches from a rotor during high-speed rotation and the like even when an external force acts during operation.

Furthermore, the configuration according to Patent Document 4 enables a locking mechanism to be released relatively easily and a lid to be repetitively opened and closed. As a result, there is a risk of occurrence of a serious accident when the lid is reopened such as the inclusion of a liquid such as blood which has a risk of secondary infection or a contaminant or, in a case of disposal of a used chemical such as a pesticide, contamination or secondary infection due to the reuse of the used chemical.

The present invention has been made in order to solve the conventional problems described above, and an object thereof is to provide a lidded container including a locking mechanism capable of preventing the reopening of a lid.

Means for Solving the Problems

An analysis device according to the present invention is an analysis device having a microchannel structure that transfers a sample liquid towards a measurement spot by centrifugal force and which is used for reading involving accessing a reaction liquid at the measurement spot, the analysis device including: an analysis device main body having, formed inside, a microchannel structure with minute surface irregularities; a protective cap that exposes, in an open position, an inlet for collecting a sample liquid into the microchannel structure, and in a closed position, covers a part of the analysis device main body and prevents scattering of the sample liquid from the inlet; a diluent container whose opening is sealed by a seal member so as to internally hold a diluent; a diluent container containing section formed inside the analysis device main body and which contains the diluent container so as to be movable between a liquid holding position and a liquid discharge position; and a protrusion provided so as to protrude along a movement path of the diluent container from the liquid holding position to the liquid discharge position in the diluent container containing section and which breaks the seal member of the diluent container having moved to the liquid discharge position so as to open the diluent container, wherein the diluent container is moved to the open position where the seal member engages the protrusion to be broken by a shifting of the protective cap from the open position to the closed position, and the diluent container and a part of the protective cap at the closed position before moving to the open position to expose the inlet are in direct or indirect engagement with each other so as to lock the diluent container to the liquid holding position and prevent the diluent container from moving to the liquid discharge position.

In addition, an analysis device according to the present invention further includes: a latch provided on the diluent container on a side of the protective cap, wherein the diluent container and the protective cap at the closed position before moving to the open position to expose the inlet are in engagement with the latch of the diluent container so as to lock the diluent container to the liquid holding position of the diluent container containing section, the engagement of the latch of the diluent container and the protective cap is released by setting the protective cap to the open position against the engagement and exposing the inlet, and when closing the protective cap from the open position to the closed position, the protective cap abuts on a face of the latch of the diluent container on a side of the protective cap so as to push the diluent container into the liquid discharge position.

Furthermore, in an analysis device according to the present invention, a seal face on which the seal member of the diluent container is to be applied is obliquely formed.

Moreover, the analysis device main body includes: a hole provided so as to enable a locking jig to protrude along the movement path; and a groove provided on any of an upper face and a lower face of the diluent container and which locks the diluent container when the locking jig engages the diluent container through the hole at the liquid holding position.

In addition, a bottom of the diluent container that is on a side opposite to an opening sealed by the seal member is formed by an arc face.

An analysis apparatus according to the present invention is an analysis apparatus in which is set an analysis device including: an analysis device main body having, formed inside, a microchannel structure with minute surface irregularities; a protective cap that exposes, in an open position, an inlet for collecting a sample liquid into the microchannel structure, and in a closed position, covers a part of the analysis device main body and prevents scattering of the sample liquid from the inlet; a diluent container whose opening is sealed by a seal member so as to internally hold a diluent; a diluent container containing section formed inside the analysis device main body and which contains the diluent container so as to be movable between a liquid holding position and a liquid discharge position; and a protrusion provided so as to protrude along a movement path of the diluent container from the liquid holding position to the liquid discharge position in the diluent container containing section and which breaks the seal member of the diluent container having moved to the liquid discharge position so as to open the diluent container, the diluent container to be moved to the open position where the seal member engages the protrusion to be broken by a shifting of the protective cap from the open position to the closed position, and the diluent container and a part of the protective cap at the closed position before moving to the open position to expose the inlet are in direct or indirect engagement with each other so as to lock the diluent container to the liquid holding position and prevent the diluent container from moving to the liquid discharge position, wherein the analysis apparatus includes a rotation driving unit that rotates and stops the analysis device around an axial center so as to transfer the sample liquid and the diluent discharged from the diluent container to a measurement chamber, and an analysis unit that accesses and analyzes a solution in the measurement chamber.

An analysis method according to the present invention is an analysis method using an analysis device including: an analysis device main body having, formed inside, a microchannel structure with minute surface irregularities; a protective cap that exposes, in an open position, an inlet for collecting a sample liquid into the microchannel structure, and in a closed position, covers a part of the analysis device main body and prevents scattering of the sample liquid from the inlet; a diluent container whose opening is sealed by a seal member so as to internally hold a diluent; a diluent container containing section formed inside the analysis device main body and which contains the diluent container so as to be movable between a liquid holding position and a liquid discharge position; and a protrusion provided so as to protrude along a movement path of the diluent container from the liquid holding position to the liquid discharge position in the diluent container containing section and which breaks the seal member of the diluent container having moved to the liquid discharge position so as to open the diluent container, the diluent container to be moved to the open position where the seal member engages the protrusion to be broken by a shifting of the protective cap from the open position to the closed position, and the diluent container and a part of the protective cap at the closed position before moving to the open position to expose the inlet are in direct or indirect engagement with each other so as to lock the diluent container to the liquid holding position and prevent the diluent container from moving to the liquid discharge position, wherein the analysis method includes: spot-applying the sample liquid onto the inlet exposed by opening the protective cap of the analysis device and collecting the sample liquid, pushing the diluent container set in the diluent container containing section of the analysis device towards the protrusion provided so as to protrude along the movement path of the diluent container from the liquid holding position to the liquid discharge position of the diluent container containing section by an operation of the protective cap from the open position to the closed position, and pressing the seal member of the diluent container against the protrusion so as to break the seal member and open the diluent container; setting the analysis device opened by breaking the seal member onto a rotor having an axial center and rotating the rotor so as to dilute at least a portion of the sample liquid spot-applied to the analysis device by the diluent discharged from the diluent container; and accessing and analyzing a solution component diluted by the diluent or a reactant of a solution component diluted by the diluent and a reagent.

An analysis device driving apparatus according to the present invention is an analysis device driving apparatus that sets an analysis device in which a sample liquid is set onto a rotor and rotationally moves the rotor to transfer the sample liquid in the analysis device so as to analyze or centrifugally separate the sample liquid, wherein the analysis device driving apparatus includes: a clamper that sandwiches the analysis device with the rotor; a biasing unit that presses the clamper in a direction approaching the rotor; and a stopper unit positioned on an axial center of the clamper in a state where the Clamper and the rotor are sandwiching the analysis device and which abuts and regulates the analysis device from detaching from the rotor only when the clamper uplifts from the rotor against a biasing force of the biasing unit beyond a permissible value.

In addition, an analysis device driving apparatus according to the present invention includes a door that is opened or closed when attaching or detaching the analysis device to/from the rotor, wherein the biasing unit is made up of a flat spring that is longitudinally disposed in a radial direction of the rotor and whose tip abuts to an axial center of the clamper, and a protrusion provided on an inner face of the door as the stopper unit and having a height that abuts to the axial center of the clamper via the flat spring when the clamper uplifts from the rotor against a biasing force of the flat spring beyond a permissible value.

Furthermore, an analysis device driving apparatus according to the present invention is an analysis device driving apparatus that sets an analysis device in which a sample liquid is set onto a rotor and rotationally moves the rotor to transfer the sample liquid in the analysis device so as to analyze or centrifugally separate the sample liquid, the analysis device driving apparatus including: a clamper that sandwiches the analysis device with the rotor; a holding plate having a hole through which the clamper is inserted and which engages and supports the clamper in a stand-by state where the clamper and the rotor are not sandwiching the analysis device, and whose engagement with the clamper is released in a state where the clamper and the rotor are sandwiching the analysis device; and a biasing unit that presses the clamper in a direction approaching the rotor, wherein a gap between a face of the holding plate on a side of the rotor and a face that opposes the clamper in a state where the rotor and the clamper are sandwiching the analysis device is set to an abutting distance only when the clamper uplifts from the rotor against a biasing force of the biasing unit beyond a permissible value.

Moreover, an analysis device driving apparatus according to the present invention has a protrusion formed so as to protrude towards the clamper around the hole on a rotor-side face of the holding plate.

In addition, an analysis device driving apparatus according to the present invention has a protrusion formed so as to protrude towards the clamper on a face of the clamper opposing the holding plate.

An analysis device according to the present invention includes: an analysis device main body having, formed inside, a microchannel structure with minute surface irregularities; a protective cap that covers protection object locations of the analysis device main body; a hooked portion formed on one of the analysis device main body and the protective cap; and a locking piece formed in correspondence to the hooked portion on the other of the analysis device main body and the protective cap, wherein in a state where the protective cap is first moved to a position where the protection object locations of the analysis device main body are exposed and subsequently returned to a position where the protection object locations of the analysis device main body are covered, the hooked portion engages the locking piece so as to prevent the protective cap from moving to the position where the protection object locations of the analysis device main body are exposed.

In addition, in an analysis device according to the present invention, an end of the protective cap is pivotally supported by the analysis device main body so as to be rotationally movable between the position where the protection object locations of the analysis device main body are covered and the position where the protection object locations of the analysis device main body are exposed, the locking piece is provided on a primary face of the analysis device main body, and the hooked portion is provided on a primary face of the protective cap.

Furthermore, in an analysis device according to the present invention, an end of the protective cap is pivotally supported by the analysis device main body so as to be rotationally movable between the position where the protection object locations of the analysis device main body are covered and the position where the protection object locations of the analysis device main body are exposed, the locking piece is provided on a peripheral face adjacent to a primary face of the analysis device main body, and the hooked portion is provided on a peripheral face adjacent to a primary face of the protective cap.

Moreover, in an analysis device according to the present invention, protection object locations of the analysis device main body are arranged in an exposed state so as to be detachable by sliding the protective cap set at a position covering the protection object locations along a sliding face between the analysis device main body and the protective cap, the hooked portion is provided on a face along the sliding face of one of the analysis device main body and the protective cap, and the locking piece is provided on a face along the sliding face of the other of the analysis device main body and the protective cap.

Advantages of the Invention

With an analysis device according to the present invention and an analysis apparatus and an analysis method using the analysis device, since a diluent container can be opened by a minimal operation by a user for collecting a sample liquid and a diluent can be automatically transferred into the analysis device, analytical precision can be improved, analysis apparatuses can be simplified, cost can be reduced, and user operability can be improved.

With an analysis device driving apparatus and an analysis apparatus including the analysis device driving apparatus according to the present invention, since a stopper unit abuts on an axial center of a rotating clamper even when the clamper attempts to uplift beyond a permissible value due to an external force that acts during operation, the analysis device is prevented from detaching from a rotor.

With a lidded container using a reuse-preventing locking mechanism according to the present invention, since a lid member (protective cap) is locked and prevented from reopening by a simple lid opening/closing operation performed by a user, used containers can now be readily distinguished. Furthermore, by making it difficult to accidentally reuse used containers, syringes, and the like, it is now possible to prevent accidents such as infection or contamination from blood and the like.

BRIEF DESCRIPTION OF THE DRAWINGS

FIG. 12 is a cross-sectional view taken after setting an analysis device on an analysis apparatus and rotating the same, and a cross-sectional view taken after centrifugal separation;

FIG. 14 is a cross-sectional view taken when quantitatively collecting a solid component of a sample liquid after centrifugal separation, and a cross-sectional view taken when diluting the solid component of the sample liquid after centrifugal separation;

FIG. 15A is an enlarged plan view of substantial parts;

FIG. 15B is an enlarged plan view of a measurement holding state;

FIG. 15C is an enlarged perspective view of substantial parts;

BEST MODE FOR CARRYING OUT THE INVENTION

First Embodiment

First, a description will be given with reference to FIGS. 1 to 16 on an analysis device capable of preserving a diluent over a long period of time and easily opening a diluent container without having to complicate the structure of an analysis apparatus, and an analysis apparatus and an analysis method using the analysis device.

FIGS. 1 to 6 illustrate an analysis device.

Figure 1A:
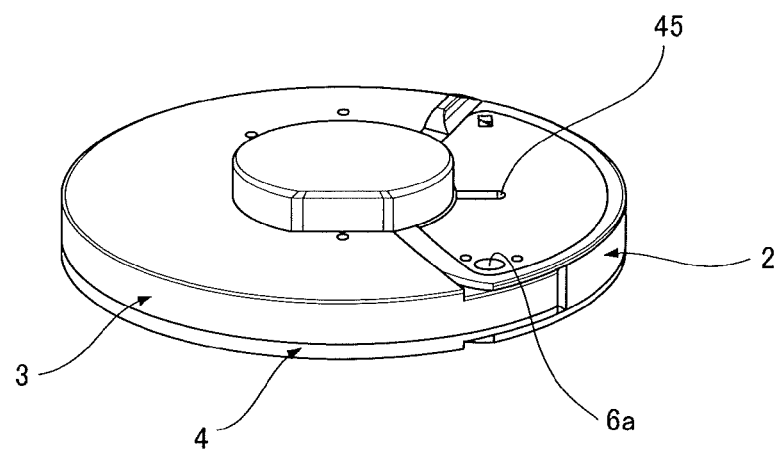
FIG. 1A is an external perspective view of a state where a protective cap of an analysis device according to an embodiment of the present invention is closed.
Figure 1B:
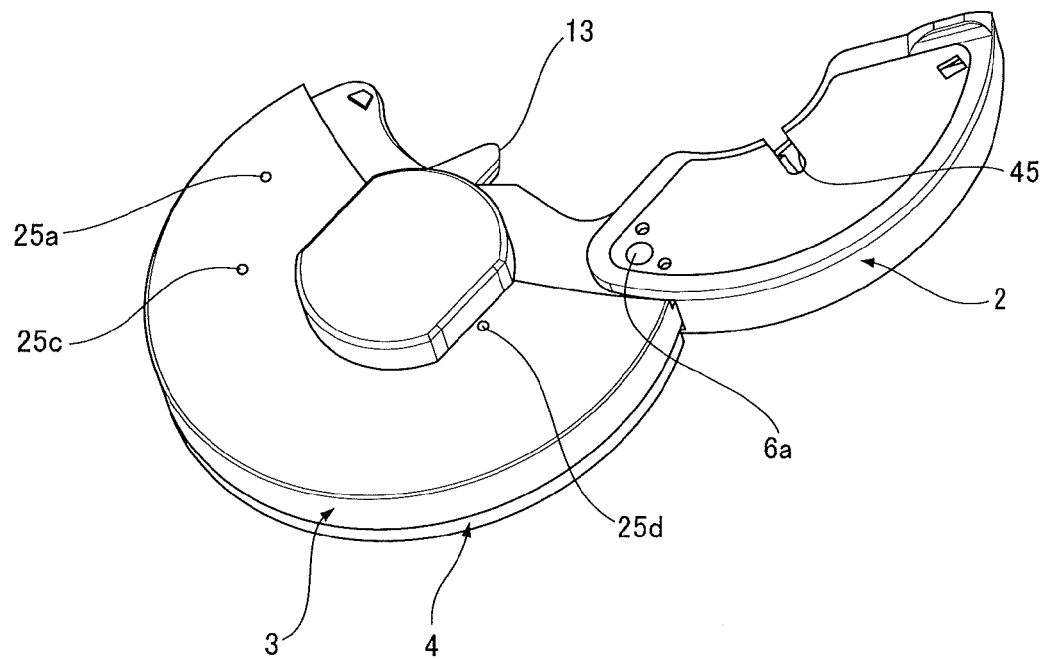
FIG. 1B is an external perspective view of a state where a protective cap of an analysis device according to an embodiment of the present invention is opened.

FIGS. 1A and 1B respectively illustrate a closed state and an opened state of a protective cap 2 of an analysis device 1.

Figure 2:
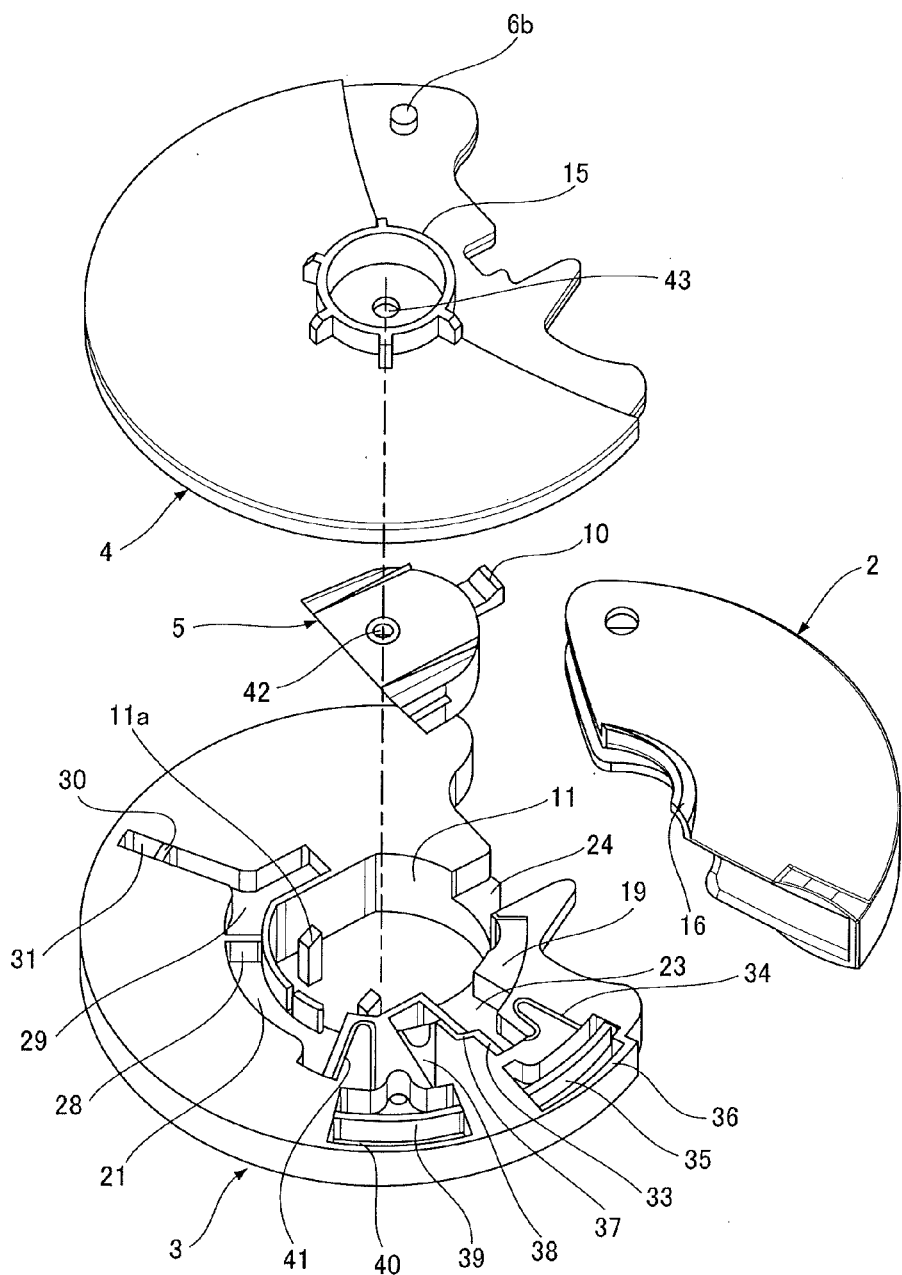
FIG. 2 is an exploded perspective view of an analysis device according to an embodiment of the present invention.
Figure 3:
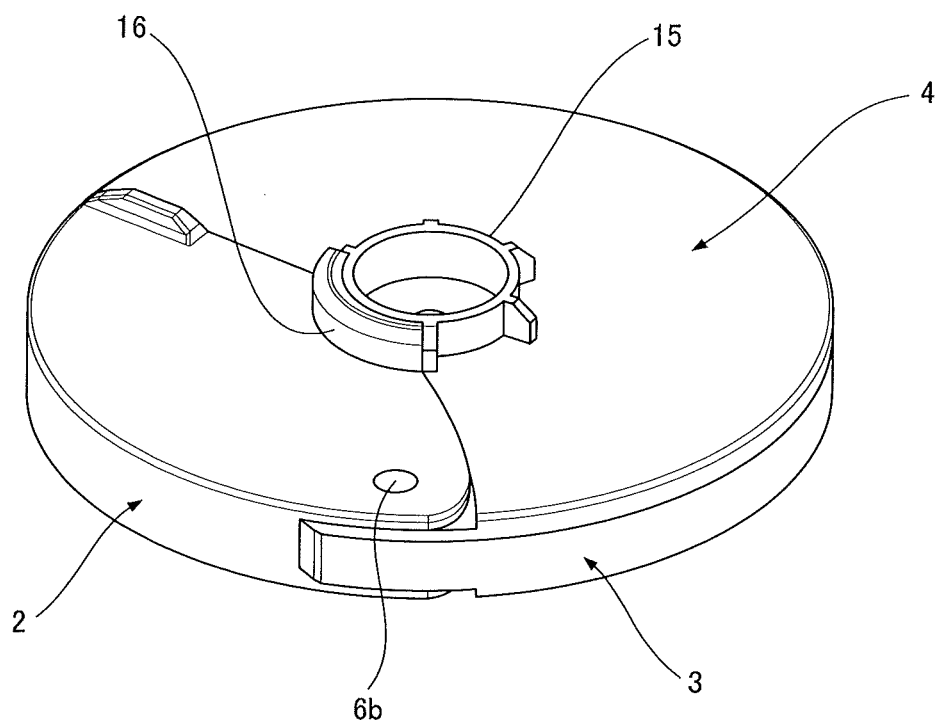
FIG. 3 is a perspective view of an analysis device in a state where a protective cap is closed as seen from behind.

FIG. 2 illustrates an exploded state when a lower side as illustrated in FIG. 1A is faced upwards. FIG. 3 is an assembly diagram of the same.

As illustrated in FIGS. 1 and 2, the analysis device 1 is made up of four parts including: a base substrate 3 with one face on which is formed a microchannel structure having minute irregularities on a surface thereof; a cover substrate 4 for covering a surface of the base substrate 3; a diluent container 5 holding a diluent; and a protective cap 2 for preventing scattering of a sample liquid.

The base substrate 3 and the cover substrate 4 are bonded in a state where the diluent container 5 and the like are internally set, whereby the protective cap 2 is attached to the base substrate 3 and the cover substrate 4 in the bonded state.

By covering the openings of the several depressions formed on the upper face of the base substrate 3 with the cover substrate 4, a plurality of containment areas to be described later (the same as the measurement spots to be described later) and channels having microchannel structures which interconnect the containment areas are formed. Among the containment areas, those required hold, in advance, reagents necessary for performing various analyses. One side of the protective cap 2 is pivotally supported so as to be capable of engaging shafts 6a and 6b formed on the base substrate 3 and the cover substrate 4 and to be openable and closable. When a sample liquid to be tested is blood, gaps between respective channels with microchannel structures in which capillary force acts are set to 50 μm to 300 μm.

An analysis process using the analysis device 1 described above can be summarized as spot-applying a sample liquid to the analysis device 1 in which a diluent has been set in advance, and performing measurement after diluting at least a portion of the sample liquid with the diluent.

Figure 4:
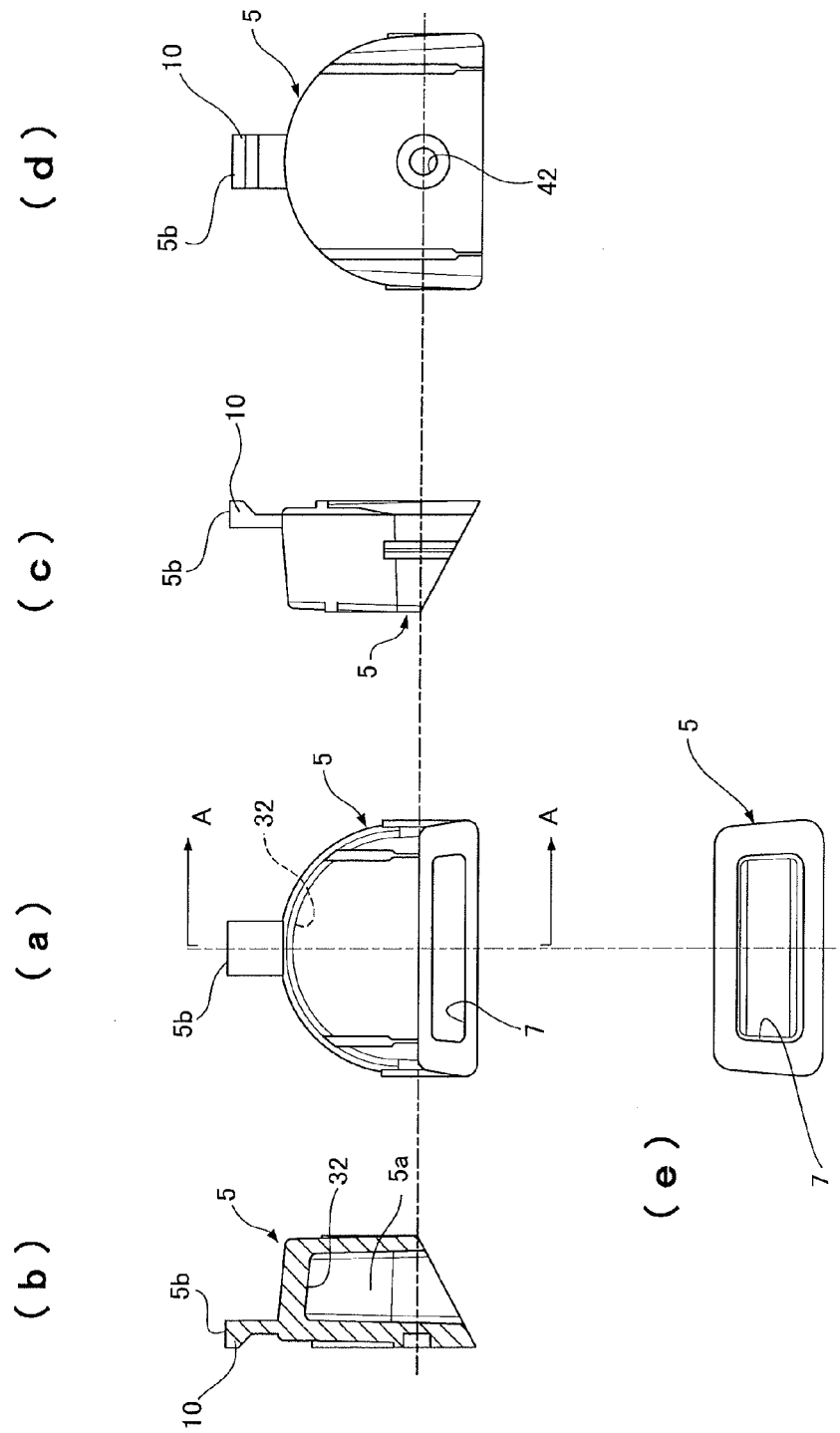
FIG. 4 is a plan view, an A-A cross-sectional view, a side view, a rear view, and a front view of a diluent container according to an embodiment of the present invention.

FIG. 4 illustrates shapes of the diluent container 5.

FIG. 4A is a plan view; FIG. 4B is a cross-sectional view taken along A-A in FIG. 4A; FIG. 4C is a side view; FIG. 4D is a rear view; and FIG. 4E is a front view as seen from an opening 7. The opening 7 is sealed by an aluminum seal 9 as a seal member after filling an inside 5a of the diluent container 5 with a diluent 8 as illustrated in FIG. 6A. A latch 10 is formed on a side of the diluent container 5 opposite to the opening 7. The diluent container 5 is set in and contained by a diluent container containing section 11 formed between the base substrate 3 and the cover substrate 4 so as to be movable to a liquid holding position illustrated in FIG. 6A and a liquid discharge position illustrated in FIG. 6C.

Figure 5:
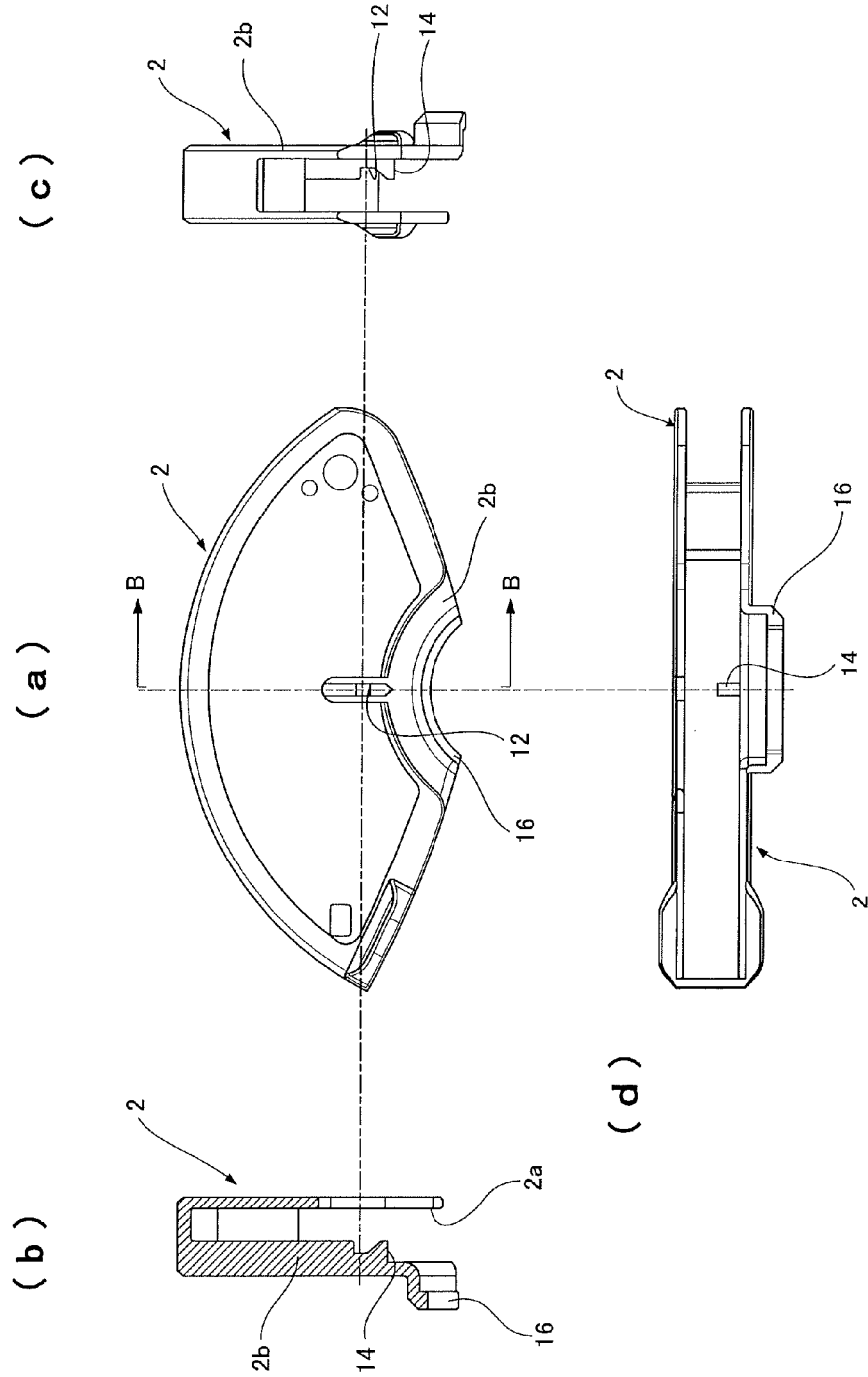
FIG. 5 is a plan view, a B-B cross-sectional view, a side view, a rear view, and a front view of a protective cap according to an embodiment of the present invention.
Figure 6:
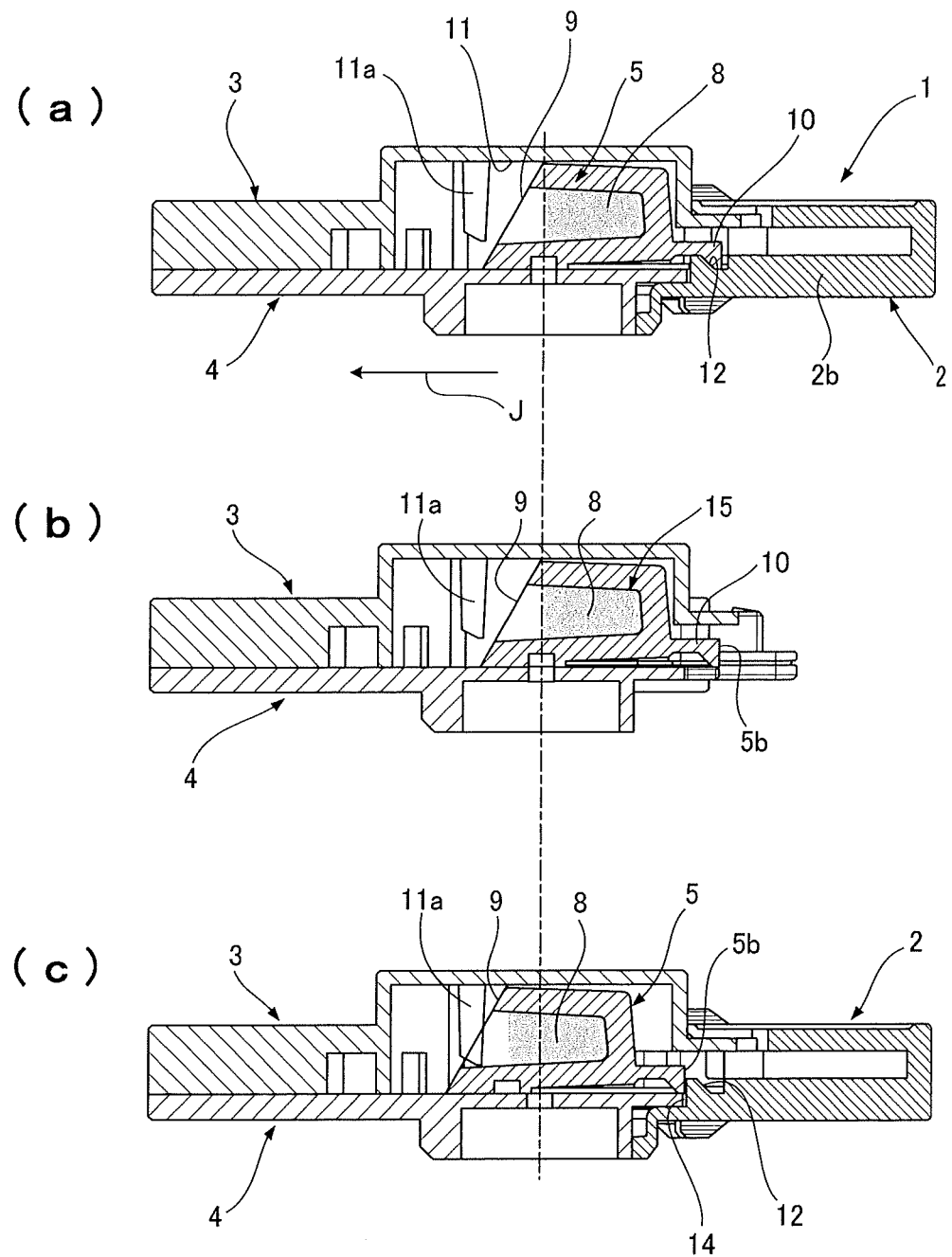
FIG. 6 is a cross-sectional view of an analysis device according to an embodiment of the present invention before use, a cross-sectional view of an analysis device when spot-applying a sample liquid, and a cross-sectional view of an analysis device when a protective cap is closed after having finished spot-applying the sample liquid.

FIG. 5 illustrates shapes of the protective cap 2.

FIG. 5A is a plan view; FIG. 5B is a cross-sectional view taken along B-B in FIG. 5A; FIG. 5C is a side view; FIG. 5D is a rear view. As illustrated in FIG. 6A, a locking groove 12 with which the latch 10 of the diluent container 5 can engage in a closed state illustrated in FIG. 1A is formed on an inner side of the protective cap 2.

FIG. 6A illustrates the analysis device 1 prior to use. In this state, the protective cap 2 is closed and the latch 10 of the diluent container 5 is in engagement with the locking groove 12 of the protective cap 2 so as to lock the diluent container 5 at the liquid holding position and prevent the diluent container 5 from moving in a direction depicted by arrow J. The analysis device 1 is supplied to a user in this state.

When the protective cap 2 is opened as illustrated in FIG. 1B against the engagement with the latch 10 illustrated in FIG. 6A upon spot-application of a sample liquid, a bottom 2b of the protective cap 2 on which the locking groove 12 is formed elastically deforms, causing the engagement between the locking groove 12 of the protective cap 2 and the latch 10 of the diluent container 5 to be released as illustrated in FIG. 6B.

In this case, a sample liquid is spot-applied to an exposed inlet 13 of the analysis device 1 and the protective cap 2 is closed. At this point, by closing the protective cap 2, a wall face 14 forming the locking groove 12 abuts a face 5b of the latch 10 of the diluent container 5 on a side of the protective cap 2 and pushes the diluent container 5 in the direction of the arrow J (in a direction approaching the liquid discharge position). An opening rib 11a is formed on the diluent container containing section 11 as a protrusion from a side of the base substrate 3. When the diluent container 5 is pushed by the protective cap 2, as illustrated in FIG. 6C, the aluminum seal 9 applied on the seal face of the inclined opening 7 of the diluent container 5 collides with and is broken by the opening rib 11a.

Figure 7:
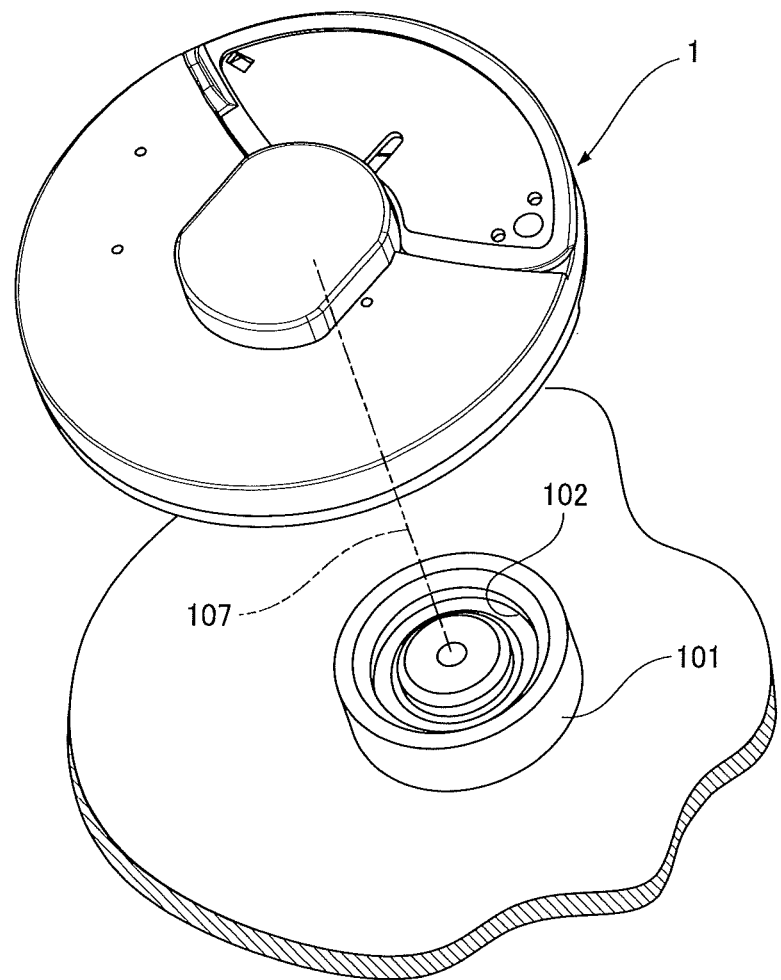
FIG. 7 is a perspective view taken immediately before setting an analysis device onto an analysis apparatus.
Figure 8:
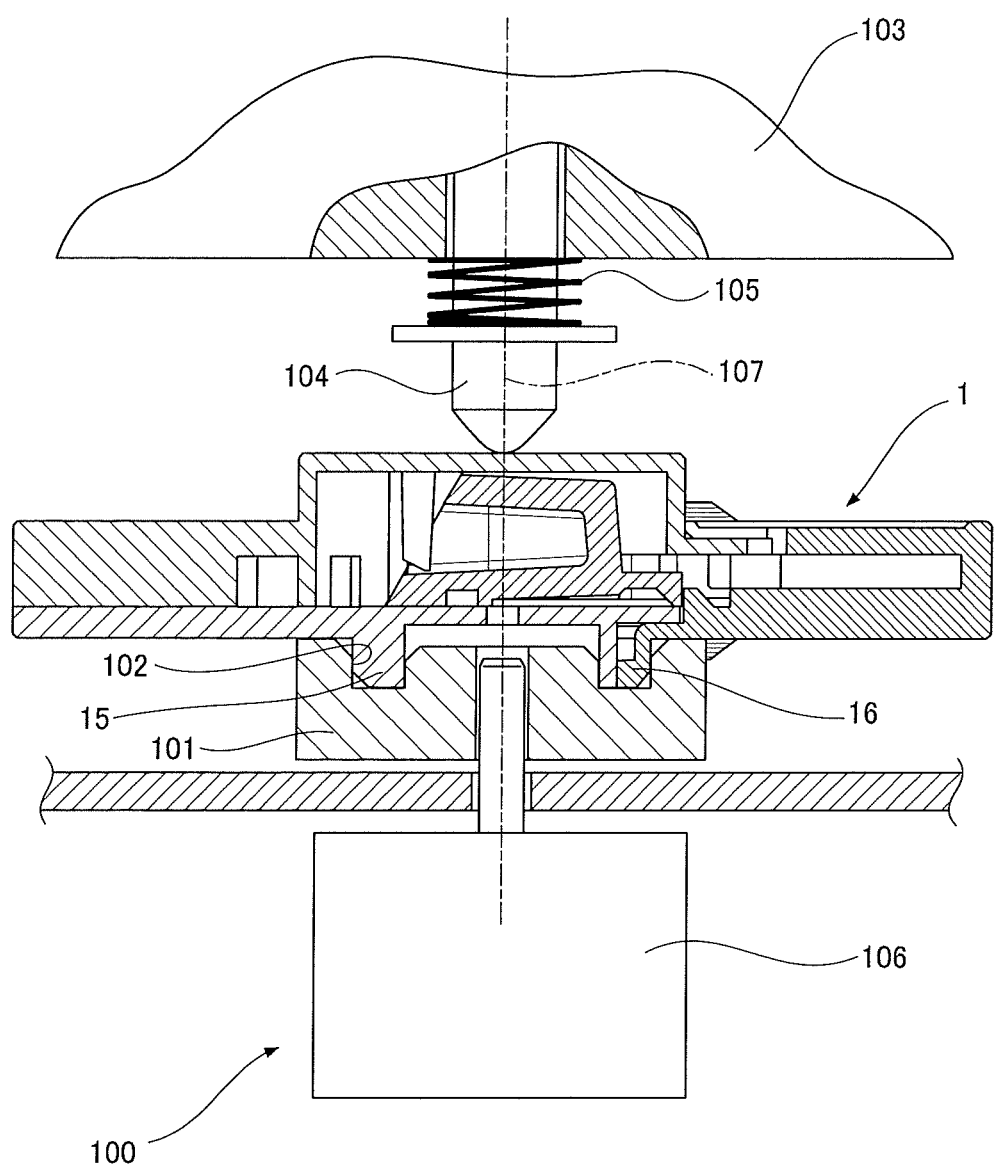
FIG. 8 is a cross-sectional view of a state where an analysis device has been set on an analysis apparatus.

A component analysis of a sample liquid can be performed by setting the analysis device 1 onto a rotor 101 of an analysis apparatus 100 with the cover substrate 4 facing downwards as illustrated in FIGS. 7 and 8.

A groove 102 is formed on an upper face of the rotor 101. When the analysis device 1 is set on the rotor 101, the engaging section 15 formed on the cover substrate 4 of the analysis device 1 and an engaging section 16 formed on the protective cap 2 engages the groove 102 and the analysis device 1 is contained.

After setting the analysis device 1 on the rotor 101, when a door 103 of the analysis apparatus is closed before rotating the rotor 101, a movable piece 104 provided on a side of the door 103 pushes a position of the set analysis device 1 on the rotation axial center of, the rotor 101 towards the rotor 101 using a biasing force of a spring 105, thereby causing the analysis device 1 to integrally rotate with the rotor 101 that is rotationally driven by a rotational driving unit 106. Reference numeral 107 denotes an axial center during rotation of the rotor 101. The protective cap 2 is attached in order to prevent sample liquid adhering to a vicinity of the inlet 13 from scattering to the outside due to centrifugal force during an analysis.

Resin material with low material cost and superior mass productivity is desirably used for the parts that make up the analysis device 1. Since the analysis apparatus 100 analyzes sample liquids using an optical measurement method in which light transmitted through the analysis device 1 is measured, a synthetic resin with a high transparency such as PC, PMMA, AS, MS, and the like is desirably used as the material for the base substrate 3 and the cover substrate 4.

In addition, since it is required that the diluent 8 be sealed inside the diluent container 5 over a long period of time, a crystalline synthetic resin with a low moisture permeability such as PP and PE is desirably used as the material of the diluent container 5. As for the material of the protective cap 2, any material with good moldability shall suffice. Inexpensive resins such as PP and PE are desirable.

The bonding between the base substrate 3 and the cover substrate 4 is desirably performed using a method that is unlikely to affect the reaction activity of reagents held in the containment areas. Desirable methods include ultrasonic welding and laser welding which are less likely to create reactive gases or solvents during bonding.

In addition, a portion for transferring a solution by a capillary force of a minute gap between the base substrate 3 and the cover substrate 4 formed by the bonding of the two substrates 3 and 4 is subjected to a hydrophilic treatment to enhance capillary force. Specifically, a hydrophilic treatment using a hydrophilic polymer or a surfactant is performed. In this case, hydrophilicity refers to a contact angle of less than 90 degrees with respect to water, and more favorably, a contact angle of less than 40 degrees.

Figure 9:
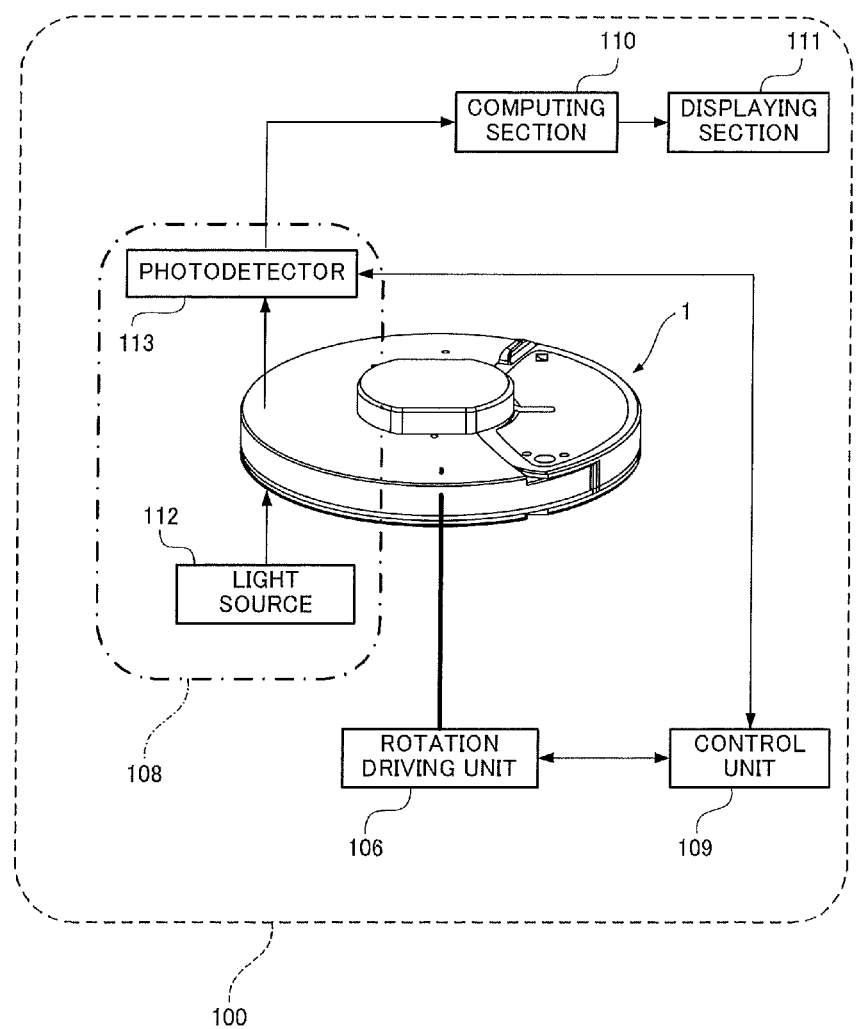
FIG. 9 is a configuration diagram of an analysis apparatus according to an embodiment of the present invention.

FIG. 9 illustrates a configuration of the analysis apparatus 100.

The analysis apparatus 100 is made up of: a rotation driving unit 106 for rotating the rotor 101; an optical measurement unit 108 for optically measuring a solution in the analysis device 1; a control unit 109 that controls the rotational speed and rotational direction of the rotor 101, the measurement timing of the optical measurement unit, and the like; a computing section 110 for processing a signal obtained by the optical measurement unit 108 and computing a measurement result; and a displaying section 111 for displaying a result obtained by the computing section 110.

In addition to rotating the analysis device 1 around the rotation axial center 107 via the rotor 101 in any direction at a predetermined rotational speed, the rotation driving unit 106 is arranged so as to be capable of causing the analysis device 1 to perform a left-right reciprocating movement centered around the rotation axial center 107 at a predetermined stop position and at a predetermined amplitude range and frequency so as to swing the analysis device 1.

The optical measurement unit 108 includes: a light source 112 for irradiating light to a measurement section of the analysis device 1; and a photodetector 113 that detects a light intensity of transmitted light having passed through the analysis device 1 among the light irradiated from the light source 112.

The analysis apparatus 100 is arranged such that, by rotationally driving the analysis device 1 by the rotor 101, a sample liquid or a solution taken inside from the inlet 13 is transferred inside the analysis device 1 by a centrifugal force that is generated by rotating the analysis device 1 around the rotation axial center 107 positioned circumferentially inward from the inlet 13 and by a capillary force of a capillary channel provided inside the analysis device 1. A microchannel structure of the analysis device 1, together with analysis processes, will now be described in detail.

FIG. 10 illustrates a vicinity of the inlet 13 of the analysis device 1.

Figure 10A:
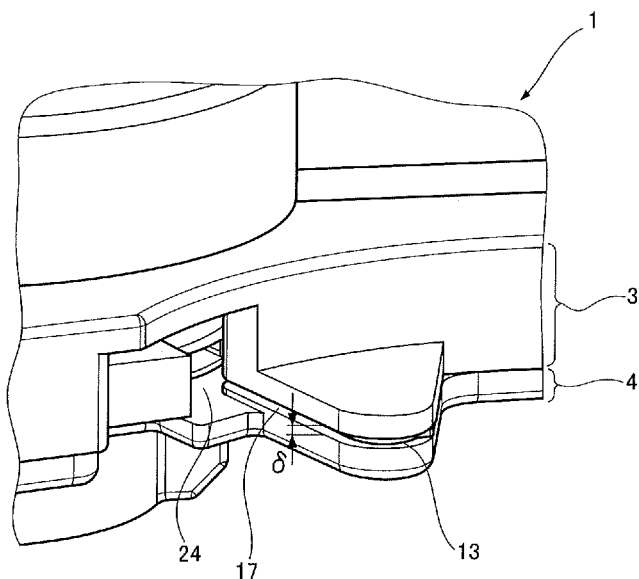
FIG. 10A is an enlarged perspective view of substantial parts of an analysis device according to an embodiment of the present invention.
Figure 10B:
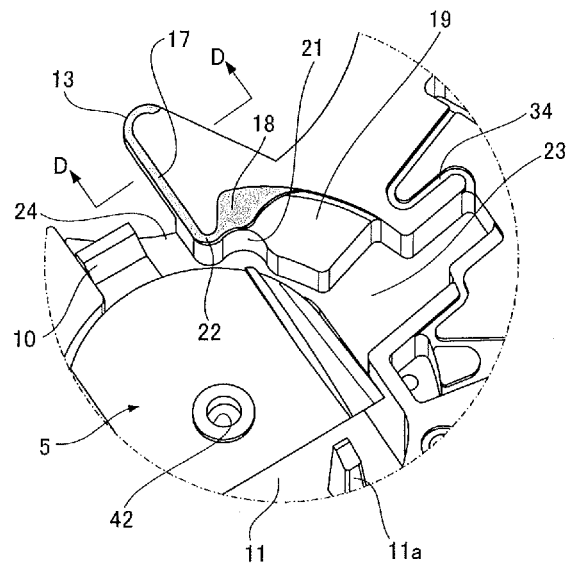
FIG. 10B is an enlarged explanatory diagram of a base substrate that is a substantial part of an analysis device according to an embodiment of the present invention.

FIG. 10A is an enlarged view of the inlet 13 as seen from the outside of the analysis device 1, and FIG. 10B is an enlarged view of the microchannel structure as seen through the cover substrate 4 from a side of the rotor 101.

Figure 10C:
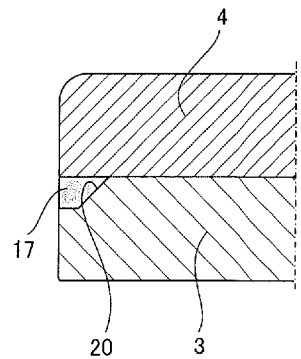
FIG. 10C is a cross-sectional view of substantial parts of an analysis device according to an embodiment of the present invention.

The inlet 13 is connected via a guide section 17 formed between the base substrate 3 and the cover substrate 4 and having a minute gap δ at which a capillary force acts to a capillary cavity 19 that is a gap at which a capillary force acts in the same manner as the guide section 17 and which has a volume capable of holding a necessary amount of a sample liquid 18. Instead of being a rectangular shape whose back end-side is vertical, a cross-sectional shape (a D-D cross section illustrated in FIG. 10B) perpendicular to a flow direction of the guide section 17 is formed by an inclined face 20 that gradually narrows towards a back end thereof in the direction of the cover substrate 4 as illustrated in FIG. 10C. A bent section 22 that forms a recess 21 on the base substrate 3 and alters the direction of a passage is formed at a connected portion between the guide section 17 and the capillary cavity 19.

Seeing from the guide section 17, a separation cavity 23 with a gap at which capillary force does not act is formed via and beyond the capillary cavity 19. A cavity 24 whose one end is connected to the separation cavity 23 and the other end opened to the air is formed to a side of the capillary cavity 19 and parts of the bent section 22 and the guide section 17.

Figure 11:
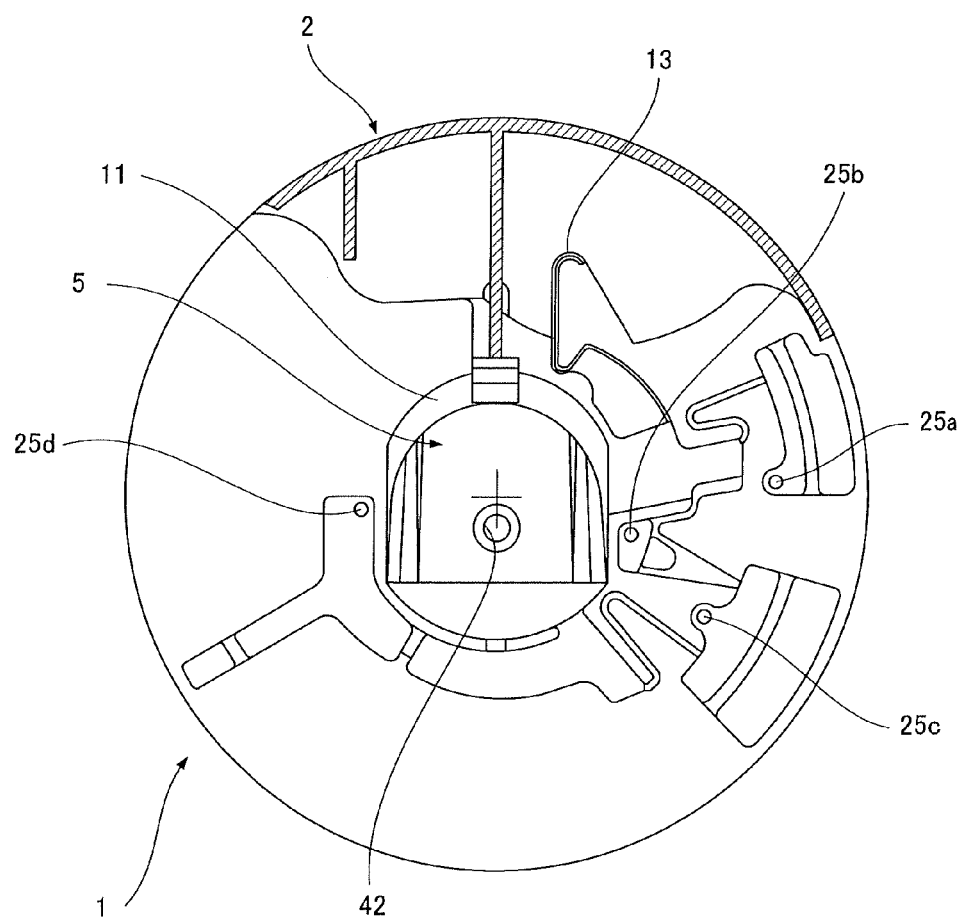
FIG. 11 is a cross-sectional view taken after setting an analysis device on an analysis apparatus and before starting rotation.

Due to such a configuration, when spot-applied to the inlet 13, the sample liquid 18 is retrieved by the capillary cavity 19 via the guide section 17. FIG. 11 illustrates a state of the analysis device 1 set on the rotor 101 after spot application and before rotation. At this point, as described with reference to FIG. 6C, the aluminum seal 9 of the diluent container 5 has already collided with the opening rib 11a and has been broken. Reference characters 25a, 25b, 25c, and 25d denote air ducts formed on the base substrate 3.

Process 1

The analysis device 1 is set on the rotor 101 in a state where, as illustrated in FIG. 12A, a sample liquid is held in the capillary cavity 19 and the aluminum seal 9 of the diluent container 5 has been broken.

Process 2

When the rotor 101 is rotationally driven clockwise (direction depicted by C2) after closing the door 103, the held sample liquid is broken at the position of the bent section 22. A sample liquid inside the guide section 17 is discharged into the protective cap 2. The sample liquid 18 inside the capillary cavity 19 flows into the separation cavity 23 and is centrifugally separated in the separation cavity 23 into a blood plasma component 18a and a blood cell component 18b as illustrated in FIGS. 12B and 15A. The diluent 8 having flowed out from the diluent container 5 flows into a holding cavity 27 via discharge channels 26a and 26b. When the diluent 8 having flowed into the holding cavity 27 exceeds a predetermined amount, a surplus of the diluent 8 flows into an overflow cavity 29 via an overflow channel 28 and further flows into a reference measurement chamber 31 via a rib 30 for preventing reflux.

Figure 13:
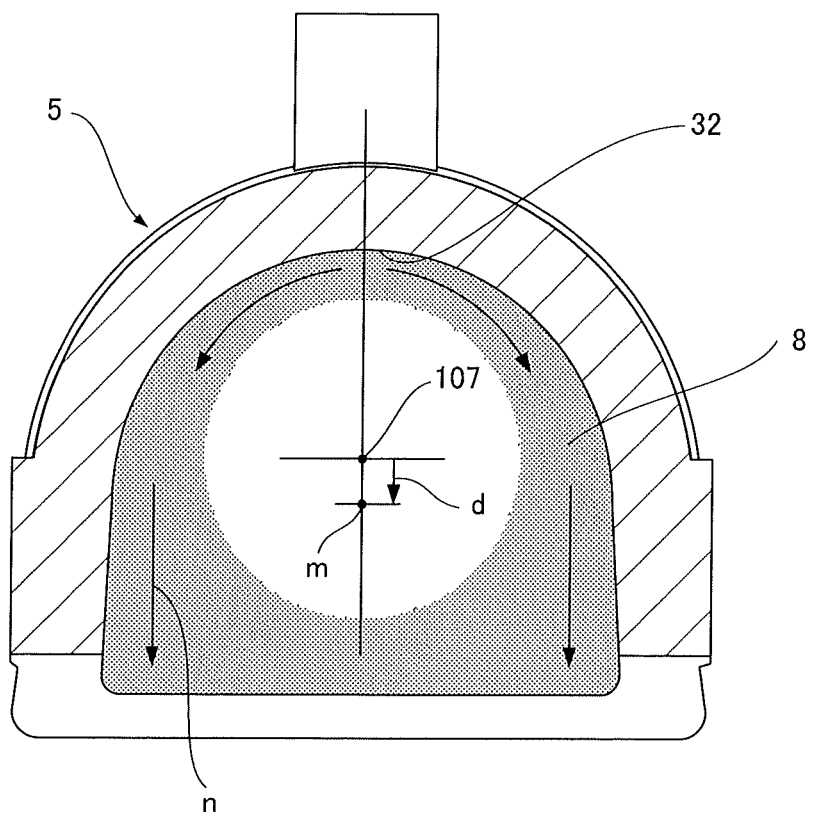
FIG. 13 is an enlarged cross-sectional view illustrating an axial center of rotation of an analysis device and a position of a diluent container at a timing where a diluent is discharged from the diluent container.

With respect to the diluent container 5, the shape of a bottom on the opposite side to the opening 7 sealed by the aluminum seal 9 is formed by an arc face 32 as illustrated in FIGS. 4A and 4B. At the same time, at the liquid discharge position of the diluent container 5 illustrated in FIG. 12B, the arc face 32 is formed offset by a distance d so that a center m of the arc face 32 becomes closer to a side of the discharge channel 26b than the axial center 107 as illustrated in FIG. 13. Consequently, the diluent 8 having flowed towards the arc face 32 is changed so as to flow along the arc face 32 and towards the opening 7 from the outside (direction depicted by arrow n), and is efficiently discharged from the opening 7 of the diluent container 5 to the diluent container containing section 11.

Process 3

Next, when the rotation of the rotor 101 is stopped, the blood plasma component 18a is siphoned by a capillary cavity 33 formed on a wall face of the separation cavity 23 and then flows into a measurement channel 38 via a capillary channel 37 that communicates with the capillary cavity 33 as illustrated in FIGS. 14A and 15B, and a fixed quantity is retained. FIG. 15C is a perspective view illustrating the capillary cavity 33 and a vicinity of the same.

Process 4

When the rotor 101 is rotationally driven counter-clockwise (direction depicted by C1), as illustrated in FIG. 14B, the blood plasma component 18a held in the measurement channel 38 flows into a measurement chamber 40 via a reflux-preventing rib 39. In addition, the diluent 8 in the holding cavity 27 flows into the measurement chamber 40 via a siphon-shaped connecting channel 41 and the reflux-preventing rib 39. Furthermore, a sample liquid in the separation cavity 23 flows into an overflow cavity 36 via a siphon-shaped connecting channel 34 and a reflux-preventing rib 35. Subsequently, as necessary, the rotor 101 is reciprocatively rotationally moved counter-clockwise (direction depicted by C1) and clockwise (direction depicted by C2) in a swinging motion to agitate a measurement object solution made up of a reagent, the diluent 8, and the blood plasma component 18a held in the measurement chamber.

Process 5

The rotor 101 is rotated counter-clockwise (direction depicted by C1) or clockwise (direction depicted by C2). A reference value is determined when the computing section 110 reads a detected value of the photodetector 113 at a timing where a measurement spot of the reference measurement chamber 31 passes between the light source 112 and the photodetector 113. Furthermore, the computing section 110 reads a detected value of the photodetector 113 at a timing where a measurement spot of the measurement chamber 40 passes between the light source 112 and the photodetector 113 to calculate a specific component based on the reference value.

As seen, since a user can open the diluent container 5 and transfer a diluted liquid into the analysis device 1 by an opening/closing operation of the protective cap 2 when collecting a sample liquid, an analysis apparatus can be simplified, cost can be reduced, and user operability can be improved.

Furthermore, since the diluent container 5 sealed by the aluminum seal 9 as a seal member is used and the diluent container 5 is opened by breaking the aluminum seal 9 with the opening rib 11a as a protrusion, a diluent does not evaporate and decrease even during long-term preservation, thereby enabling improvement in analytical precision to be realized.

Moreover, in a shipping state of the analysis device 1 illustrated in FIG. 6A, the latch 10 of the diluent container 5 engages the locking groove 12 of the closed protective cap 2 and the diluent container 5 is locked at the liquid holding position and prevented from moving in the direction of arrow J. Although the diluent container 5 is arranged so as to be movable in the diluent container containing section 11 by an opening/closing operation of the protective cap 2, the position of the diluent container 5 at the diluent container containing section 11 is locked at the liquid holding position until the user opens the protective cap 2 to use the diluent container 5. As a result, an accidental opening of the diluent container 5 and spillage of the diluent during transport by the user prior to use can be prevented.

Figure 16:
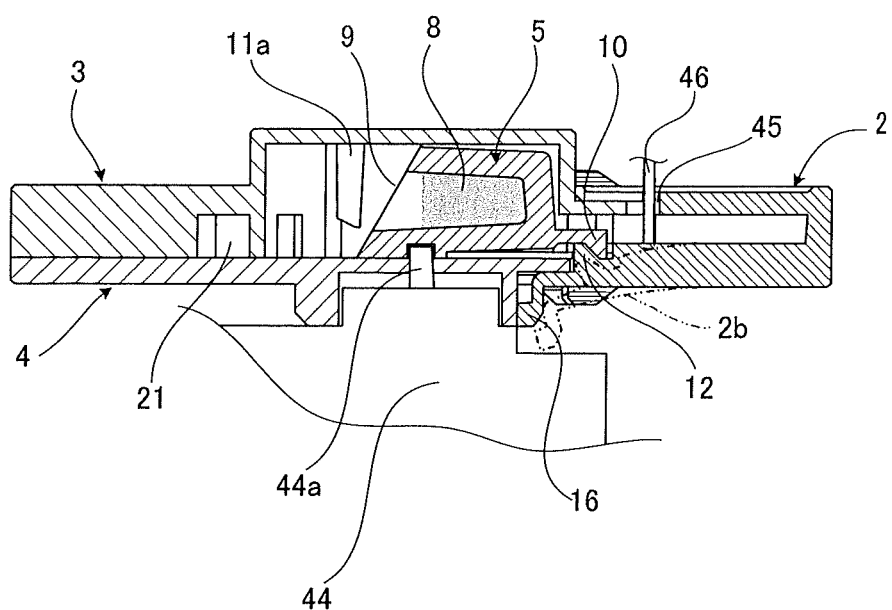
FIG. 16 is a cross-sectional view of a process for setting to a shipping state.

FIG. 16 illustrates a manufacturing process in which the analysis device 1 is set to the shipping state illustrated in FIG. 6A. First, before closing the protective cap 2, a groove 42 (refer to FIGS. 2B and 4D) provided on a lower face of the diluent container 5 and a hole 43 provided on the cover substrate 4 are aligned. At this liquid holding position, a protrusion 44a of a locking jig 44 provided separate from the base substrate 3 or the cover substrate 4 is brought into engagement with the groove 42 of the diluent container 5 through the hole 43, thereby setting the diluent container 5 in a state where the diluent container 5 is locked at the liquid holding position. Subsequently, a pressing jig 46 is inserted through a notch 45 (refer to FIG. 1) formed on an upper face of the protective cap 2 so as to press the bottom face of the protective cap 2 to cause elastic deformation. In this elastically deformed state, the analysis device 1 can be set to the state illustrated in FIG. 6A by closing the protective cap 2 and then releasing the pressing jig 46.

In the present embodiment, a case where the groove 42 is provided on a lower face of the diluent container 5 has been described as an example. Alternatively, the groove 42 may be provided on an upper face of the diluent container 5, and the hole 43 may be provided on the base substrate 3 so as to correspond to the groove 42, whereby the protrusion 44a of the locking jig 44 is to be brought into engagement with the groove 42.

In the embodiment described above, the locking groove 12 of the protective cap 2 directly engages the latch 10 of the diluent container 5 to lock the diluent container 5 at the liquid holding position. Alternatively, the diluent container 5 may be locked at the liquid holding position by having the locking groove 12 of the protective cap 2 and the latch 10 of the diluent container 5 indirectly engage each other.

In the embodiment presented above, a case has been described as an example in which a component centrifugally separated from a sample liquid by rotating the analysis device 1 around the rotation axial center 107 and the diluent 8 discharged from the diluent container 5 are transferred to the measurement chamber 40 to be diluted, whereby analysis is performed by accessing a solution component separated from a sample liquid or a reactant of a solution component separated from a sample liquid and a reagent. However, when a solution component need not be separated from a sample liquid, the separation process is no longer required. In this case, the analysis device 1 is rotated around the rotation axial center 107 to transfer all of a fixed amount of a sample liquid among a spot-applied sample liquid and the diluent 8 discharged from the diluent container 5 to the measurement chamber 40 to be diluted, whereby analysis is performed by accessing a solution component diluted by the diluent or a reactant of a solution component diluted by the diluent and a reagent.

Alternatively, the analysis device 1 may be rotated around the rotation axial center 107 to transfer a solid component separated from a sample liquid and a diluent discharged from the diluent container 5 to the measurement chamber to be diluted, whereby analysis may be performed by accessing the solid component separated from the sample liquid or a reactant of the solid component separated from the sample liquid and a reagent.

In the embodiment described above, an analysis device main body having, formed inside, a microchannel structure with minute surface irregularities is structured with two layers, namely, the base substrate 3 and the cover substrate 4. Alternatively, the analysis device main body may be structured by pasting together three or more substrates. Conceivable specific examples include a three-layer structure that is a microchannel structure formed by setting a substrate notched according to a microchannel structure at center, pasting separate substrates on an upper face and a lower face of the central substrate, and closing the notches.

In FIG. 8, the set analysis device 1 is merely pushed to a side of the rotor 101 by the spring 105 set between the door 103 and the movable piece 104. Therefore, there is a risk that the analysis device 1 may become detached from the rotor 101 when an external force acting during operation causes an uplift of the analysis device 1 beyond a permissible value. According to second to seventh embodiments described below, situations where the analysis device 1 detaches from the rotor 101 can be avoided.

Second Embodiment

FIGS. 17 to 19A and 19B illustrate a second embodiment of the present invention.

FIGS. 17 to 19A and 19B illustrate an analysis apparatus including an analysis device driving apparatus according to the present invention.

Figure 17:
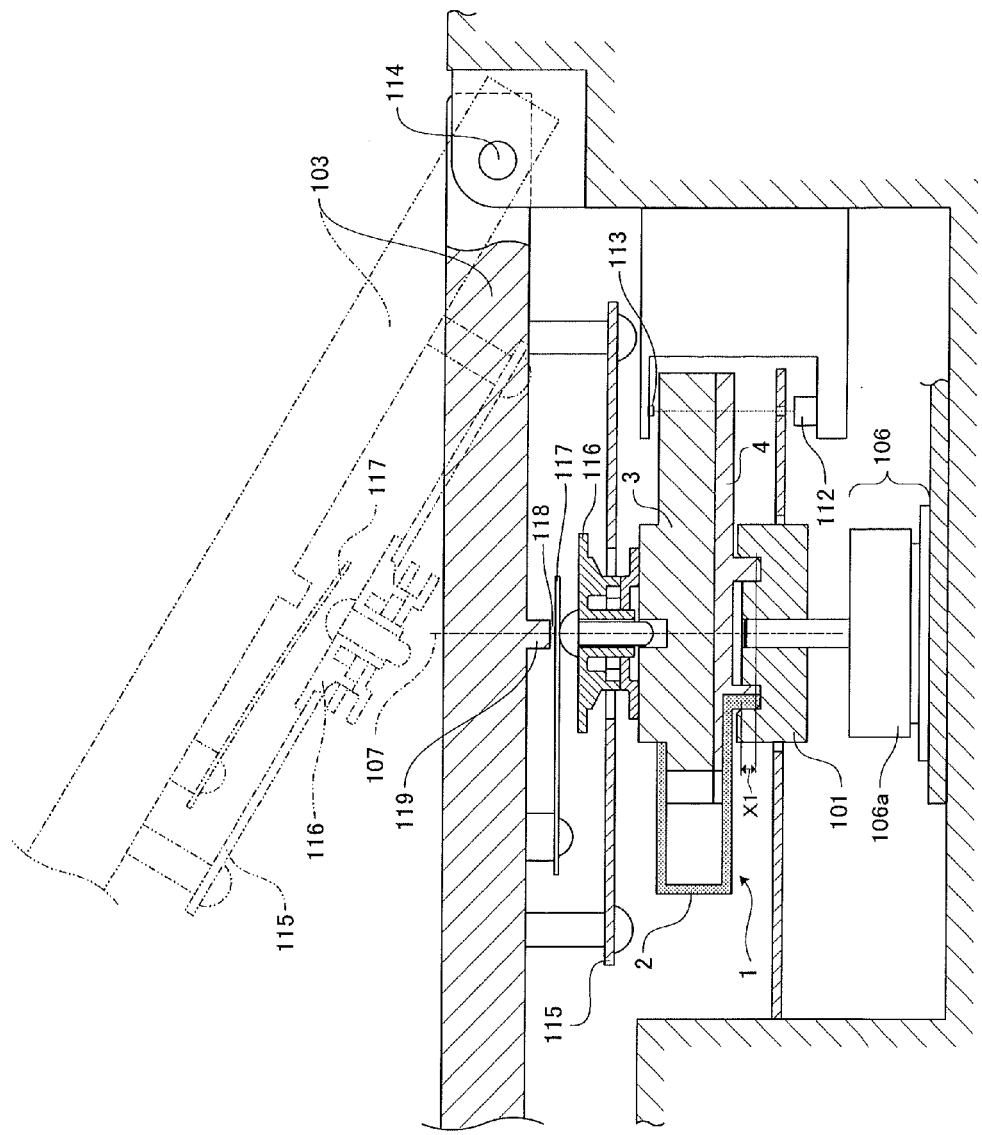
FIG. 17 is a cross-sectional view of a state where an analysis device is set in an analysis apparatus according to a second embodiment of the present invention.

FIG. 17 illustrates a state where an analysis device 1 according to an embodiment of the present invention is set on a rotor 101 of an analysis device driving apparatus of an analysis apparatus. FIGS. 1A and 1B respectively illustrate a closed state and an opened state of a protective cap 2 of the analysis device 1. FIG. 2 illustrates an exploded state where a face of the analysis device 1 in contact with the rotor 101 is faced upwards. FIG. 3 is a perspective view as seen from behind of the analysis device in a state where the protective cap 2 is closed.

The analysis device 1 is made up of parts including: a protective cap 2 for preventing scattering of a sample liquid; a base substrate 3 on which is formed a microchannel structure having minute irregularities on a surface thereof; a cover substrate 4 covering a surface of the base substrate 3; and a diluent container 5 holding a diluent.

The base substrate 3 and the cover substrate 4 are bonded in a state where the diluent container 5 and the like are internally set, whereby the protective cap 2 is attached to the base substrate 3 and the cover substrate 4 in the bonded state. One side of the protective cap 2 is pivotally supported so as to be capable of engaging shafts 6a and 6b formed on the base substrate 3 and the cover substrate 4 and to be openable and closable.

By covering the openings of several depressions formed on the upper face of the base substrate 3 with the cover substrate 4, a plurality of containment areas and channels interconnecting the containment areas are formed (refer to FIG. 2). Among the containment areas, those required hold, in advance, reagents necessary for performing various analyses.

The analysis device 1 is capable of collecting a sample liquid such as blood and other solutions from an inlet 13, and by closing the protective cap 2 and setting the sample liquid on the rotor 101 of the analysis apparatus, a component analysis of the sample liquid can be performed. Reference numeral 107 denotes an axial center during rotation of the rotor 101.

The analysis device 1 is arranged so as to internally transfer a sample liquid or a solution taken inside from the inlet 13 by a centrifugal force that is generated by rotating the analysis device 1 around the axial center 107 positioned circumferentially inward from the inlet 13 and by a capillary force of a capillary channel provided inside the analysis device 1. The protective cap 2 is attached in order to prevent the sample liquid adherent to a vicinity of the inlet 13 from scattering to the outside due to centrifugal force during analysis.

Since the aforementioned analysis apparatus analyzes sample liquids using an optical measurement method in which light transmitted through the analysis device 1 is measured, a resin with a high transparency such as PC, PMMA, AS, MS, and the like is desirably used as the material for the base substrate 3 and the cover substrate 4.

Bonding between the base substrate 3 and the cover substrate 4 is desirably performed using a method that is unlikely to affect the reaction activity of reagents held in the containment areas. Desirable methods include ultrasonic welding and laser welding which are less likely to create reactive gases or solvents during bonding.

Figure 18:
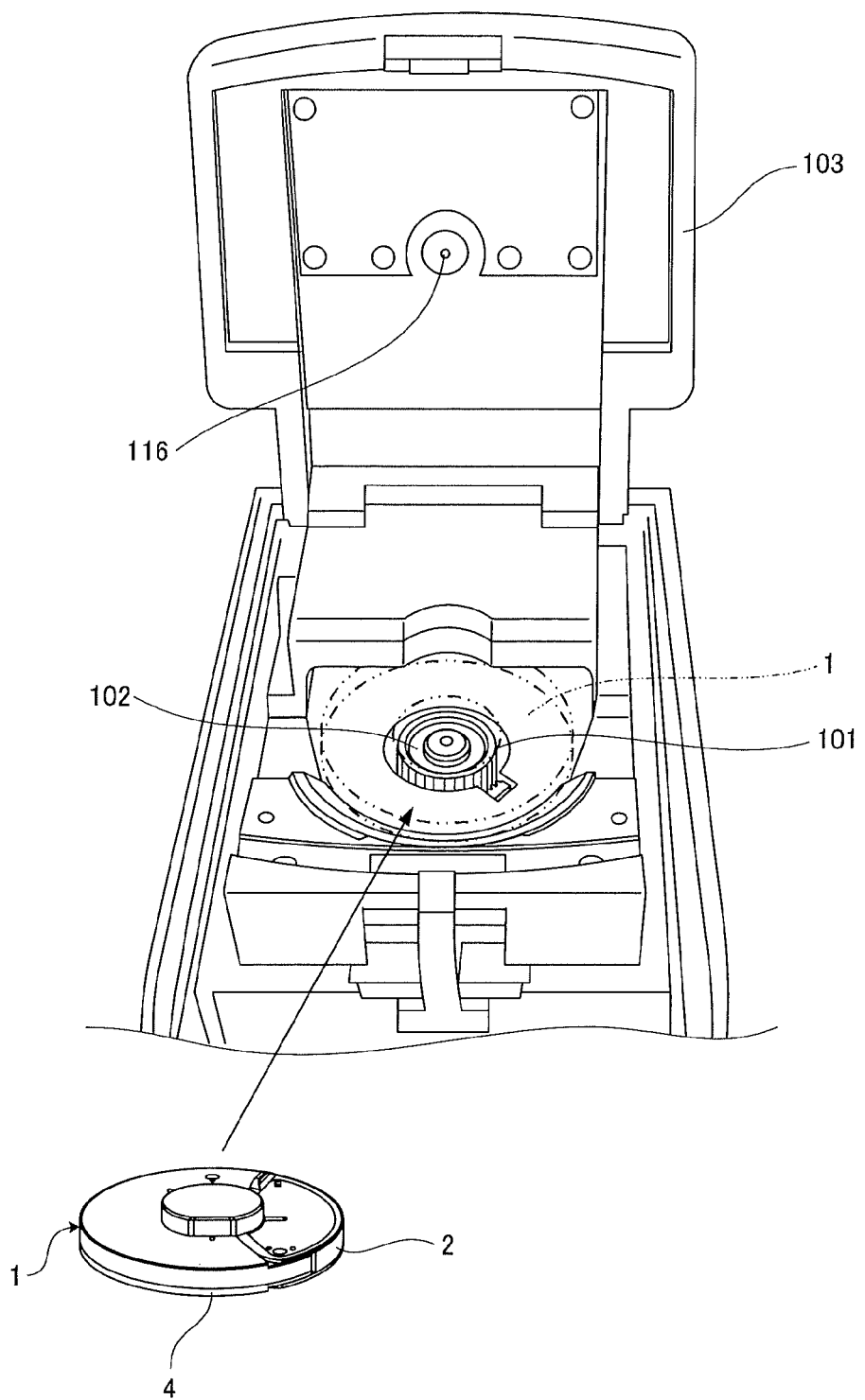
FIG. 18 is a perspective view of a state where a door of an analysis apparatus according to the second embodiment of the present invention has been opened.

FIG. 18 is a more detailed external view of the analysis apparatus illustrated in FIG. 7 and illustrates a state where the door 103 has been opened and the rotor 101 has been exposed so as to enable the analysis device 1 to be set. FIG. 17 is a cross-sectional view of FIG. 18. The door 103 rotationally moves around a support shaft 114 and is openable and closable.

In this case, a motor 106a is used as a rotation driving unit 106 to rotate the rotor 101 around the axial center 107.

While an arrangement is provided in which rotational operations and swinging operations of the analysis device 1 are performed by a single rotation driving unit 106, a driving unit for swinging operations may be separately provided in order to reduce the load on the rotation driving unit 106. Specifically, by bringing a vibration-applying unit such as a vibration motor prepared separate from the motor 106a into direct or indirect contact with the analysis device 1 set on the rotor 101, the analysis device 1 is subjected to a swinging motion so as to apply inertial force to the solution in the analysis device 1.

A clamper 116 is held by the door 103 via a holding plate 115. In addition, a flat spring 117 as a biasing unit for pressing the clamper 116 is provided on the door 103. After setting the analysis device 1 on the rotor 101, when the door 103 of the analysis apparatus is closed as depicted by a solid line in FIG. 17 before rotating the rotor 101, the flat spring 117 comes into contact with the clamper 116 on the axis of the rotation axial center 107 of the rotor 101, the clamper 116 is pressed to a side of the rotor 101 by a biasing force of the flat spring 117, the analysis device 1 is sandwiched by the clamper 116 and the rotor 101, and the rotor 101 rotates at high-speed integrally with the analysis device 1.

At this point, if X1 denotes an engagement depth of a groove 102 of the rotor 101 and an engaging section 15 of the analysis device 1, the analysis device 1 being rotationally driven at high speed is biased to a side of the rotor 101 by the biasing force of the flat spring 117 so as to prevent uplift of the analysis device 1 from the rotor 101 beyond X1. Furthermore, in the present embodiment, a protrusion 119 that sets a gap 118 between the door 103 and the flat spring 117 at a position on the axial center 107 to or below X1 is formed on an inner face of the door 103.

As shown, the protrusion 119 as a stopper unit on the door 103 is arranged so as to oppose the flat spring 117, with the gap 118 provided between the protrusion 119 and the flat spring 117. Therefore, when an appropriate biasing force is being obtained from the flat spring 117, the protrusion 119 and the flat spring 117 do not come into contact with each other and the clamper 116, being only in point contact with the flat spring 117 on the axial center 107, rotates at high speed.

On the other hand, even when an external force acts during operation and the analysis device 1 attempts to uplift from the rotor 101 beyond X1 that is a permissible value, the clamper 116 abuts to the protrusion 119 via the flat spring 117 and reliably regulates the analysis device 1 from detaching from the rotor 101. In this case, contact points between the flat spring 117 and the protrusion 119 are limited to only the point contact on the axial center 107. Therefore, a stable operation can be expected over a long period of time.

Moreover, by arranging the holding plate 115 disposed opposing the set analysis device 1 as a heater plate that is heated when receiving power or by indirectly heating the holding plate 115 with a heater, a reduction in analysis time can be realized. At the same time, since the need to dispose a heating unit at a separate location can be eliminated, downsizing of an analysis apparatus can be realized.

X1 described above will now be explained in greater detail with reference to FIGS. 19A and 19B.

Figure 19A:
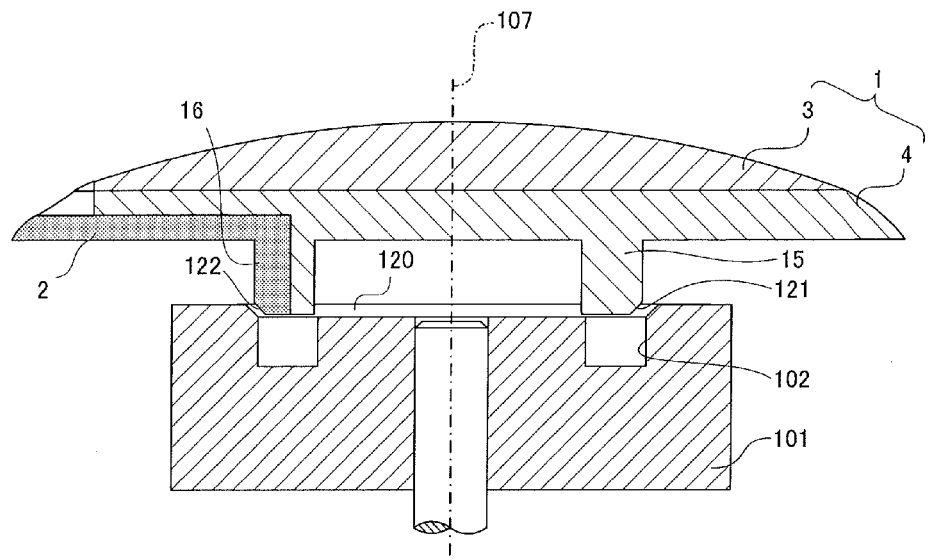
FIG. 19A is an enlarged cross-sectional view taken immediately before setting an analysis device onto a rotor.

FIG. 19A illustrates a state immediately before mounting the analysis device 1 on the rotor 101. In order to enable the analysis device 1 to be easily set in a groove 102 of the rotor 101, an inclined face 120 inclined such that a major axis thereof is oriented circumferentially outward is formed at an opening of the groove 102 formed on the rotor 101, and an engaging section 15 of the cover substrate 4 of the analysis device 1 and an engaging section 16 formed on the protective cap 2 are respectively processed into chamfered sections 121 and 122 so as to remove circumferentially outermost corners of the engaging section 15 and the engaging section 16.

Figure 19B:
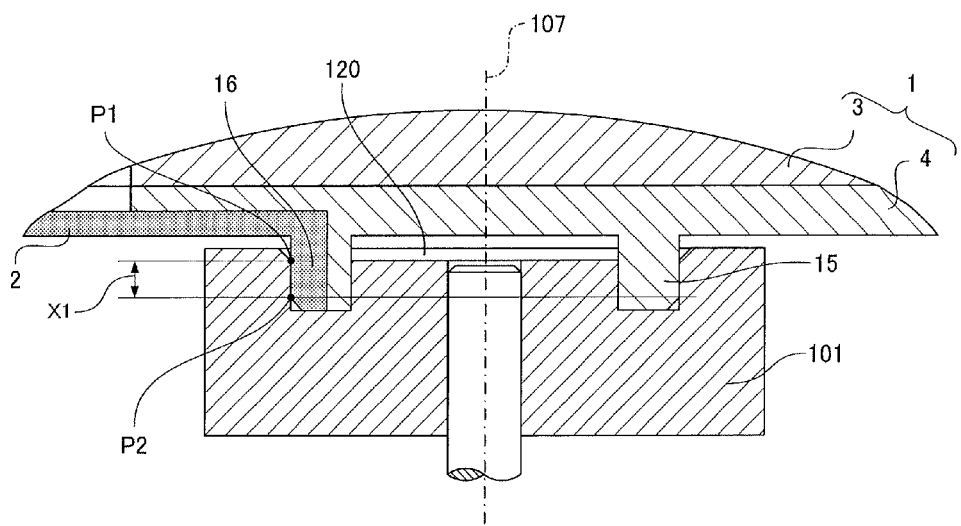
FIG. 19B is an enlarged cross-sectional view of a state where an analysis device has been set on a rotor.

Even when the analysis device 1 is set from a position slightly laterally offset with respect to the groove 102 of the rotor 101, the chamfered sections 121 and 122 of the analysis device 1 abut to the inclined face 120 of the rotor 101, and the engaging sections 15 and 16 of the analysis device 1 are guided by the inclined face 120 of the rotor 101 to engage the groove 102 as illustrated in FIG. 19B.

In this case, aforementioned X1 denotes a distance between a position P1 of a smallest diameter of the inclined face 120 of the rotor 101 and a proximal end position P2 of the chamfered sections 121 and 122 of the analysis device 1. In a state where an external force acts during operation and the analysis device 1 uplifts from the rotor 101 by X1, the chamfered sections 121 and 122 of the analysis device 1 run on the inclined face 120 of the rotor 101, resulting in a situation where the analysis device 1 becomes detached from the rotor 101 due to centrifugal force. Therefore, the clamper 116 must be maintained so that the clamper 116 does not uplift from the rotor 101 beyond the permissible value X1 against the biasing force of the flat spring 117.

Third Embodiment

In the second embodiment, a protrusion 119 as a stopper unit is formed on the door 103 in order to regulate an uplift of the analysis device 1 from the rotor 101. In a third embodiment illustrated in FIG. 20, a gap 123 between an opposing face 115A of a holding plate 115 which opposes a clamper 116 and the clamper 116 is set smaller than a permissible value X1. Otherwise, the configuration is the same as the configuration of the second embodiment illustrated in FIG. 17.

A hole 115B that is smaller in diameter than a large diameter section 116A and a small diameter section 116B of the clamper 116 is formed at the center of the holding plate 115. The clamper 116 is supported by inserting a body section 116C between the large diameter section 116A and the small diameter section 116B into the hole 115B.

Fourth Embodiment

Figure 21:
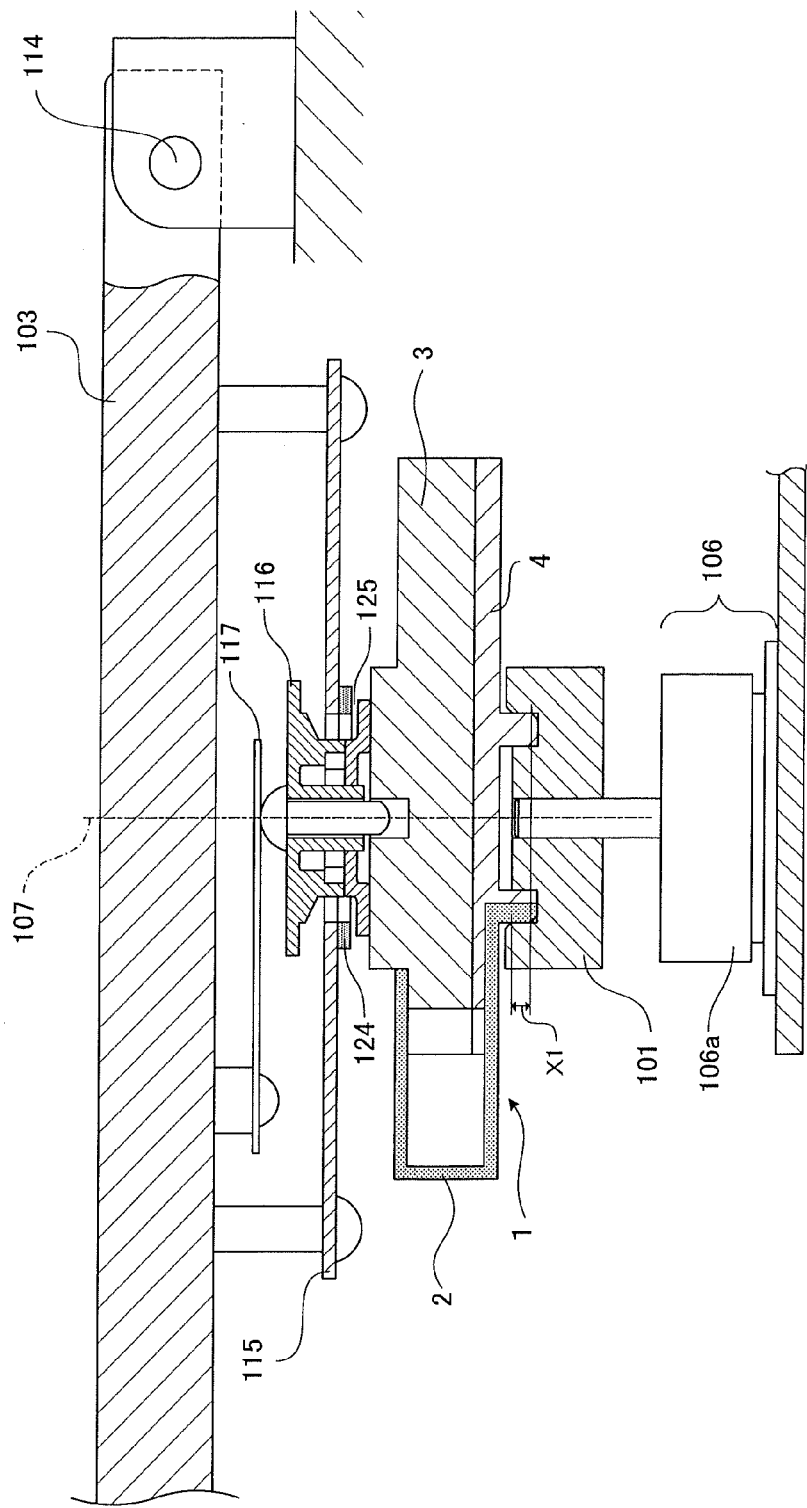
FIG. 21 is a cross-sectional view of a state where an analysis device is set in an analysis apparatus according to a fourth embodiment of the present invention.

In the third embodiment, the clamper 116 is directly abutted to a lower face of the holding plate 115 in order to regulate uplift of the analysis device 1 from the rotor 101 due to external force. However, in a fourth embodiment illustrated in FIG. 21, a protrusion 124 that protrudes towards a clamper 116 is formed around the hole 115B on a face of the holding plate 115 on a side of the rotor 101, and a gap 125 between the protrusion 124 and the clamper 116 is set smaller than a permissible value X1. Otherwise, the configuration is the same as the configuration of the second embodiment illustrated in FIG. 17.

Specifically, the protrusion 124 is formed by a material that is superior in friction and abrasion characteristics than the holding plate 115 such as POM (polyacetal) and nylon.

Fifth Embodiment

Figure 22:
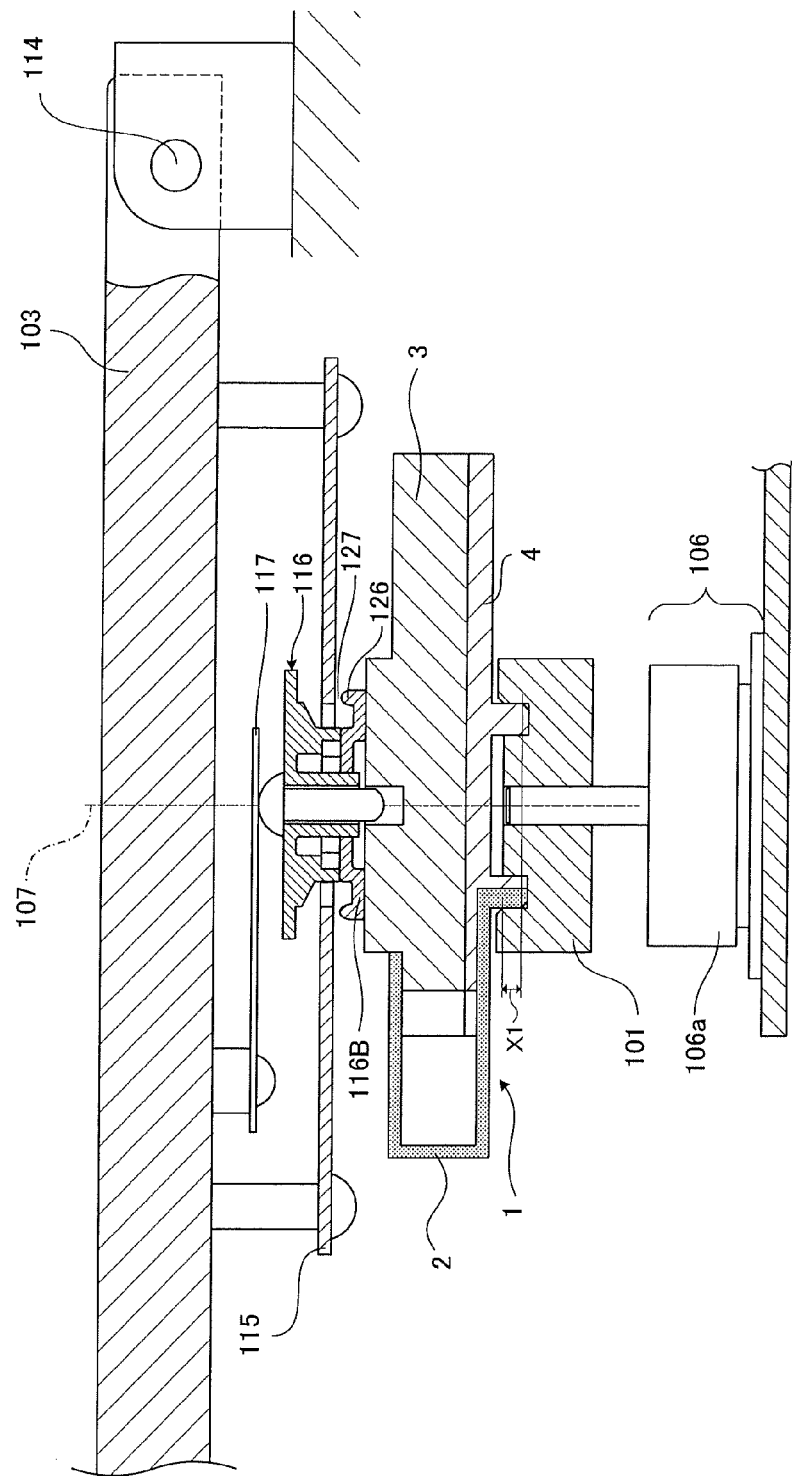
FIG. 22 is a cross-sectional view of a state where an analysis device is set in an analysis apparatus according to a fifth embodiment of the present invention.

In the third embodiment, the clamper 116 is directly abutted to a lower face of the holding plate 115 in order to regulate uplift of the analysis device 1 from the rotor 101 due to external force. However, in a fifth embodiment illustrated in FIG. 22, a protrusion 126 is formed on an opposing face of a small diameter section 116B of a clamper 116 which opposes the holding plate 115, and a gap 127 between the protrusion 126 and the holding plate 115 is set smaller than a permissible value X1. Otherwise, the configuration is the same as the configuration of the second embodiment illustrated in FIG. 17.

Specifically, the protrusion 126 is formed integrally with the small diameter section 116B by a material that is superior in friction and abrasion characteristics than the holding plate 115 such as POM (polyacetal) and nylon.

Sixth Embodiment

While the biasing unit in the respective embodiments described above is the flat spring 117, a coil spring can be used instead.

Figure 20:
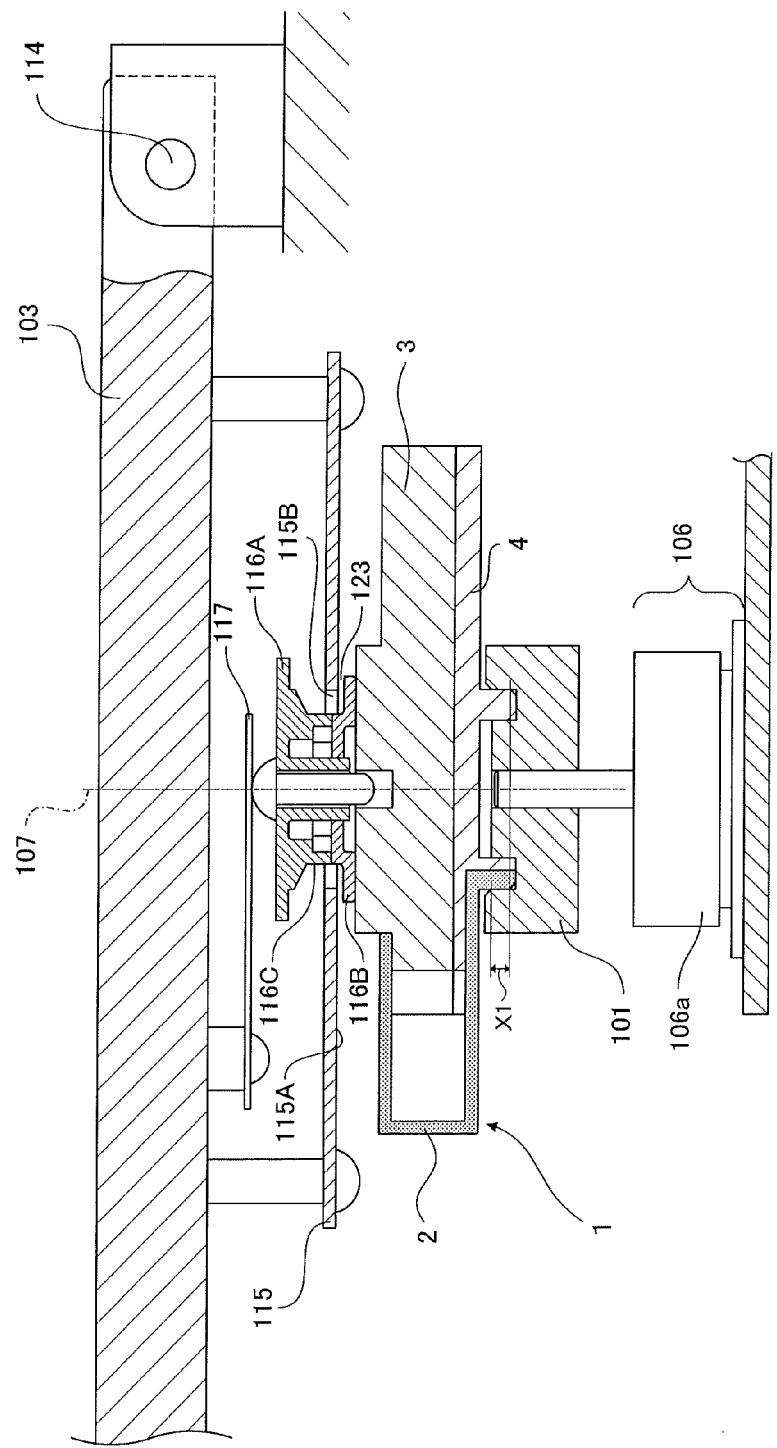
FIG. 20 is a cross-sectional view of a state where an analysis device is set in an analysis apparatus according to a third embodiment of the present invention.
Figure 23:
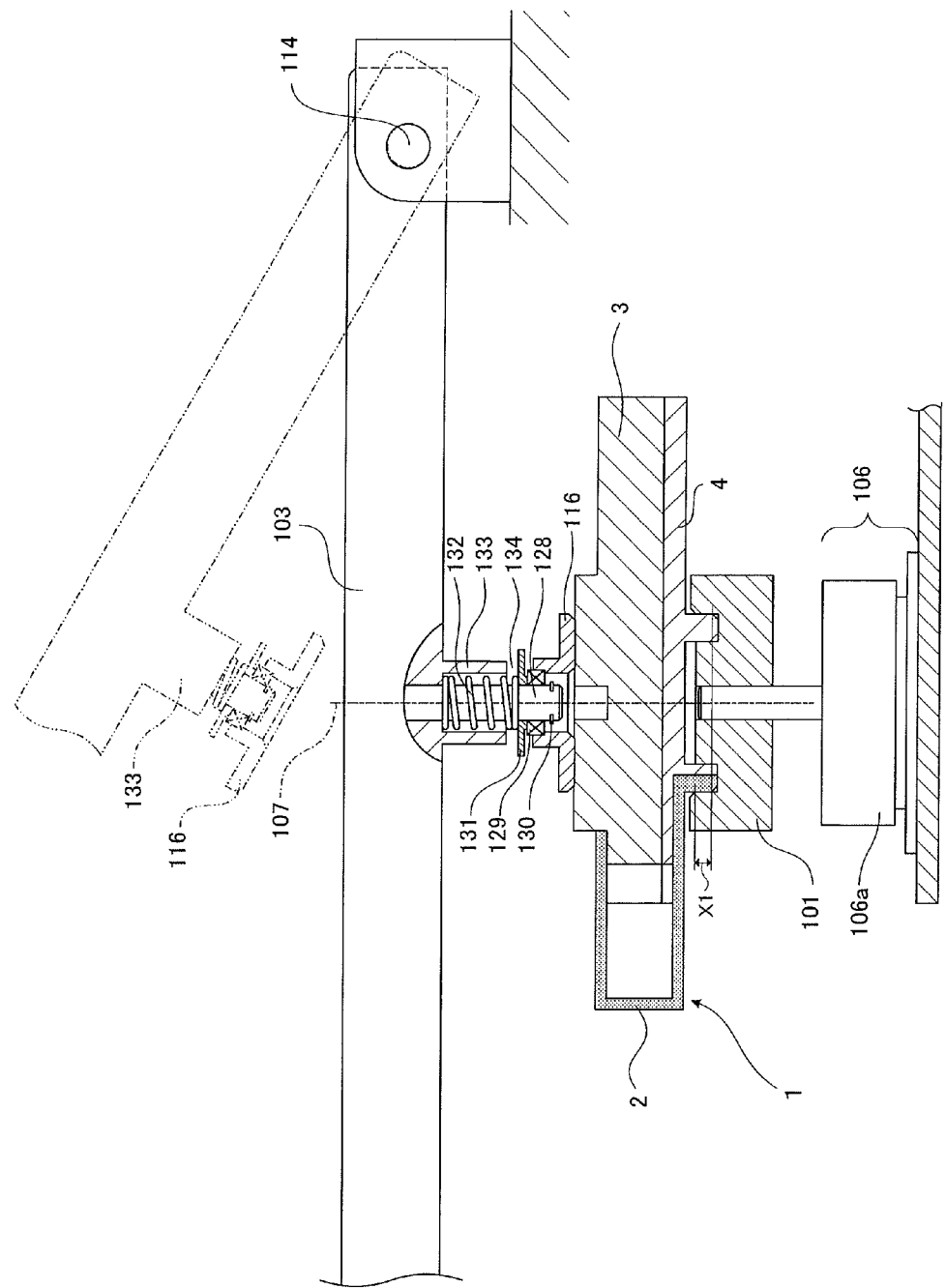
FIG. 23 is a cross-sectional view of a state where an analysis device is set in an analysis apparatus according to a sixth embodiment of the present invention.

FIG. 23 illustrates a modification of FIG. 20. A description will now be given, wherein parts similar to preceding embodiments are assigned similar reference characters.

In the present sixth embodiment, a clamper 116 is fixed via a bearing 129 to a tip of a shaft 128 implanted on a door 103. Reference numeral 130 denotes a retaining ring provided so as to prevent the bearing 129 from dropping off from the shaft 128. A coil spring 132 is set between the door 103 and a washer 131 whose one face touches an inner circumferential side of the bearing 129. In a state where the door 103 is opened to a position depicted by an imaginary line, the clamper 116 is pushed against the ring 130 on the tip of the shaft 128 by the coil spring 132. The shaft 128 is inserted through an inner side of the coil spring 132.

In a state where the door 103 is closed to a position depicted by a solid line and the analysis device 1 is sandwiched by the rotor 101 and the clamper 116, the bearing 129 is separated from the ring 130 against the biasing of the coil spring 132. Therefore, the clamper 116 is pressed against the analysis device 1 set on the rotor 101 by the biasing force of the coil spring 132 and held in this state.

On the other hand, even when the analysis device 1 attempts to uplift itself from the rotor 101 by more than X1 that is a permissible value, since a gap 134 between a protrusion 133 integrally formed with the door 103 and the washer 131 during normal operation is set smaller than the permissible value X1, the washer 131 strikes the protrusion 133 of the door 103 first when the analysis device 1 uplifts from the rotor 101 due to an action of an external force during operation. As a result, a situation such as the analysis device 1 detaching itself from the rotor 101 can be avoided. The protrusion 133 is formed on the door 103 so as to surround the shaft 128.

Seventh Embodiment

Figure 24:
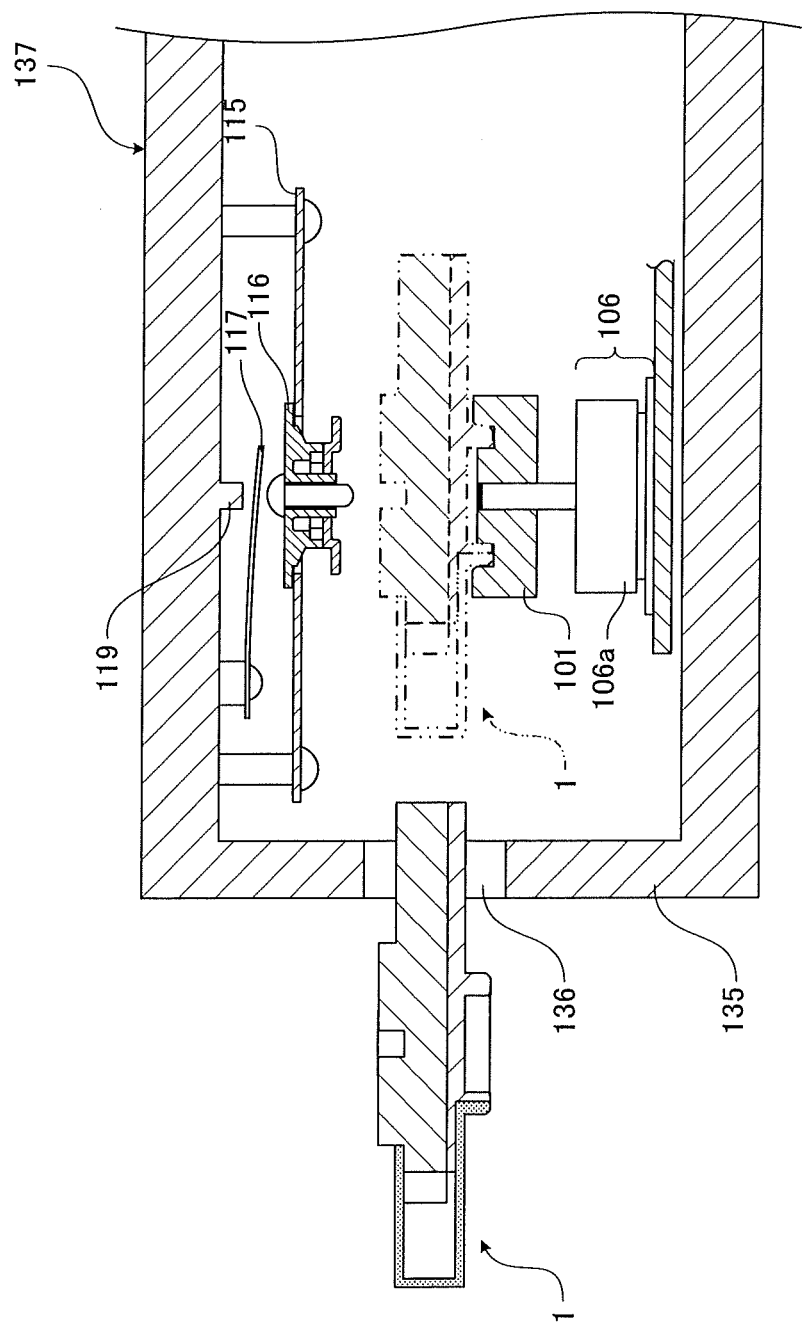
FIG. 24 is a cross-sectional view of a state where a leading end of an analysis device is inserted into an insertion opening of an analysis apparatus according to a seventh embodiment of the present invention.

In the respective embodiments described above, the door 103 is opened to mount the analysis device 1 on the rotor 101, and by closing the door 103 in this state, the analysis device 1 is sandwiched by the rotor 101 and the clamper 116. However, a case where the analysis device 1 is sandwiched by the rotor 101 and the clamper 116 by a central loading system as illustrated in FIGS. 24 and 25 can also be implemented.

In the present embodiment, when a leading end of the analysis device 1 is inserted into an insertion opening 136 formed on a front panel 135 of a chassis 137 of an analysis apparatus, a handling unit (not shown) having detected that the analysis device 1 has been inserted into the insertion opening 136 sets the analysis device 1 inserted into the insertion opening 136 on a rotor 101 that is standing by at a descended position.

A configuration of the handling unit is the same as the configurations of optical disk drive apparatuses that adopt a front loading system. More specifically, a configuration of this type is described in Japanese Patent Laid-Open No. 10-027407.

Figure 25A:
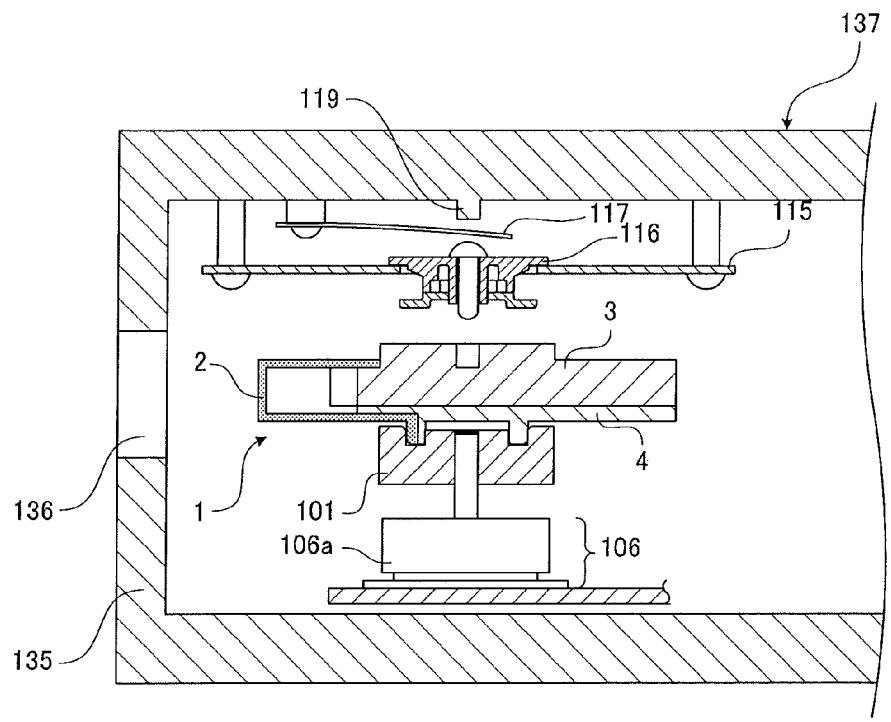
FIG. 25A is a cross-sectional view before a turntable rises in a process of sandwiching an analysis device according to the seventh embodiment of the present invention.
Figure 25B:
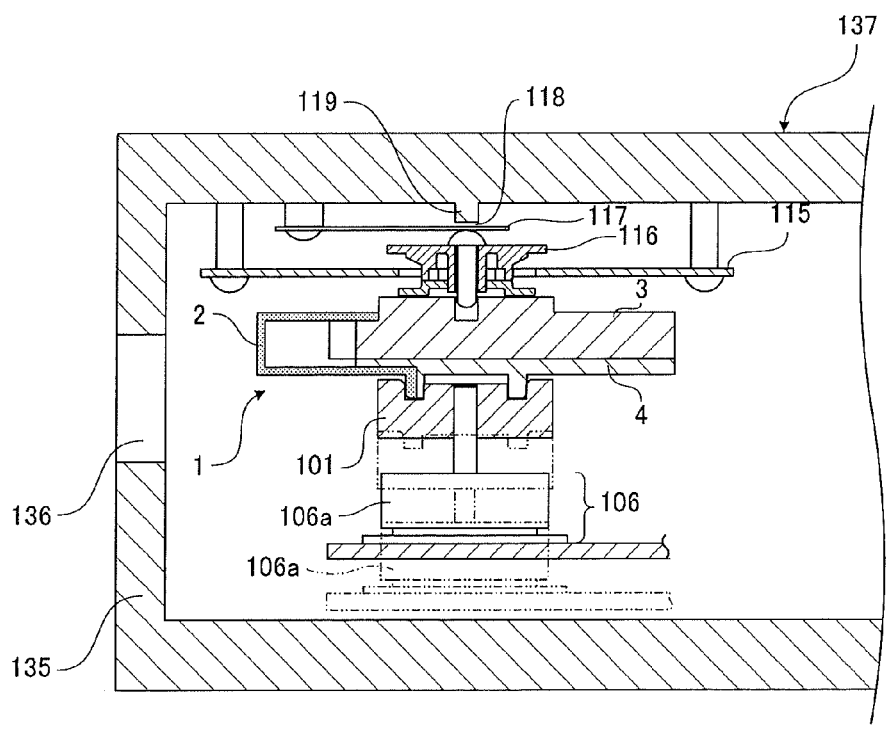
FIG. 25B is a cross-sectional view after a turntable rises in a process of sandwiching an analysis device according to the seventh embodiment of the present invention.
Figure 26:
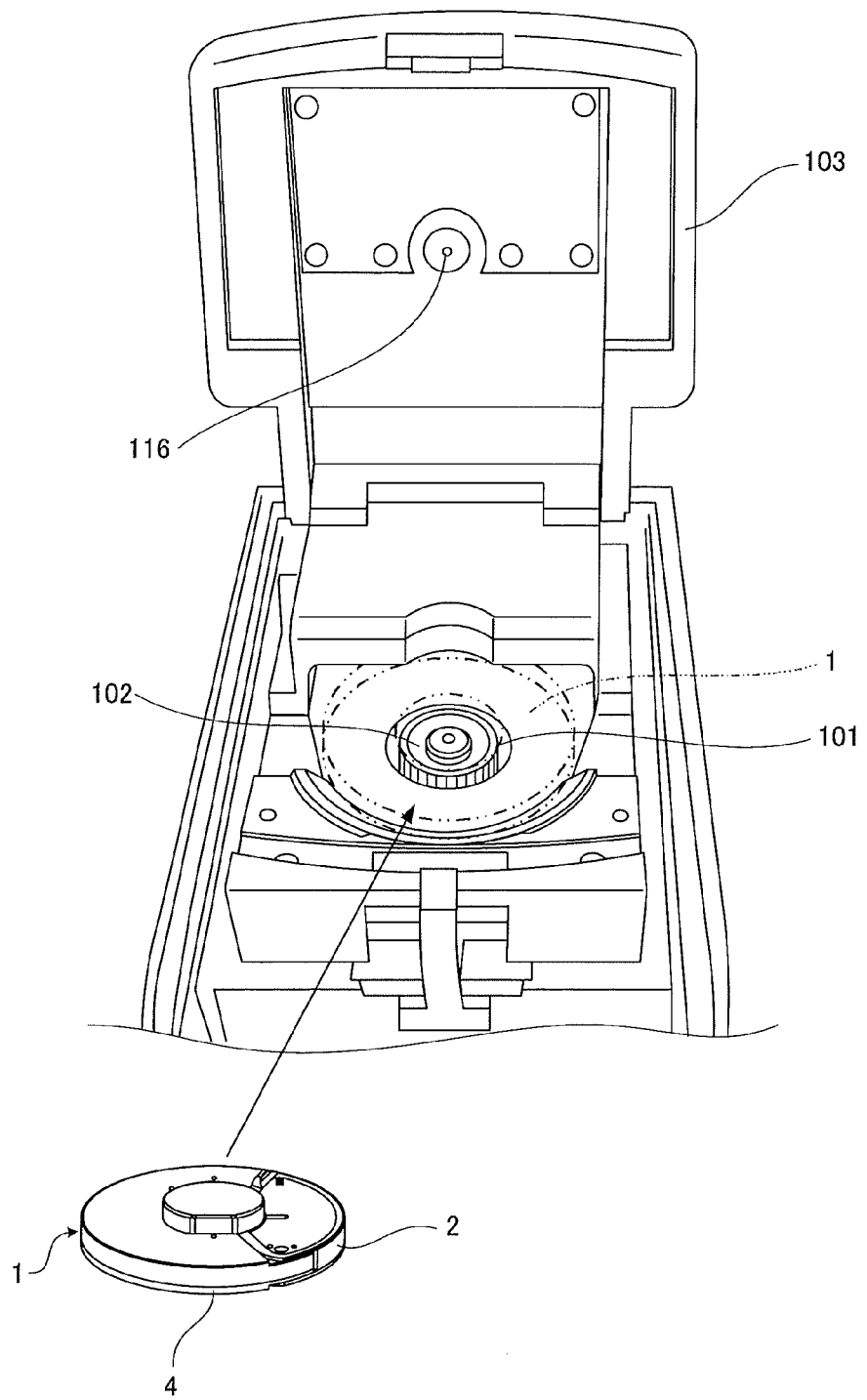
FIG. 26 is a perspective view of a state where a door of an analysis apparatus has been opened.
Figure 27:
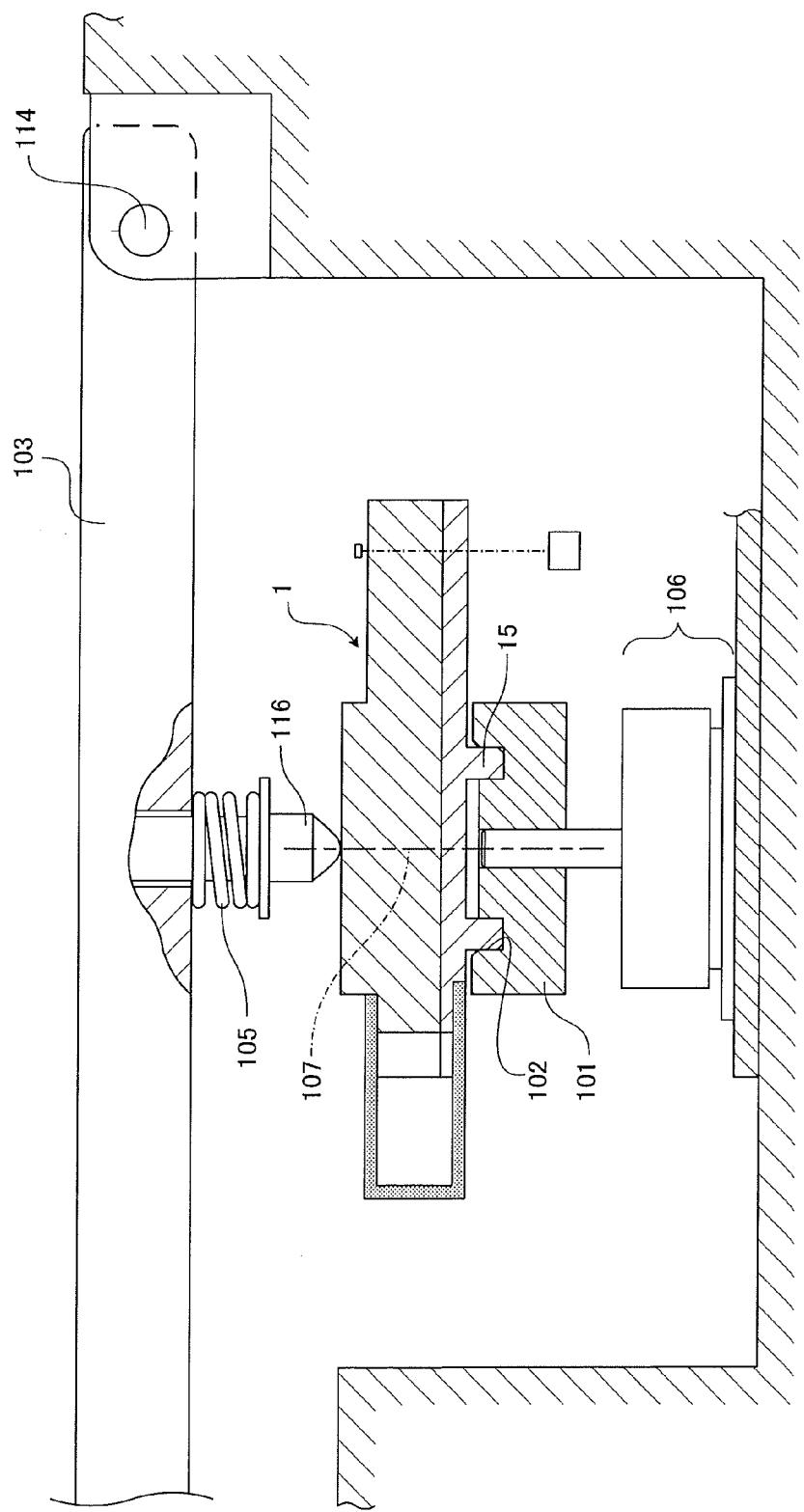
FIG. 27 is a cross-sectional view of a state where an analysis device has been set on an analysis device driving apparatus.

When the handling unit finishes setting the analysis device 1 on the rotor 101 as illustrated in FIG. 25A, the rotor 101 then rises as illustrated in FIG. 25B to sandwich the analysis device 1 with the clamper 116. Otherwise, the configuration is the same as the second embodiment.

Moreover, the third to sixth embodiments can also be implemented with a front loading system.

Furthermore, the analysis device 1 is desirably provided with a locking mechanism so as to prevent a protective cap 2 of the analysis device 1 during analysis from being opened due to centrifugal force or to prevent a protective cap 2 of a used analysis device 1 from being reopened. Specific examples thereof will now be described based on eighth to twelfth embodiments.

Eighth Embodiment

FIGS. 28 to 34 illustrate an eighth embodiment of the present invention.

A lidded container represents a case of an analysis device to be used for sampling a liquid considered to be an infectious material such as blood and setting the same on an analysis apparatus.

Figure 28:
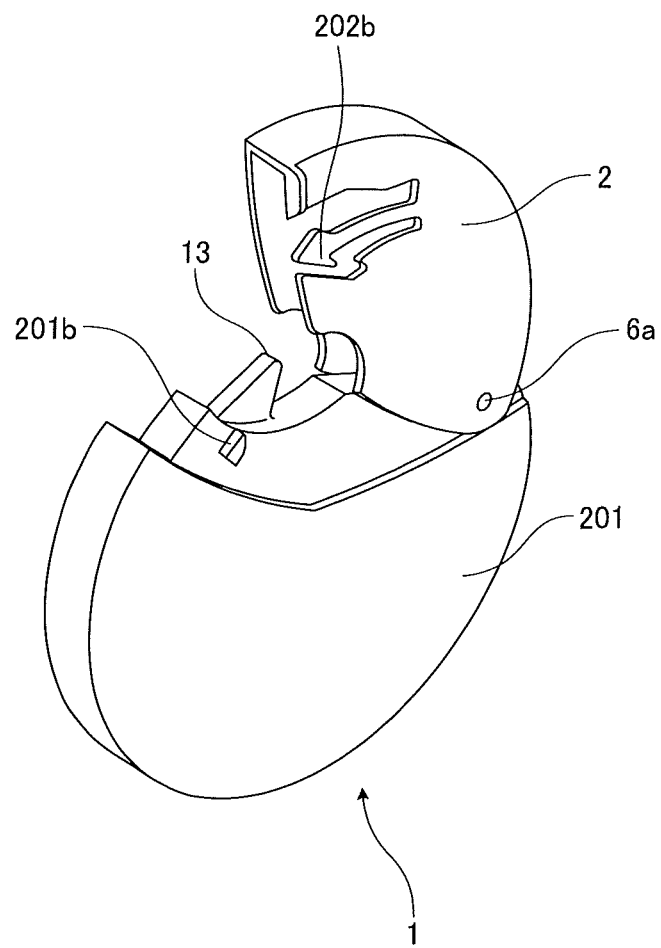
FIG. 28 is a perspective view of an in-use state in which a protective cap of a lidded container according to an eighth embodiment of the present invention has been opened.

FIG. 28 illustrates an analysis device 1 including a locking mechanism. In the analysis device 1, an end of a protective cap 2 as a lid member is pivotally supported by a shaft 6a so as to be rotationally movable between a position where an inlet 13 as a protection object location is exposed and a position where the inlet 13 is covered (refer to FIG. 31).

The analysis device 1 is supplied to a user with the protective cap 2 closed. At the beginning of use, the user opens the protective cap 2 as illustrated in FIG. 28, pierces a fingertip of a testee by a needle and spot-applies blood on the fingertip onto the inlet 13, and after spot application of blood, closes the protective cap 2.

Figure 29:
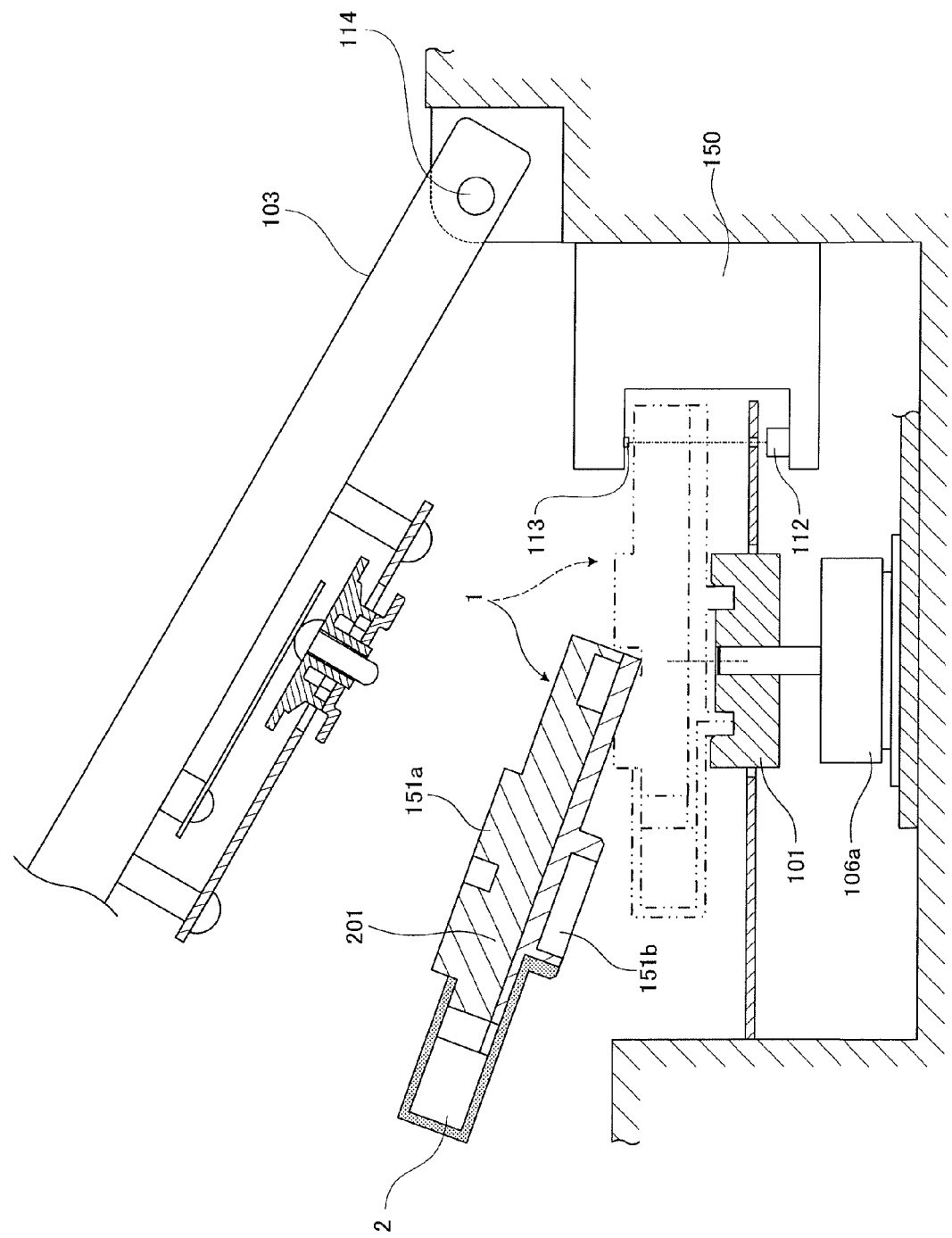
FIG. 29 is a cross-sectional view of FIG. 18.
Figure 30:
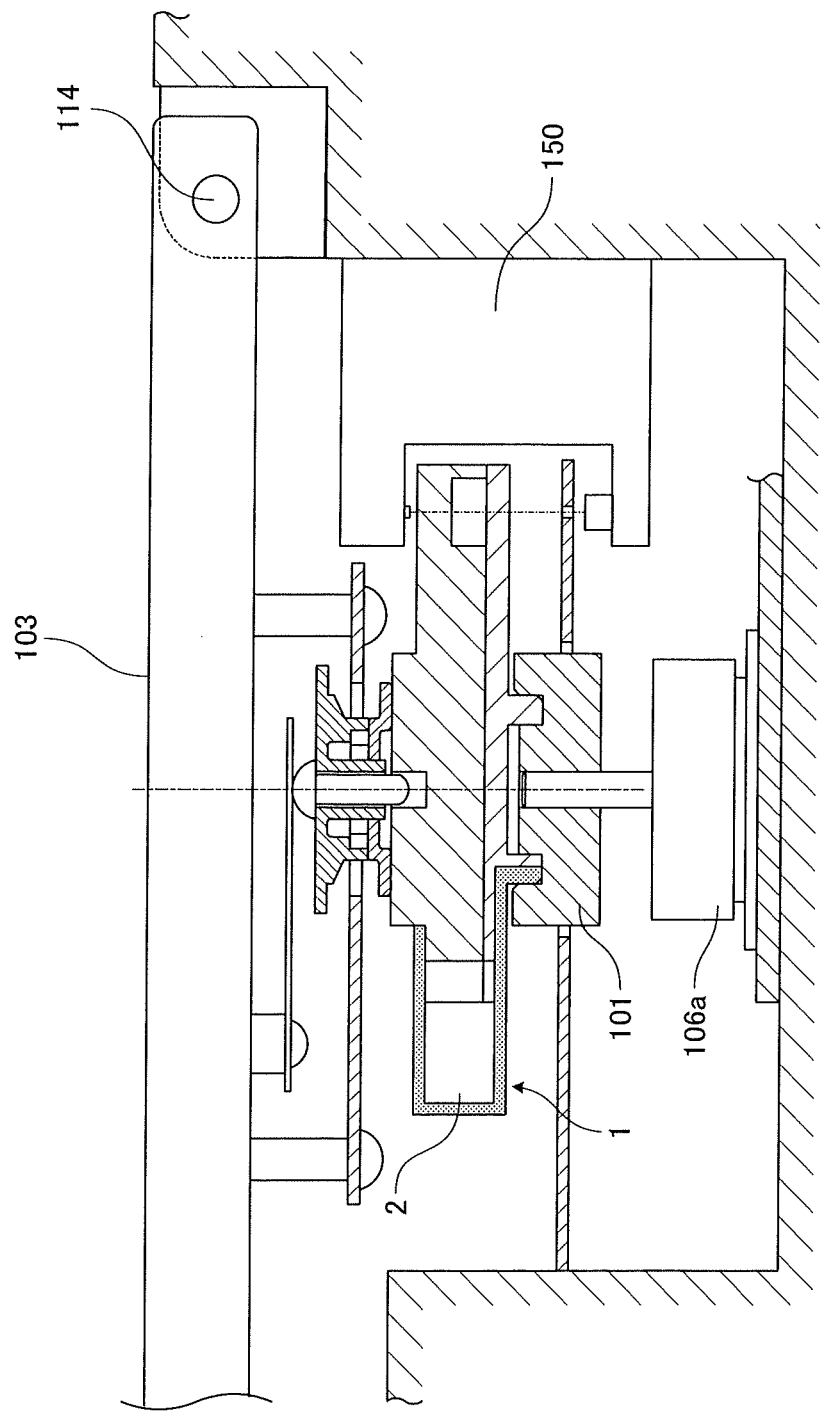
FIG. 30 is a cross-sectional view taken during an analysis performed by an analysis apparatus.

Subsequently, the user sets the analysis device 1 on the analysis apparatus 100 as illustrated in FIGS. 18, 29, and 30. FIG. 29 illustrates a state where the door 103 is opened and the analysis device 1 is to be set. FIG. 30 illustrates a state during rotation where the door 103 has been closed and the analysis device 1 is held sandwiched between the rotor 101 and the door 103. Reference numeral 150 denotes an optical reading apparatus to which a light source 112 and a photodetector 113 are attached so as to oppose each other. In FIG. 28, protrusions 151a and 151b on a primary face of the analysis device 1 illustrated in FIG. 30 have been omitted.

Figure 31:
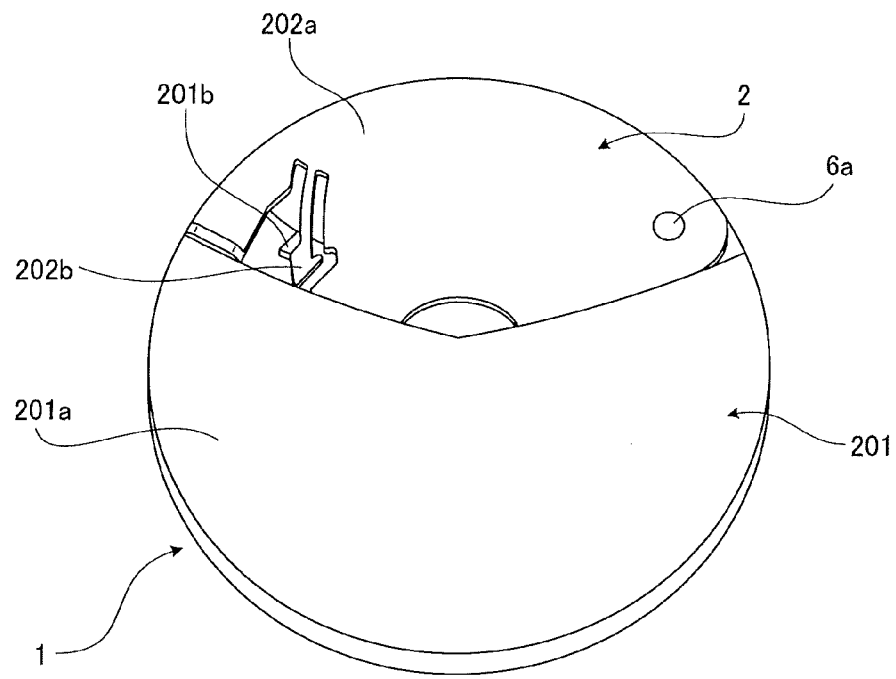
FIG. 31 is a perspective view of an unused state of a lidded container according to the eighth embodiment of the present invention.

FIG. 31 illustrates an unused analysis device 1 that has been supplied to a user.

Figure 32:
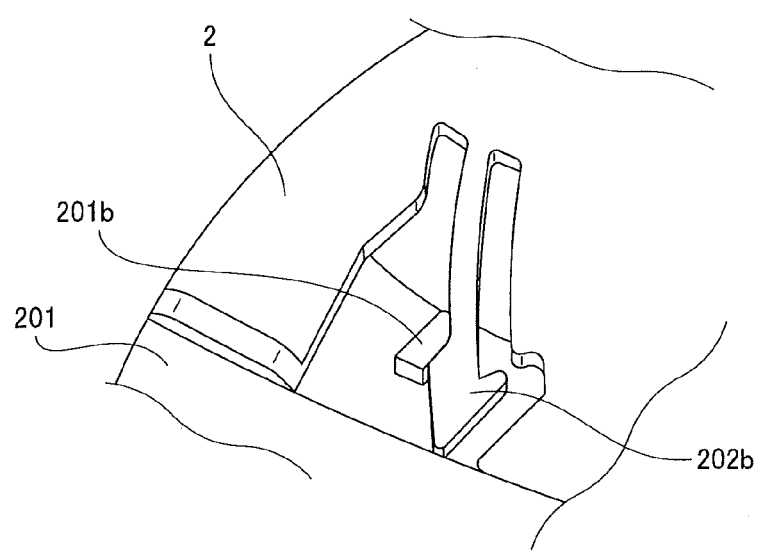
FIG. 32 is an enlarged view of substantial parts illustrated in FIG. 31.

A device main body 201 as a container main body is formed in the same manner as in the embodiments described above by pasting together a base substrate 3 and a cover substrate 4. A locking piece 201b as a locking portion is provided on a primary face 201a of the device main body 201. A hooked section 202b is provided on a primary face 202a of the protective cap 2. FIG. 32 is a partial enlarged view of the locking piece 201b and the hooked section 202b at this point. The unused state is either a state where stress that elastically deforms the hooked section 202b is not acting on the hooked section 202b or a state where stress that causes elastic deformation is hardly acting on the hooked section 202b. Therefore, even when the analysis device 1 has been preserved over a long period of time prior to use, a functional decline due to resin deformation does not occur.

Figure 33A:
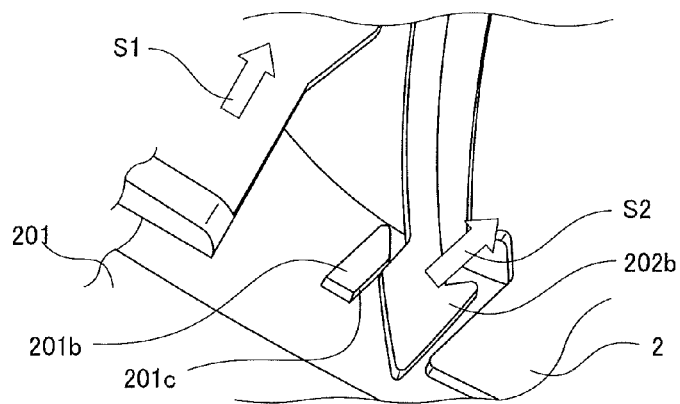
FIG. 33A is an enlarged view of substantial parts before opening a protective cap of a lidded container according to the eighth embodiment of the present invention.
Figure 33B:
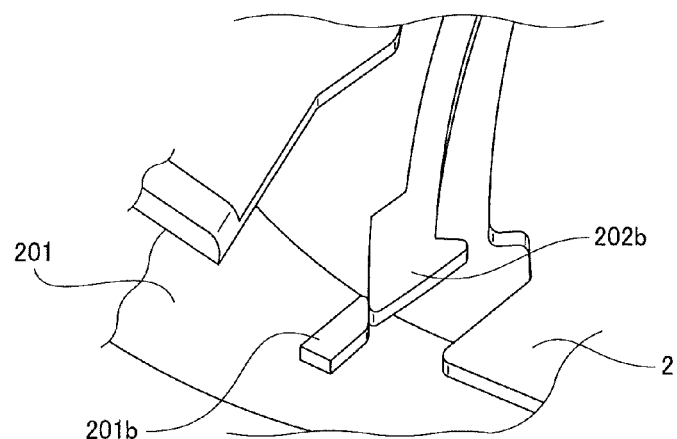
FIG. 33B is an enlarged view of substantial parts when a protective cap of a lidded container according to the eighth embodiment of the present invention is being opened.
Figure 33C:
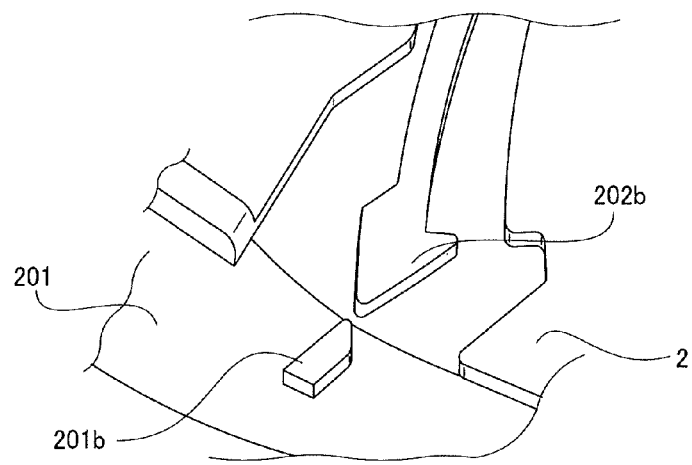
FIG. 33C is an enlarged view of substantial parts when a protective cap of a lidded container according to the eighth embodiment of the present invention is being opened.

When the protective cap 2 is opened in a direction depicted by an arrow S1 centered around a shaft 6a of the device main body 201 upon sampling blood, as illustrated in FIGS. 33A and 33B, a tip of the hooked section 202b slides while the hooked section 202b is being elastically deformed in a direction depicted by an arrow S2 along a first sliding face 201c of the locking piece 201b of the device main body 201. Eventually, as illustrated in FIG. 33C, the tip of the hooked section 202b detaches from the locking piece 201b and the elastic deformation is once again released. By fully opening the protective cap 2, as illustrated in FIG. 28, the inlet 13 of the device main body 201 becomes exposed.

Figure 34A:
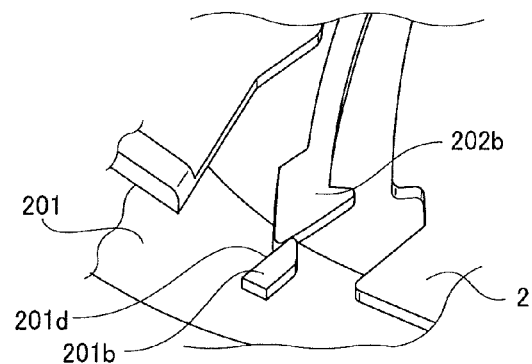
FIG. 34A is an enlarged view of substantial parts when a protective cap of a lidded container according to the eighth embodiment of the present invention is being closed.
Figure 34B:
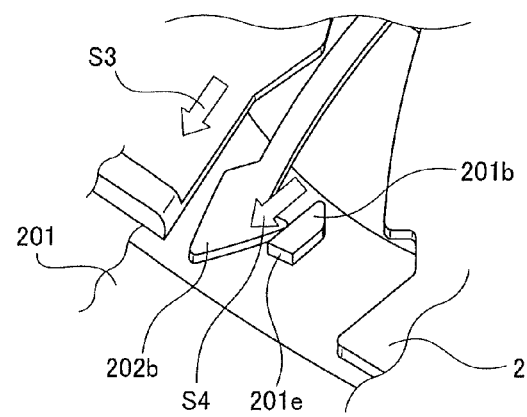
FIG. 34B is an enlarged view of substantial parts when a protective cap of a lidded container according to the eighth embodiment of the present invention is being closed.

When the protective cap 2 is closed in a direction depicted by an arrow S3 centered around a shaft 6a of the device main body 201 after blood is spot-applied on the inlet 13, as illustrated in FIGS. 34A and 34B, the hook 202c slides along a second sliding face 201d of the locking piece 201b and runs upon the locking piece 201b, causing the hooked section 202b to elastically deform in a direction depicted by an arrow S4. Eventually, as illustrated in FIG. 34C, a hook 202c on a tip of the hooked section 202b crosses over the locking piece 201b, and the elasticity of the hooked section 202b causes the hook 202c to engage a bottom 201e of the locking piece 201b.

Figure 34C:
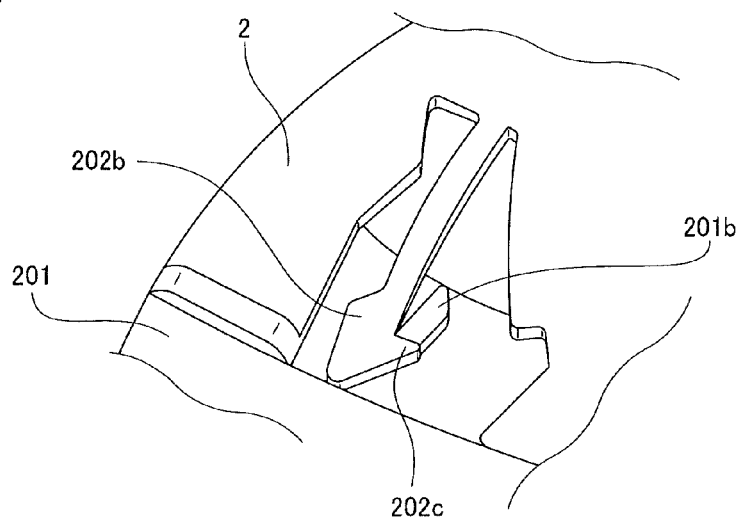
FIG. 34C is an enlarged view of substantial parts after closing a protective cap of a lidded container according to the eighth embodiment of the present invention.

As illustrated in FIG. 34C, with the analysis device 1 supplied for analysis by the analysis apparatus 100 in a locked state where the hooked section 202b is in engagement with the bottom 201e of the locking piece 201b, even when attempting to reopen the protective cap 2, the locked state prevents the protective cap 2 from being easily opened.

In addition, the activation of the locking mechanism of the protective cap 2 also prevents the protective cap 2 from being inadvertently opened by centrifugal force during analysis by the analysis apparatus 100, and also forestalls breakage of the analysis device 1 and the analysis apparatus 100.

After measurement, a used lidded container is desirably discarded as soon as possible. However, even if reuse is accidentally attempted, the protective cap 2 with a reuse prevention mechanism makes it difficult to open the lid, thereby preventing secondary infection or blood infection of the user due to accidental reuse. Lidded containers that primarily collect blood such as the lidded container described above internally include an electrode for analyzing blood as well as chemicals such as an enzyme, a pigment and a mediator, thereby enabling analysis with a simplified method as a disposable sensor. However, the realization of reuse prevention need not be limited to the analysis of blood and is also useful when using lidded containers in regards to health management using urine or sweat or in regards to environmental chemical analysis.

A resin material for molding the protective cap 2 must be flexible. While PP, PE, ABS, POM and the like are sufficient in this regard, the resin material need not be limited thereto.

In the present eighth embodiment, a hooked section 202b is provided on the protective cap 2 and a locking piece 201b is provided on the device main body 201. Alternatively, the hooked section 202b may be provided on the device main body 201 and the locking piece 201b on the protective cap 2.

Ninth Embodiment

Figure 42:
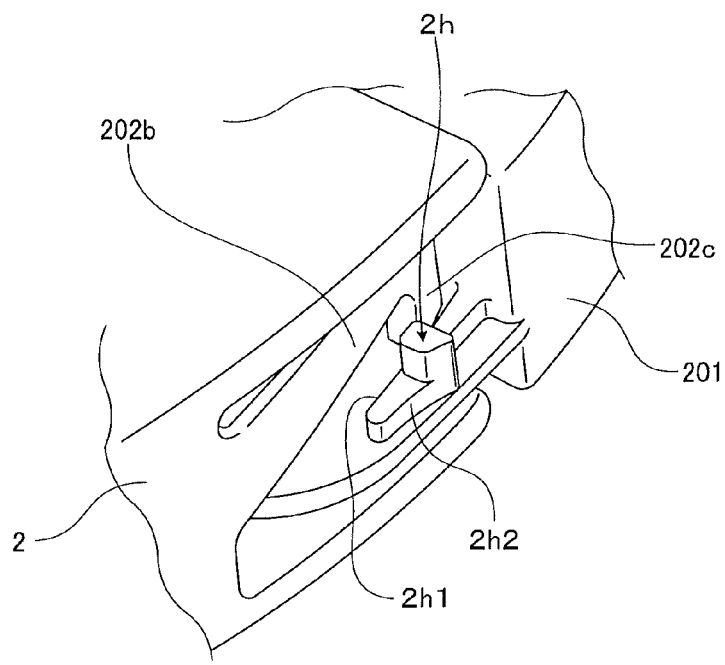
FIG. 42 is an enlarged perspective view of substantial parts according to a tenth embodiment of the present invention.
Figure 43:
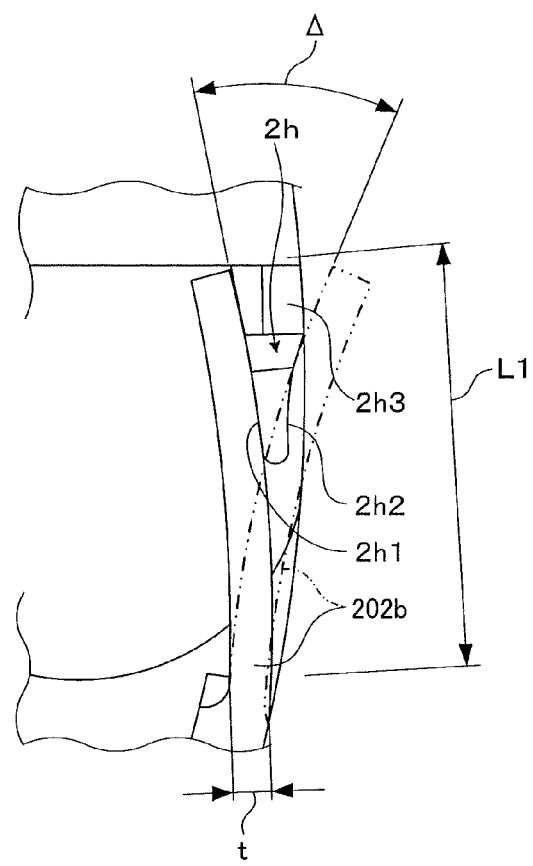
FIG. 43 is an enlarged plan view of substantial parts according to the tenth embodiment of the present invention.

FIGS. 35 to 41 illustrate a ninth embodiment of the present invention. In addition, FIGS. 42 to 44 illustrate a modification.

With the analysis device 1 as a lidded container according to the eighth embodiment, the hooked section 202b and the locking piece 201b are provided on a primary face-side of the analysis device 1. However, in the present ninth embodiment, as illustrated in FIGS. 35 and 36, a hooked section 202b and a locking piece 201b are provided on a peripheral face 220 adjacent to a primary face of an analysis device 1.

Figure 35:
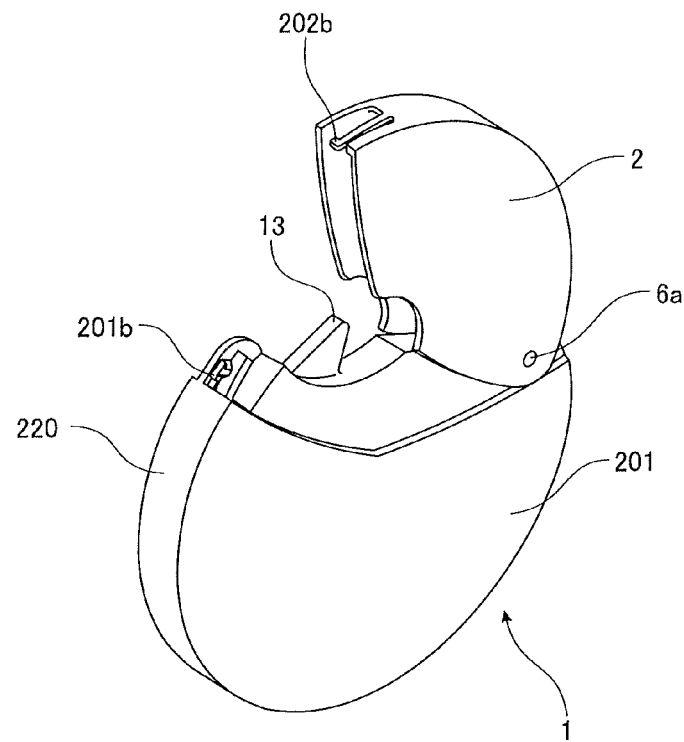
FIG. 35 is a perspective view of an in-use state in which a protective cap of a lidded container according to a ninth embodiment of the present invention has been opened.
Figure 36:
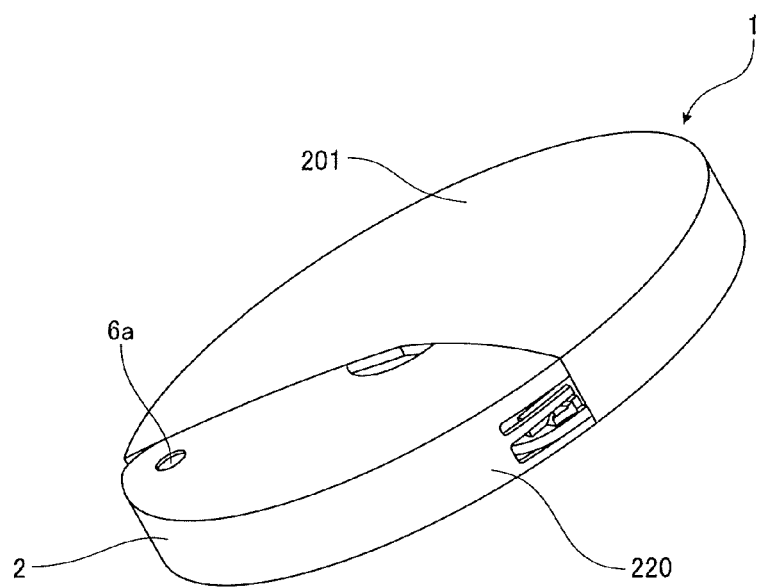
FIG. 36 is a perspective view of an unused state of a lidded container according to the ninth embodiment of the present invention.

FIG. 35 illustrates a state during blood sampling where a protective cap 2 has been opened so as to expose an inlet 13. FIG. 36 illustrates a state before the protective cap 2 is opened as illustrated in FIG. 35.

Figure 37:
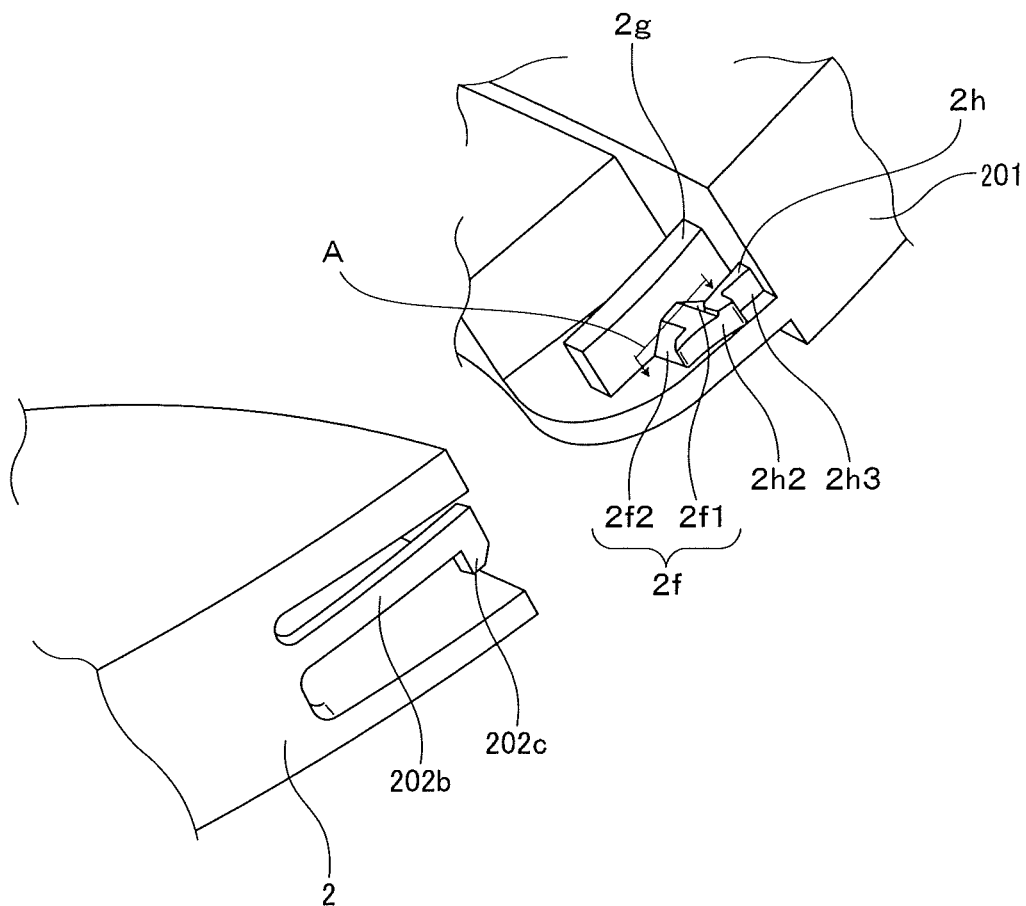
FIG. 37 is an exploded perspective view of a lidded container according to the ninth embodiment of the present invention.

As illustrated in FIG. 37, the hooked section 202b is formed on a peripheral face of the protective cap 2. An angular protrusion 2f and first and second guide walls 2g and 2h are formed on a peripheral face of a device main body 201.

Figure 38:
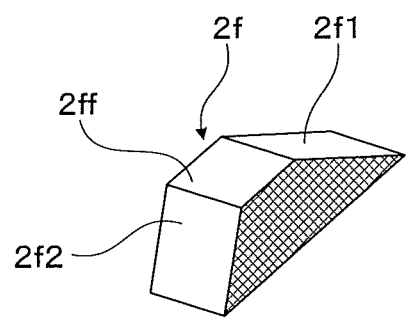
FIG. 38 is an A cross-sectional view of FIG. 37.

A cross section A of the protrusion 2f in a direction that follows a rotational movement path of the protective cap 2 is illustrated in FIG. 38. The protrusion 2f is made up of a first inclined face 2f1 having an ascending gradient in a direction that opens the protective cap 2 and a second inclined face 2f2 connected to a summit 2ff of the first inclined face 2f1 and which has a descending gradient in a direction that opens the protective cap 2.

Formed on the second guide wall 2h are: an inward guide face 2h1 facing the first guide wall 2g; a lateral guide face 2h2 formed on an outer peripheral side of the protrusion 2f with a guide face orientation differentiated from the second inclined face 2f2 of the protrusion 2f by 90 degrees; and a recess 2h3 formed on an end of the lateral guide face 2h2 on a side that is opposite the second inclined face 2f2. The lateral guide face 2h2 is gradually inclined from one end on a side of the second inclined face 2f2 towards the recess 2h3 so as to approach an outer peripheral side of the analysis device 1.

Figure 39:
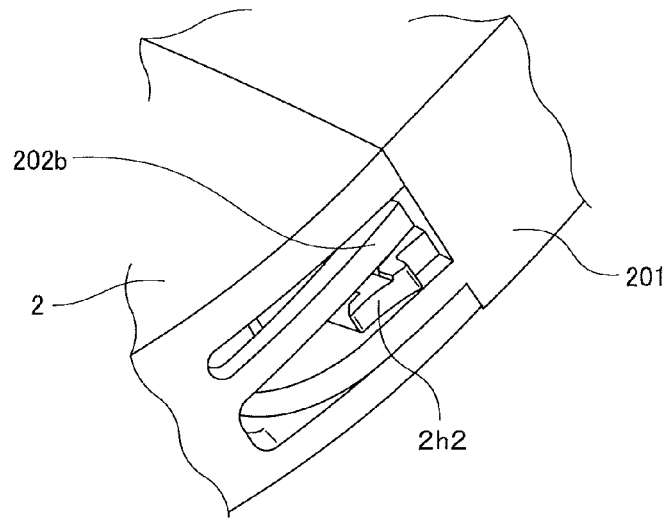
FIG. 39 is an enlarged view of substantial parts illustrated in FIG. 36.
Figure 40:
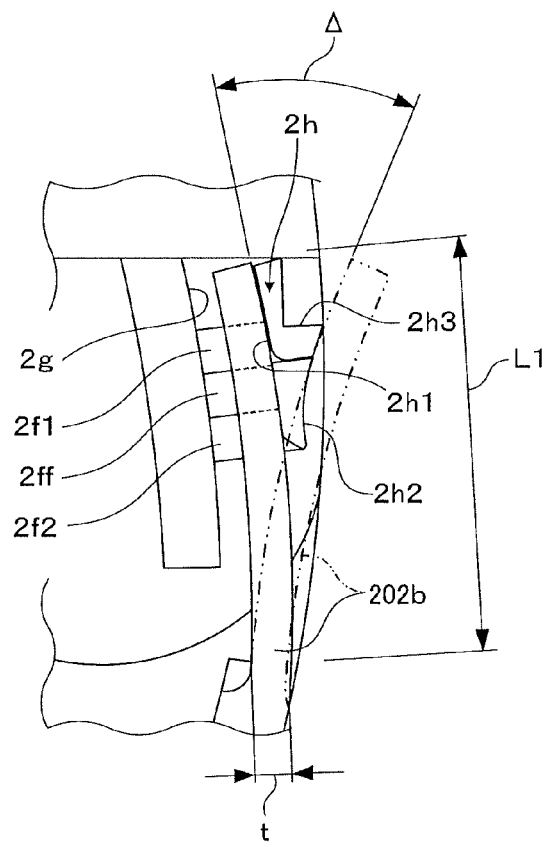
FIG. 40 is an enlarged plan view of substantial parts in an unused state of a lidded container according to the ninth embodiment of the present invention.

In a state before opening the protective cap 2, as illustrated in FIGS. 39 and 40, a hook 202c on a tip of the hooked section 202b of the protective cap 2 has crossed over the first inclined face 2f1 of the protrusion 2f of the device main body 201 and is stationary. This unused state is either a state where stress that elastically deforms the hooked section 202b is not acting on the hooked section 202b or a state where stress that causes elastic deformation is hardly acting on the hooked section 202b. Therefore, even when the analysis device 1 has been preserved over a long period of time prior to use, a functional decline due to resin deformation does not occur.

Figure 41A:
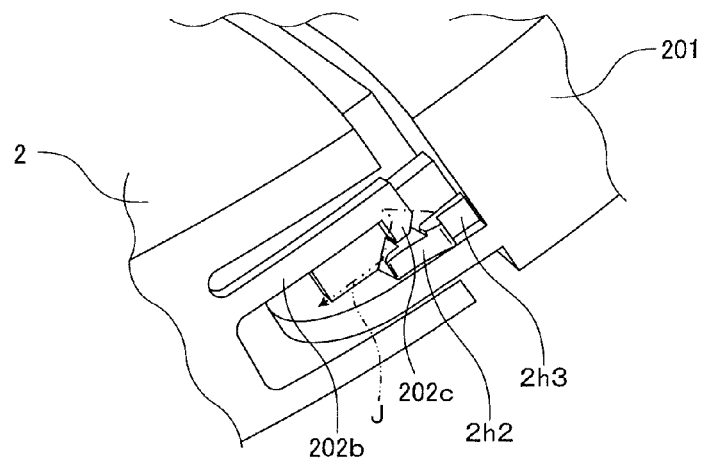
FIG. 41A is an enlarged view of substantial parts when a protective cap of a lidded container according to the ninth embodiment of the present invention has been opened and is now being closed.

When the protective cap 2 is opened centered around a shaft 6a of the device main body 201 from this state, the hook 202c slidingly moves across the first inclined face 2f1 towards the summit, the hooked section 202b gradually elastically deforms in a thickness direction of the analysis device 1 as illustrated in FIG. 41A, and the hooked section 202b is pushed towards the inner side of the analysis device 1 by the inward guide face 2h1 of the second guide wall 2h and slidingly moves while being elastically deformed. When the hook 202c passes the inward guide face 2h1, the elastic deformation that has been acting on the hooked section 202b in a direction that pushes the hooked section 202b towards the inner side of the analysis device 1 is released. Furthermore, as the protective cap 2 is opened, the hook 202c slidingly moves across the second inclined face 2f2. Eventually, the engagement between the hooked section 202b and the protrusion 2f is released to enter a state where no stress acts on the hooked section 202b. An imaginary line J depicts a migration path of the hooked section 202b at this point.

Moreover, the second inclined face 2f2 acts effectively when closing the protective cap 2 to set the protective cap 2 to an unused state.

Figure 41B:
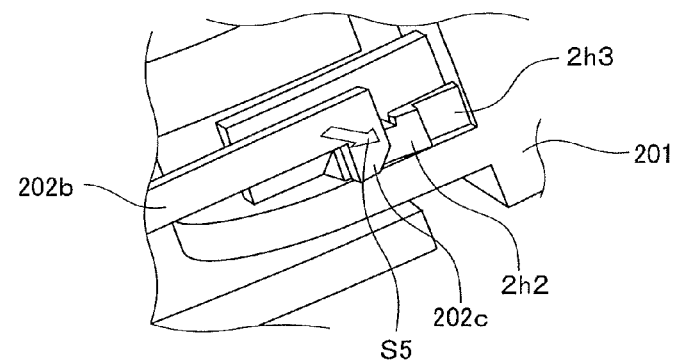
FIG. 41B is an enlarged view of substantial parts when a protective cap of a lidded container according to the ninth embodiment of the present invention has been opened and is now being closed.
Figure 41C:
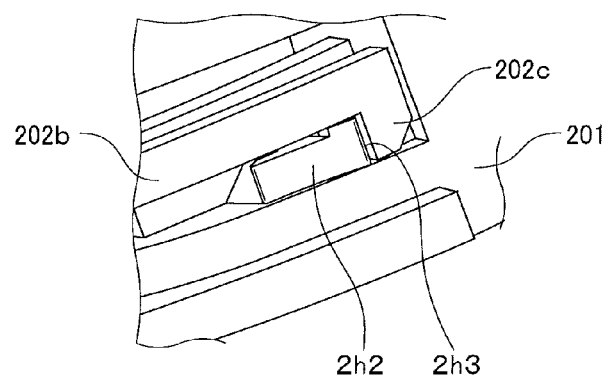
FIG. 41C is an enlarged view of substantial parts when a protective cap of a lidded container according to the ninth embodiment of the present invention has been opened and is now closed.

A fingertip of a testee is pierced by a needle. Blood formed on the fingertip is spot-applied onto the inlet 13, and after blood is spot-applied, the protective cap 2 is closed. At this point, the hook 202c on the tip of the protective cap 2 is pushed out circumferentially outward along the lateral guide face 2h2 and gradually elastically deforms as illustrated in FIG. 41B. Eventually, as illustrated in FIG. 41C, the hook 202c engages the recess 2h3 as a locking portion formed on a trailing end position of the lateral guide face 2h2 by an elastic force of the hooked section 202b. The state illustrated in FIG. 41C represents a state where a reuse prevention mechanism has been activated and reuse cannot be easily performed.

The hooked section 202b depicted by an imaginary line in FIG. 40 represents a state of maximum elastic deformation in a horizontal direction immediately before the hook 202c engages the recess 2h3.

As seen, when opening the protective cap 2, by running on the protrusion 2f provided on a side of the device main body 201 and creating an elastic deformation in a direction perpendicular to a plane, the protective cap 2 can be opened with relatively small resistance.

Next, when closing the protective cap 2, the hooked section 202b is guided by the lateral guide face 2h2 and elastically deforms horizontally outwards (direction depicted by arrow S5) centered around a proximal end of the hooked section 202b, thereby creating a state where the hook 202c engages the recess 2h3 and opening is difficult. Consequently, a user is relieved from accidents due to reuse.

With the locking mechanism described in the present ninth embodiment, by combining movement perpendicular to a plane with movement parallel thereto of the hooked section 202b which accompany the opening and closing the protective cap 2, an flexure of the hooked section 202b from the proximal end can be reduced up to 60% as compared to a case where a similar function is realized only by planar-direction movement. For example, if a length L1 of the hooked section 202b is 8 mm, a thickness t of the hooked section 202b is 1 mm, and a distance from the shaft 6a of the device main body 201 to the hooked section 202b is 46 mm, then an flexure A depicted in FIG. 40 which is 2.5 mm in the case of the locking mechanism according to the eighth embodiment can be reduced by 32% to 1.7 mm.

A resin material for molding the protective cap 2 must be flexible. While PP, PE, ABS, POM and the like are sufficient in this regard, the resin material need not be limited thereto.

In the present ninth embodiment, a hooked section 202b is provided on the protective cap 2 and a locking piece 201b is provided on the device main body 201. Alternatively, the hooked section 202b may be provided on the device main body 201 and the locking piece 201b on the protective cap 2.

Tenth Embodiment

Next, a modification illustrated in FIGS. 42 to 44 will be described.

In the ninth embodiment illustrated in FIGS. 35 to 41, the protrusion 2f and the first guide wall 2g are formed on the device main body 201. In contrast, the present tenth embodiment does not include the angular protrusion 2f and the first guide wall 2g illustrated in FIG. 38. In the following description, parts performing similar actions are assigned similar reference characters to those used in FIGS. 35 to 41.

Specifically, in a state before opening the protective cap 2, as illustrated in FIGS. 42 and 43, a hook 202c on a tip of a hooked section 202b of a protective cap 2 is positioned on an inner side of an inward guide face 2h1 of a second guide wall 2h and is stationary. This unused state is either a state where stress that elastically deforms the hooked section 202b is not acting on the hooked section 202b or a state where stress that causes elastic deformation is hardly acting on the hooked section 202b. Therefore, even when the analysis device 1 has been preserved over a long period of time prior to use, a functional decline due to resin deformation does not occur.

Figure 44A:
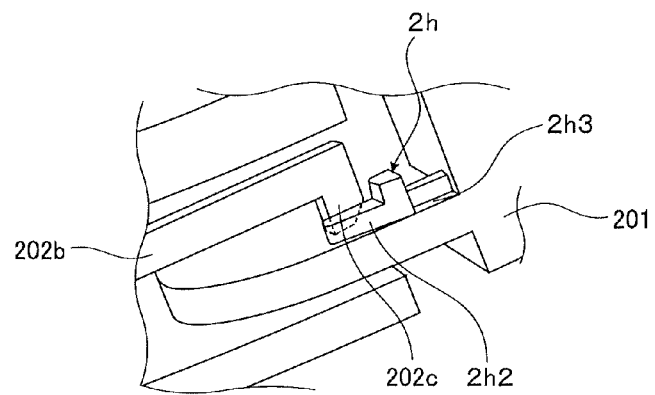
FIG. 44A is an enlarged view of substantial parts after opening and during closing according to the tenth embodiment of the present invention.

When the protective cap 2 is opened centered around a shaft 6a of a device main body 201 from this state, the hook 2c slidingly moves and, as illustrated in FIG. 44A, the hooked section 202b is pushed towards the inner side of the analysis device 1 by the inward guide face 2h1 and slidingly moves while being elastically deformed. The elastic deformation in the direction that pushes the hooked section 202b towards the inner side of the analysis device 1 continues until the abutting of the hook 202c and the second guide wall 2h is released. When the hook 202c passes the inward guide face 2h1, the elastic deformation that has been acting on the hooked section 202b in the direction that pushes the hooked section 202b towards the inner side of the analysis device 1 is released.

Figure 44B:
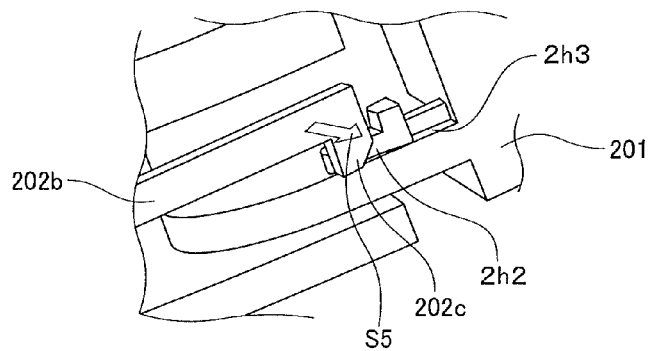
FIG. 44B is an enlarged view of substantial parts after opening and during closing according to the tenth embodiment of the present invention.
Figure 44C:
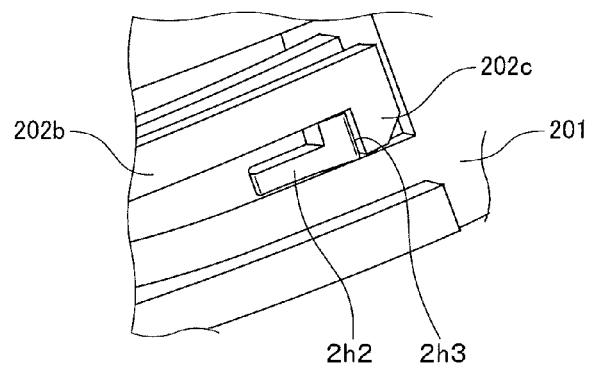
FIG. 44C is an enlarged view of substantial parts after opening and closing according to the tenth embodiment of the present invention.

When closing the protective cap 2, the hook 202c on the tip of the protective cap 2 is pushed out in a circumferentially outward direction S5 along a lateral guide face 2h2 and gradually elastically deforms as illustrated in FIG. 44B. Eventually, as illustrated in FIG. 44C, the hook 202c engages a recess 2h3 formed on a trailing end position of the lateral guide face 2h2 by an elastic force of the hooked section 202b.

Eleventh Embodiment

FIGS. 45 to 49 illustrate an eleventh embodiment of the present invention.

In the ninth and tenth embodiments, the analysis device 1 as a lidded container has been described using a case where an end of the protective cap 2 is pivotally supported by the device main body 201 so as to be rotationally movable between a position where protection object locations of the device main body 201 are covered and a position where the protection object locations are exposed. In the present eleventh embodiment, a description will be given on a case of a lidded container 300 arranged such that by slidingly moving a protective cap 2 set at a position where protection object locations of a device main body 201 are covered along a sliding face between the device main body 201 and the protective cap 2, the protection object locations enter an exposed state and become removable.

In order to obtain blood necessary for analysis, a testee pierces his/her own fingertip using a puncture device to obtain a small amount of blood. The lidded container 300 can hold a plurality of used puncture needles used with the puncture device during disposal.

Figure 45:
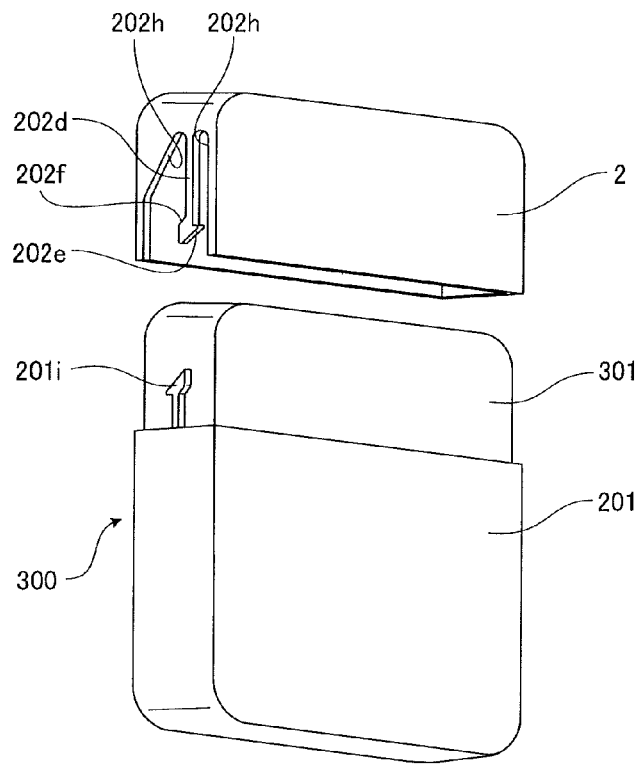
FIG. 45 is a perspective view of an in-use state in which a protective cap of a lidded container according to an eleventh embodiment of the present invention has been opened.
Figure 46:
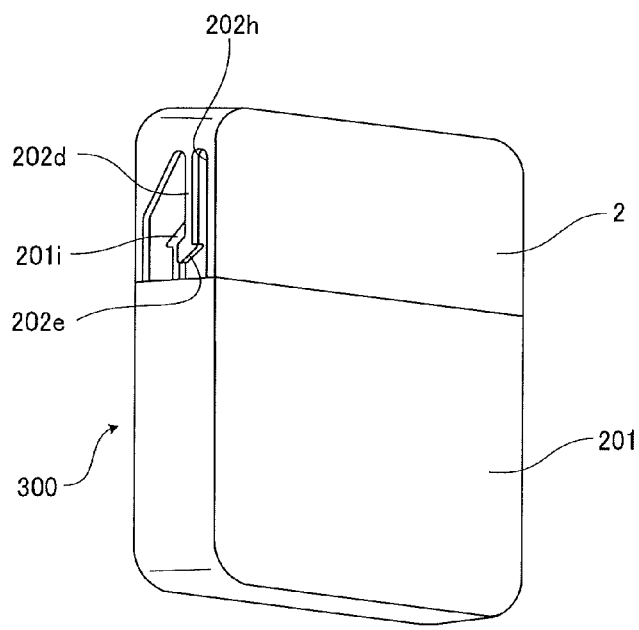
FIG. 46 is a perspective view of an unused state of a lidded container according to the eleventh embodiment of the present invention.
Figure 49:
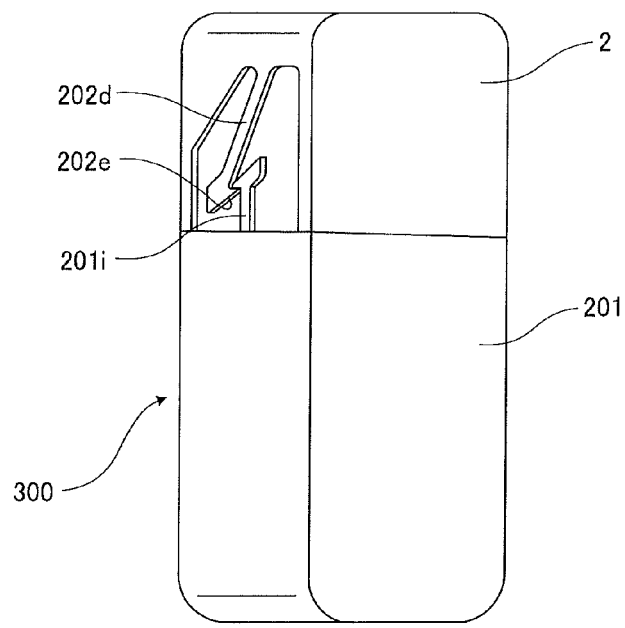
FIG. 49 is a perspective view of an after-use state of a lidded container according to the eleventh embodiment of the present invention.

As illustrated in FIGS. 45 and 46 or FIG. 49, the protective cap 2 can be fitted to the outside of an insertion guide 301 formed on an opening-side periphery of the device main body 201 so as to close an opening of the device main body 201.

A locking piece 201i is formed at a portion of the insertion guide 301 of the device main body 201. By forming a notch 202h on a portion of the protective cap 2 in correspondence to the locking piece 201i, a hooked section 202d is formed on a face that follows the insertion guide 301.

FIG. 46 illustrates an unused lidded container 300.

Figure 47:
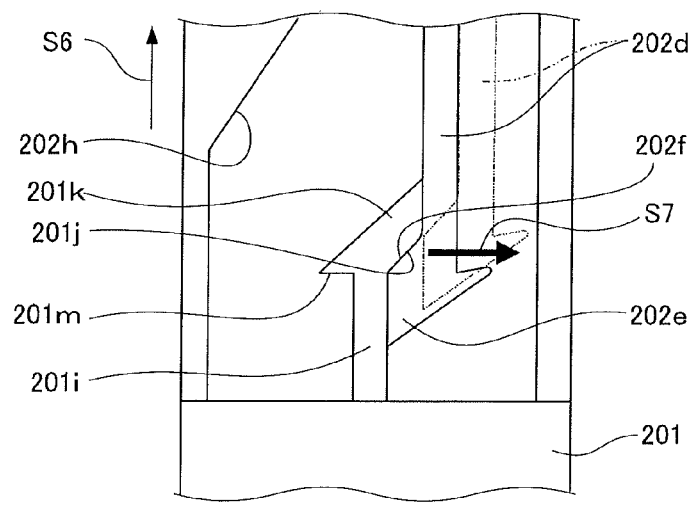
FIG. 47 is an enlarged view of substantial parts during a process of opening a protective cap of a lidded container according to the eleventh embodiment of the present invention.

In a state before opening the protective cap 2, as illustrated in FIG. 47, a first inclined section 202f of a hook 202e on a tip of the hooked section 202d of the protective cap 2 is in engagement with a first inclined face 201j of the locking piece 201i of the device main body 201. This unused state is either a state where stress that elastically deforms the hooked section 202d is not acting on the hooked section 202d or a state where stress that causes elastic deformation is hardly acting on the hooked section 202d. Therefore, even when the lidded container 300 has been preserved over a long period of time prior to use, a functional decline due to resin deformation does not occur.

When the protective cap 2 is lifted in a direction depicted by an arrow S6 with respect to the device main body 201, the first inclined section 202f of the hook 202e slidingly moves across the first inclined face 201j of the locking piece 201i, the hooked section 202d elastically deforms as depicted by an imaginary line, and a tip of the hooked section 202d moves outward as depicted by an arrow S7 in FIG. 47. Eventually, the hook 202e detaches itself from the locking piece 201i.

Figure 48:
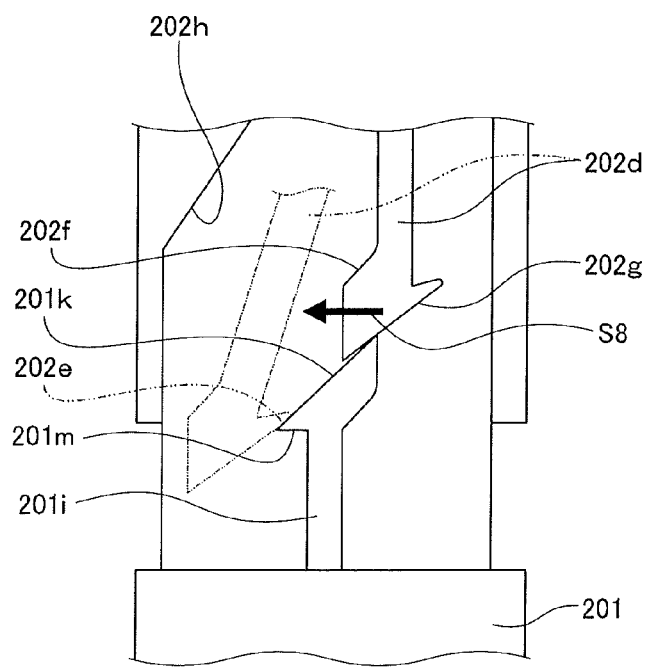
FIG. 48 is an enlarged view of substantial parts during a process of closing a protective cap of a lidded container according to the eleventh embodiment of the present invention.

When the device main body 201 reaches a fixed quantity with used puncture needles and the protective cap 2 is inserted into the device main body 201, an inclined bottom 202g of the hook 202e of the hooked section 202d released from elastic deformation abuts a second inclined face 201k formed on an upper face of the locking piece 201i as illustrated in FIG. 48. As the protective cap 2 is further inserted into the device main body 201, the bottom 202g of the hook 202e slidingly moves across an upper face of the second inclined face 201k of the locking piece 201i, a tip of the hooked section 202d elastically deforms as depicted by an imaginary line in a direction depicted by an arrow S8, and the hook 202e moves outward. Eventually, the hooked section 202d detaches itself from the locking piece 201i, and due to the elastic force of the hooked section 202d, the hook 202e engages a recess 201m of the locking piece 201i as a locking portion as illustrated in FIG. 49. In the state illustrated in FIG. 49, a reuse prevention mechanism has been activated, thereby making reuse impossible.

Twelfth Embodiment

Figure 50:
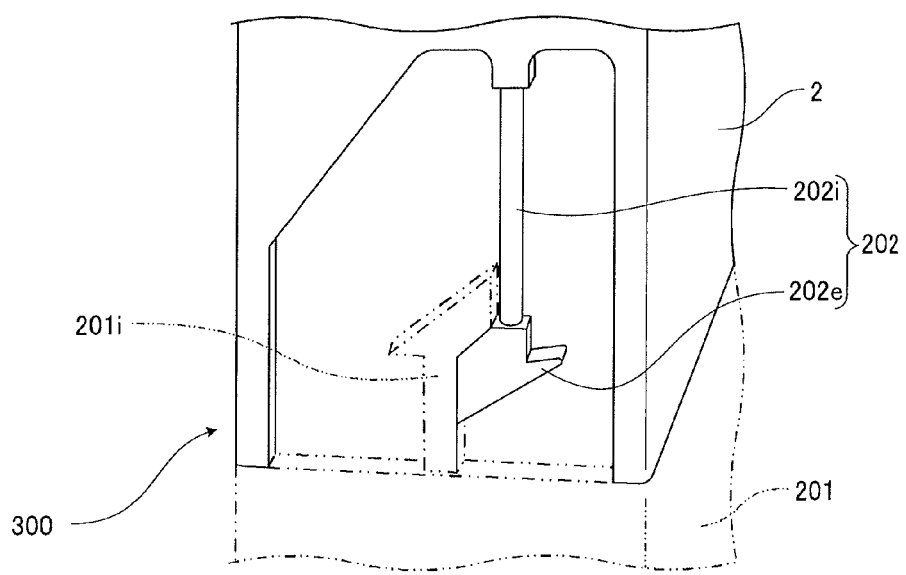
FIG. 50 is a perspective view of substantial parts of a lidded container according to a twelfth embodiment of the present invention.
Figure 51A:
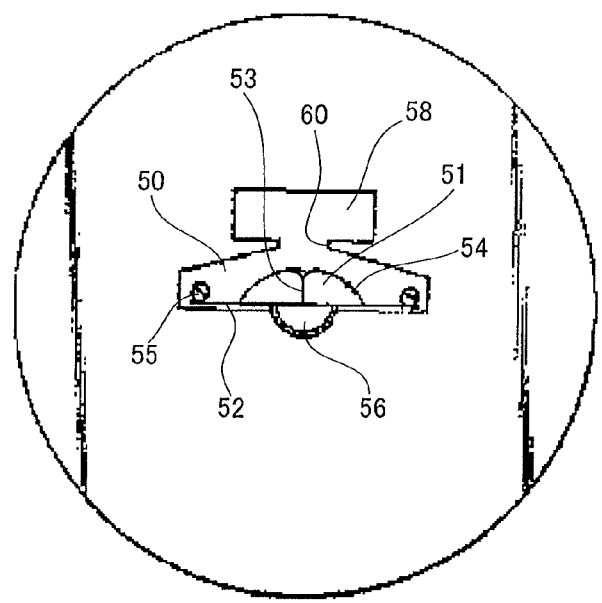
FIG. 51A is a plan view taken before opening a diluent container of an analysis device according to Patent Document 1.
Figure 51B:
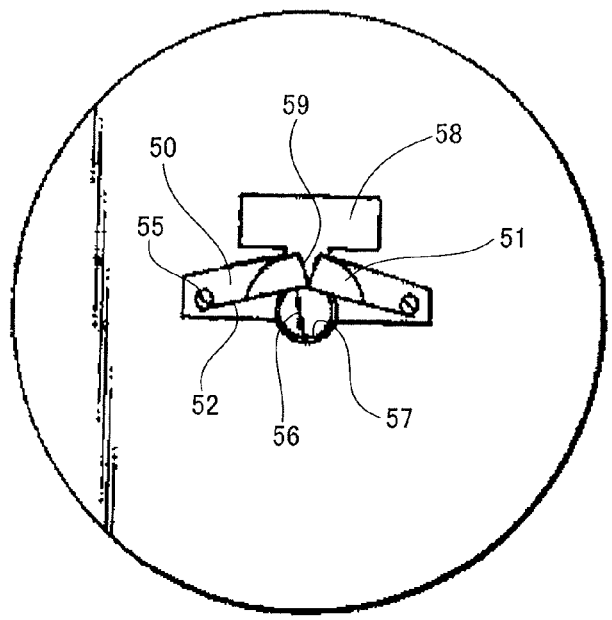
FIG. 51B is a plan view taken after opening a diluent container of an analysis device according to Patent Document 1.
Figure 52:
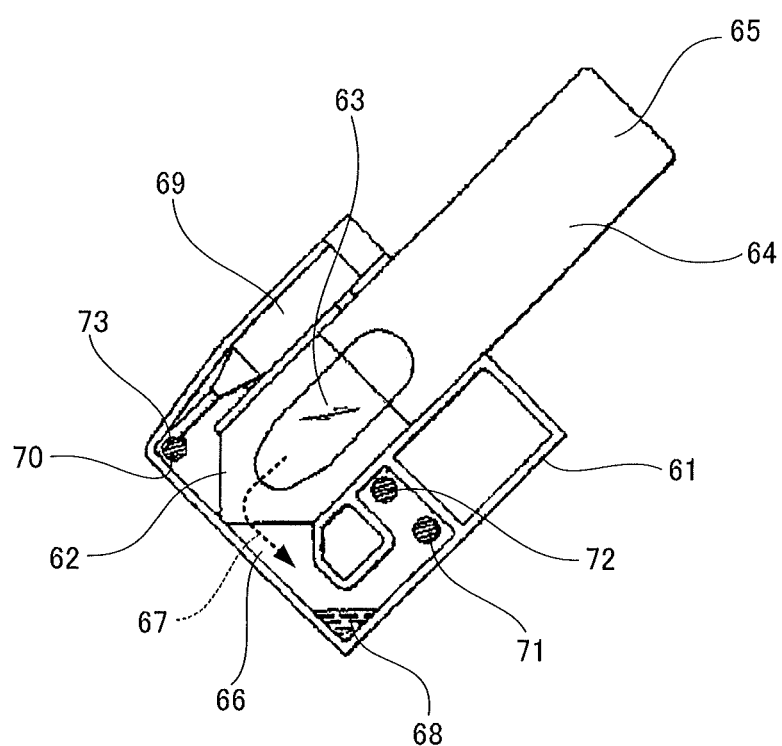
FIG. 52 is a cross-sectional view taken when opening a diluent container of an analysis device according to Patent Document 2.
Figure 53:
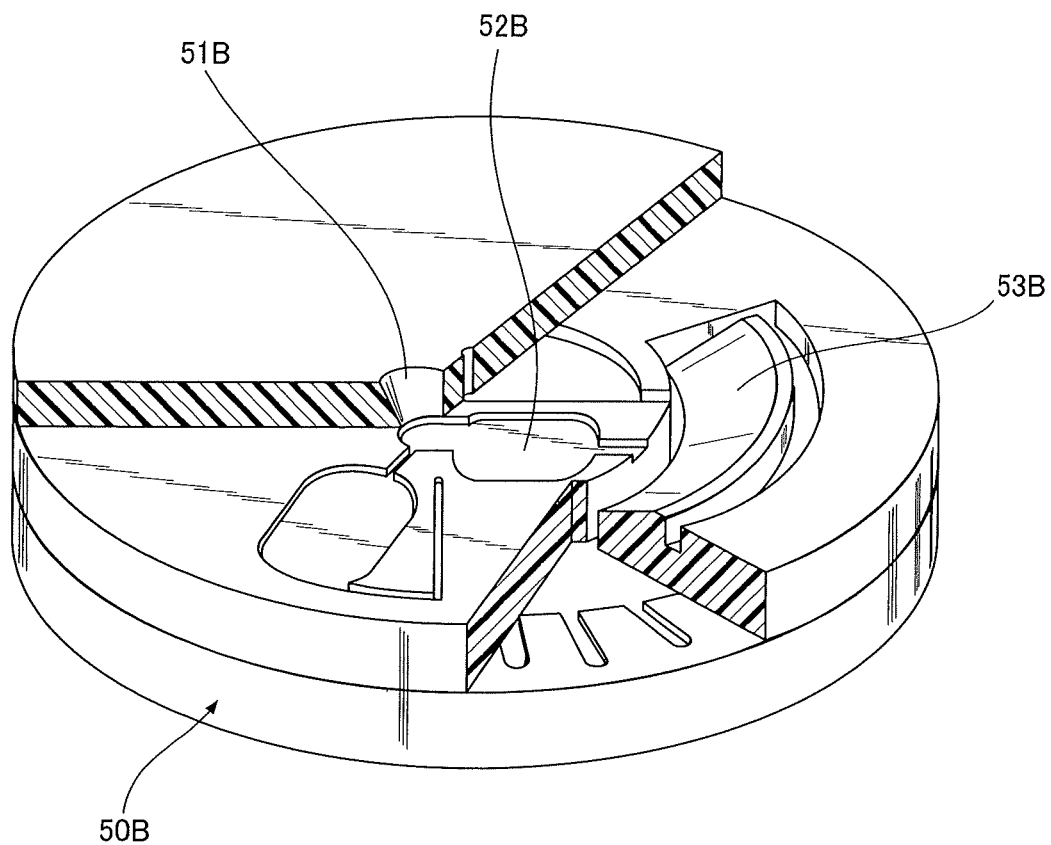
FIG. 53 is a partial cutaway perspective view of an analysis device according to Patent Document 3.

FIG. 50 illustrates a twelfth embodiment of the present invention.

In the eleventh embodiment, the hooked section 202d is integrally formed by forming the notch 202h on the protective cap 2. However, in a case of a lidded container 300 illustrated in FIG. 50, a material of a hooked section 202d differs from a material of a protective cap 2.

Specifically, an arm 202i of the hooked section 202d is formed by a rod-shaped body from a material that differs from the protective cap 2. A hook 202e made of resin and having a predetermined shape is coupled to a tip of the arm 202i. An unused state illustrated in FIG. 50 is either a state where stress that elastically deforms the arm 202i is not acting on the arm 202i or a state where stress that causes elastic deformation is hardly acting on the arm 202i. Therefore, even when the lidded container 300 has been preserved over a long period of time prior to use, a functional decline due to resin deformation does not occur.

As seen, a reuse prevention mechanism can be realized by forming the portion of the arm 202i which requires flexible elastic deformation using a material that is more flexible than the protective cap 2 or, in the case of metal, taking advantage of the characteristics of the metal to come up with a narrow and sinuous structure.

In addition, besides inserting a metallic arm 202i into the protective cap 2, a locking mechanism may be realized by forming parts ranging from the hook 202e to the arm 202i with a material that differs from the protective cap 2 such as butadiene rubber that is an elastomer, and bonding the parts to the protective cap 2 by fitting or using an adhesive.

In the eleventh and twelfth embodiments, the hooked section 202d is provided on the protective cap 2 and the locking piece 201i is provided on the device main body 201. Alternatively, the hooked section 202d may be provided on the device main body 201 and the locking piece 201i on the protective cap 2.

In the eleventh and twelfth embodiments, the lidded container 300 has been described as a container for waste disposal. However, the analysis device 1 described earlier having a microchannel structure with minute surface irregularities formed inside the device main body 201 can be implemented in the same manner.

The present invention can contribute towards the prevention of secondary infection that occurs when coming into contact with infectious or hazardous substances and contamination attributable to contaminants. Furthermore, in cases where a lidded container rotates during use, the present invention prevents accidental opening due to centrifugal force as well as breakage of the lidded container, a rotating apparatus, and various analysis apparatus. Therefore, improvements in safety can be expected.

INDUSTRIAL APPLICABILITY

The present invention is useful as a transfer control unit of an analysis device to be used for component analysis of a liquid collected from a living organism or the like.

The invention claimed is:
1. An analysis device driving apparatus comprising:
a housing having a bottom wall, at least one side wall extending upwardly from the bottom wall and a top opening defined by the at least one side wall;
a rotor located in the housing;
an analysis device set on the rotor for holding a sample liquid to be centrifugally separated, wherein the rotor is configured to apply a centrifugal force to the analysis device;
a door pivotably connected to the at least one side wall of the housing, the door being capable of closing the top opening of the housing and movable between an open state in which the rotor is exposed and a closed state in which the door closes the to opening of the housing and the analysis device set on the rotor is not exposed;
a clamper attached to an inner face of the door; the clamper cooperates with the rotor so as to sandwich the analysis device;
a holding plate that secures the clamper to the inner face of the door;
a flat spring disposed along a radial direction of the rotor, the flat spring is secured to the inner face of the door at one end, the flat spring being positioned to abut an axial end of the clamper and pressing the clamper against the analysis device such that the analysis device is biased against the rotor, when the door is in the closed state; and
a protrusion that abuts the flat spring when the analysis device is uplifted and a distance between the analysis device and the rotor is greater than a permissible value, thereby preventing the analysis device from detaching from the rotor.

2. The analysis device driving apparatus of claim 1, wherein the protrusion is not in contact with the flat spring when the distance between the analysis device and the rotor is smaller than the permissible value.

* * * * *